US009452218B2

(12) United States Patent
Panitch et al.

(10) Patent No.: US 9,452,218 B2
(45) Date of Patent: Sep. 27, 2016

(54) COMPOSITIONS AND METHODS FOR DELIVERY OF KINASE INHIBITING PEPTIDES

(71) Applicant: PURDUE RESEARCH FOUNDATION, West Lafayette, IN (US)

(72) Inventors: Alyssa Panitch, West Lafayette, IN (US); Brandon Seal, Pleasant Grove, UT (US); Jamie L. Brugnano, Lafayette, IN (US); Rush L. Bartlett, West Lafayette, IN (US); Shaili Sharma, Lafayette, IN (US); James McMasters, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/383,701

(22) PCT Filed: Mar. 8, 2013

(86) PCT No.: PCT/US2013/029860
§ 371 (c)(1),
(2) Date: Sep. 8, 2014

(87) PCT Pub. No.: WO2013/134636
PCT Pub. Date: Sep. 12, 2013

(65) Prior Publication Data
US 2015/0018279 A1 Jan. 15, 2015

Related U.S. Application Data

(60) Provisional application No. 61/609,084, filed on Mar. 9, 2012.

(51) Int. Cl.
| | |
|---|---|
| A61K 38/08 | (2006.01) |
| C07K 5/00 | (2006.01) |
| A61K 47/32 | (2006.01) |
| A61K 38/16 | (2006.01) |
| A61K 38/17 | (2006.01) |
| A61K 47/34 | (2006.01) |
| A61K 9/51 | (2006.01) |
| A61K 38/00 | (2006.01) |

(52) U.S. Cl.
CPC ............. *A61K 47/32* (2013.01); *A61K 9/5146* (2013.01); *A61K 38/005* (2013.01); *A61K 38/16* (2013.01); *A61K 38/17* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,175,144 A | 12/1992 | Walser | |
| 5,415,864 A | 5/1995 | Kopecek et al. | |
| 5,565,350 A | 10/1996 | Kmiec et al. | |
| 6,855,693 B2 | 2/2005 | Mochly-Rosen et al. | |
| 6,921,527 B2 | 7/2005 | Platz et al. | |
| 7,041,814 B1 | 5/2006 | Weinstock et al. | |
| 7,135,453 B2 | 11/2006 | Brophy et al. | |
| 7,361,352 B2 | 4/2008 | Birkett et al. | |
| 8,536,303 B2 | 9/2013 | Panitch et al. | |
| 8,741,849 B2 | 6/2014 | Panitch et al. | |
| 2002/0009491 A1 | 1/2002 | Rothbard et al. | |
| 2002/0041899 A1 | 4/2002 | Chudzik et al. | |
| 2002/0128444 A1 | 9/2002 | Gingras et al. | |
| 2003/0134810 A1 | 7/2003 | Springate et al. | |
| 2003/0187232 A1 | 10/2003 | Hubbell et al. | |
| 2003/0190364 A1 | 10/2003 | Panitch et al. | |
| 2005/0153372 A1 | 7/2005 | Greengard et al. | |
| 2005/0181015 A1* | 8/2005 | Zhong | ............................ 424/426 |
| 2006/0024264 A1 | 2/2006 | Kuroda et al. | |
| 2006/0035814 A1 | 2/2006 | Brophy et al. | |
| 2006/0115453 A1 | 6/2006 | Yaffe | |
| 2006/0293234 A1 | 12/2006 | Schroeder et al. | |
| 2007/0026518 A1 | 2/2007 | Healy et al. | |
| 2007/0078092 A1 | 4/2007 | Livnah et al. | |
| 2007/0154448 A1 | 7/2007 | Reid et al. | |
| 2007/0202189 A1 | 8/2007 | Ahlfors | |
| 2008/0003288 A1 | 1/2008 | Bromberg et al. | |
| 2008/0038352 A1 | 2/2008 | Simpson et al. | |
| 2008/0113971 A1 | 5/2008 | Hanau et al. | |
| 2008/0132443 A1 | 6/2008 | Brophy et al. | |
| 2008/0293640 A1 | 11/2008 | Brophy et al. | |

(Continued)

FOREIGN PATENT DOCUMENTS

| | | |
|---|---|---|
| CA | 2689296 | 7/2008 |
| CN | 1747949 | 3/2006 |
| JP | 2002-505077 | 2/2002 |
| JP | 2006-515159 | 2/2004 |
| WO | WO 91/16038 | 10/1991 |

(Continued)

OTHER PUBLICATIONS

Kotsuchibashi (Polym. Chem., 2011, 2, 1362-1367 | 1362-1367).*

(Continued)

*Primary Examiner* — Jeanette Lieb
(74) *Attorney, Agent, or Firm* — Chiesa Shahinian & Giantomasi PC

(57) ABSTRACT

The invention relates to compositions and methods for the treatment of inflammatory disease states. In particular, the invention relates to the use of a nanoparticle incorporated kinase inhibiting peptide to treat inflammatory disease states.

17 Claims, 20 Drawing Sheets

(56) References Cited

U.S. PATENT DOCUMENTS

| | | | |
|---|---|---|---|
| 2009/0149389 A1 | 6/2009 | Panitch et al. | |
| 2009/0176694 A1 | 7/2009 | Brophy et al. | |
| 2009/0176695 A1 | 7/2009 | Brophy et al. | |
| 2009/0196927 A1 | 8/2009 | Panitch et al. | |
| 2009/0258819 A1 | 10/2009 | Brophy et al. | |
| 2009/0269406 A1 | 10/2009 | Panitch et al. | |
| 2010/0004165 A1 | 1/2010 | Brophy et al. | |
| 2010/0009903 A1 | 1/2010 | Brophy et al. | |
| 2010/0098760 A1 | 4/2010 | Panitch | |
| 2010/0158968 A1 | 6/2010 | Panitch | |
| 2011/0052658 A1* | 3/2011 | Panitch et al. | 424/423 |
| 2011/0288036 A1 | 11/2011 | Lander et al. | |
| 2012/0263680 A1 | 10/2012 | Lander et al. | |
| 2014/0112947 A1 | 4/2014 | Panitch et al. | |
| 2014/0342993 A1 | 11/2014 | Panitch et al. | |

FOREIGN PATENT DOCUMENTS

| | | |
|---|---|---|
| WO | WO 93/22443 | 11/1993 |
| WO | WO 02/083933 | 10/2002 |
| WO | WO 03/018758 | 3/2003 |
| WO | WO 03-076333 | 9/2003 |
| WO | WO 2004/075914 | 9/2004 |
| WO | WO 2004/110337 | 12/2004 |
| WO | WO 2005/037236 | 4/2005 |
| WO | WO 2005/114221 | 12/2005 |
| WO | WO 2006/053315 | 5/2006 |
| WO | WO 2006/071456 | 7/2006 |
| WO | WO 2007/053512 | 5/2007 |
| WO | WO 2008/008772 | 1/2008 |
| WO | WO 2008/085191 | 7/2008 |
| WO | WO 2009/021137 | 2/2009 |
| WO | WO 2009/123759 | 10/2009 |
| WO | WO 2010/065206 | 6/2010 |
| WO | WO 2010/068692 | 6/2010 |
| WO | WO 2011/017132 | 2/2011 |

OTHER PUBLICATIONS

Su et al, Post-transcriptional regulation of TNF-iduced expression of ICAM-1 and IL-8 ni human lung microvascular endothelial cells: An obligatory role for the p38 MAPRK-MK2 pathway dissociated with HSP27, 2008, Biochemica et Biophysica Acta, 1783: 1623-1631.
Thomas et al. MAPKAP kinase 2-deficiency prevents neurons from cell death by reducing neuroinflammation-relevance in a mouse model of Parkinson's disease; 2008, Journal of Neurochemistry, 105: 2039-2052.
PCT International Search Report/Writen Opinion for PCT/US2013/029860, completed on Jun. 20, 2013.
Abergel et al., "Biochemical composition of the connective tissue in keloids and analysis of collagen metabolism in keloid fibroblast cultures," J Invest Dermatol, vol. 84, pp. 384-390, May 1985.
Achari et al., 1997, J Polym Sci A: Polym Chem, 35: 2513-2520.
Allaire et al. (1997) Ann Thorac Surg 63(2):582-91.
Altschul et al., Nucleic Acids Res. 25:3389-3402 (1997).
Amano et al., "Formation of Actin Stress Fibers and Focal Adhesions Enhanced by RhoKinase", Science, Feb. 28, 1997, vol. 275, No. 5304, 1308-1311.
Andrew et al., "Spinothalamic lamina I neurons selectively sensitive to histamine: a central neural pathway for itch," Nature Neuroscience, 2001.4(1): p. 72-77.
Andrews et al. (1993). "Report of the AVMA panel on Euthanasia." Journal of the American Veterinary Association, 202(2): 229-249.
Auwerx, "The Human Leukemia-Cell Line, Thp-1-a Multifaceted Model for the Study of Monocyte-Macrophage Differentiation," Experientia, 1991, 47, (1), 22-31.
Bareyre et al., "Inflammation, degeneration and regeneration in the injured spinal cord: insights from DNA microarrays," Trends Neurosci, 2003, 26(10): p. 555-63.

Barone et al., "Inhibition of p38Mitogen-Activated Protein Kinase Provides Neuroprotection in Cerebral Focal Ischemia", Med Res. Rev., 2001, vol. 21, No. 2, 129-145.
Beutler, 1999; J. Rheumatol., 26:16-21.
Biomol International (online), Kinase Inhibitors. 2006, retrieved from http://www.biomol.com/Online_Catalog/Online_Catalog/Products/36/?search=&mode=product&lastSort=&all=tru.
Biomol International (online), Kinases. 2006, retrieved from http://www.biomol.com/Online_Catalog/Online_Catalog/Products/36/?search=&mode=product&lastSort=&all=tru.
Brennan et al., "Expression in Chronic Inflammatory Disease," British Medical Bulletin, 1995, 51(2), 368-384.
Brophy et al. (1998) J Reprod Fertil 114(2):351-355.
Buckenmaier, C.C., $3^{rd}$, et al., "Comparison of antiadhesive treatments using an objective rat model," Am. Surg., 1999, 65(3): 274-82.
Butler et al., "Use of organotypic coculture to study keloid biology," Am J Surg, 195(2): 144-148, Feb. 2008.
Calderon et al., "Increased proliferation in keloid fibroblasts wounded in vitro," J Surg Res, vol. 61, pp. 343-347, Mar. 1996.
Carpino et al., 1972, J. Org. Chem., 37: 3403-3409.
Carroll et al., "Heparin stimulates production of bFGF and TGF-beta 1 by human normal, keloid, and fetal dermal fibroblasts," Med Sci Monit, vol. 9, pp. BR97-BR108, Mar. 2003.
Carroll et al., "Triamcinolone stimulates bFGF production and inhibits TGF-beta 1 production by human dermal fibroblasts," Dermato Surg, vol. 28, pp. 704-709, Aug. 2002.
Chiu et al., "Photodynamic therapy on keloid fibroblasts in tissue-engineered keratinocyte-fibroblast co-culture," Lasers Surg Med, vol. 37, pp. 231-244, Sep. 2005.
Choi, et al., 2005, Angewandte Chemie, 44(41): 6685-6689.
Claverie et al., Comput. Chem., 17:191-201 (1993).
Clowes et al. (1991) J Vasc Surg, 13(6):885-91.
Corpet, et al., Nucleic Acids Research, 16:10881-90 (1988).
Coumans et al. (2001). "Axonal regeneration and functional recovery after complete spinal cord transection in rats by delayed treatment with transplants and neurotrophins." The Journal of Neuroscience, 21(23): 9334-9344.
Dalkowski et al., "Cryotherapy modifies synthetic activity and differentiation of keloidal fibroblasts in vitro," Exp Dermatol, vol. 12, pp. 673-681, Oct. 2003.
Davies et al. (2000) Biochem J 351(Pt 1):95-105.
DeGrado et al. (1999) Annual Review of Biochemistry 68:779-819.
DeMarzo et al., "Prostate stem cell compartments: expression of the cell cycle inhibitor p27Kip1 in normal, hyperplastic, and neoplastic cells", Am. J. Pathol., Sep. 1998, vol. 153, No. 3, 911-919.
Dreiza et al., "Transducible heat shock protein 20 phosphopeptide alters cytoskeletal dynamics," FASEB J, 19: 261-263: 2004.
Dreiza et al. (2005) FASEB J 19(2):261-3.
Duncan et al. (1999) FASEB J 13(13): 1774-86.
Fawell et al., Proc Natl Acad Sci USA, 1994, 91(2): 664-668.
Feldmann et al., "Role of cytokines in rheumatoid arthritis," Annual Review of Immunology, 1996, 14, 397-440.
Feldmann et al., "The role of cytokines in the pathogenesis of rheumatoid arthritis," Rheumatology, 1999, 38, 3-7.
Fields et al., 1990, Int. J. Pept. Protein Res., 35: 161-214.
Firestein et al., "How important are T cells in chronic rheumatoid synovitis? II. T cell-independent mechanisms from beginning to end," Arthritis and Rheumatism 2002, 46, (2), 298-308.
Fisher et al., 1994, Macromol Chem Phys, 195: 679-687.
Fragonas et al., Aricular cartilage repair in rabbits by using suspensions of allogenic chondrocytes in alginate, Biomaterials, 2000, 21(8):795-801.
Frankel et al., Cell, 55(6): 1189-1193, 1988.
Fuchs et al. (1997) J Hypertens 15(3): 301-307.
Fuchs et al. (2000) Am J Physiol Regul Integr Comp Physiol 279(2): R492-8.
Gaestel et al., "Protein kinases as small molecule inhibitor targets in inflammation," Current Medicinal Chemistry, 2007, 14 (21): 2214-2234.
Gaestel, Nat. Rev. Mol. Cell. Biol. 7, 120-130, 2006.
Gerthoffer et al. (2001) J Appl Physiol 91:963-972, 2001.
Green et al., Cell, 1988, 55(60: 1179-1188.

(56) References Cited

OTHER PUBLICATIONS

Gu et al., 2002, J Appl Poly Sci, 86: 3412-3419.
Haapasalo et al., "Truncated trkB.T1 is dominant negative inhibitor of trkB.TK+-mediated cell survival", Biochem Biophys Res Commun, Feb. 9, 2001, vol. 280, No. 5, 1352-1358 (Abstract only).
Hanasono et al., "Autocrine growth factor production by fetal, keloid, and normal dermal fibroblasts," Arch Facial Plast Surg, vol. 5, pp. 26-30, Jan.-Feb. 2003.
Hayess et al., "Effect of protein kinase inhibitors on activity of mammalian small heat-shock protein (HSP25) kinase", *Biochemical Pharmacology*, May 9, 1997, vol. 53, No. 9, 1239-1247.
Hedges et al., J Biol. Chem. 274, 24211-24219, 1999.
Hegen et al., "MAPKAP kinase 2-deficient mice are resistant to collagen-induced arthritis," Journal of Immunology 2006, 177(3), 1913-1917.
Henikoff et al. (1989) Proc. Natl. Acad. Sci. USA 89:10915).
Higgins et al., CABIOS, 5:151-153 (1989).
Higgins et al., Gene, 73:237-244 (1988).
Hirano et al., Journal of Surgical Research 102, 77-84, 2002.
Ho et al., "Synthetic Protein Transduction Domains: Enhanced Transduction Potential in Vitro and in Vivo," *Cancer Research*, 2001, 61: 474-477.
Hong et al., "Growth of keloid-producing fibroblasts in commercially available serum-free media," Otolaryngol Head Neck Surg, vol. 121, pp. 469-473, Oct. 1999.
Hruby, V. J. (2002) Nat Rev Drug Discov 1(11): 847-58.
Huang, et al., Computer Applications in the Biosciences 8:155-65 (1992).
Iwasaki et al ., "Effect of transforming growth factor beta 1 on spinal motor neurons after axotomy," J Neurol Sci, 1997, 147(1): 9-12.
Jacovella, Long-lasting results with hydroxylapatide (Radiesse) facial filler, Plastic and Reconstructive Surgery, 2006, 118(3S):15S-21S.
Jenkins et al., "The pathogenesis of rheumatoid arthritis: A guide to therapy," American Journal of the Medical Sciences, 2002, 323(4), 171-180.
Jobanputra et al., Colorectal Dis. Oct. 2007; 9 Suppl 2: 54-9.
Johnson et al. (2004) Nature Biotech 22(9):1093-1094.
Karlin et al., Proc. Natl. Acad. Sci. USA 90:5873-5787 (1993).
Kent et al. (2004) Ann Vasc Surg 18(2): 135-7.
Knoepp et al. (2000) J Vasc Surg 31:343-353.
Koch et al., "Serum-free keloid fibroblast cell culture: an in vitro model for the study of aberrant wound healing," in Plast Reconstr Surg., vol. 99, 1997, pp. 1094-1098.
Koonin et al., "Origin and evolution of eukaryotic apoptosis: the bacterial connection", Cell Death Differ, Apr. 2002, vol. 9, No. 4, 394-404.
Kossi et al., "Different metabolism of hexose sugars and sucrose in wound fluid and in. fibroblast cultures derived from granulation tissue, hypertrophic scar and keloid," Pathobiology; vol. 68, pp. 29-35, Jan.-Feb. 2000.
Kotlyarov et al., "MAPKAP kinase 2 is essential for LPS-induced TNF-alpha biosynthesis," Nature Cell Biology, 1999, 1(2):94-7.
Kumar et al., "p38 map kinases: Key signaling molecules as therapeutic targets for inflammatory diseases," Nature Reviews Drug Discovery, 2003, 2, (9), 717-726.
Kwon et al., "The cdk2 Binding Domain of p27Kip Correlates with the Inhibition of the Kinase Activity of cdk2/Cyclin Complexes", Biochem Biophys Res Comm, 1996, vol. 220, 703-709.
Langer, 1990 Science 249, 1527-1533.
Lavoie et al., J Biol. Chem. 268, 24210-24214, 1993.
Lavoie et al., Mol Cell Biol. 15: 505-516, 1995.
Liu et al., De novo design, synthesis, and characterization of antimicrobial beta-peptides, J Am Chem Soc, 2001, 123(31): 7553-7559.
LoGerfo et al. (1984) Arch Surg 119:1212-1214.
Lopes et al., "Inhibition of HSP27 phosphorylation by a cell-permeant MAPKAP Kinase 2 inhibitor", *Biochemical and Biophysical Research Communications*, May 8, 2009, vol. 382, No. 3, 535-539.
Macomson et al. (2002) Neurosurgery 51(1): 204-10; discussion 210-1.
Mann et al. (1999) Lancet 354(9189): 1493-8.
Marijnissen et al., Tissue-engineered cartilage using serially passaged articular chondrocytes. Chondrocytes in alginate, combined in vivo with a synthetic (E210) or biologic degradable carrier (DBM), Biomaterials, 2000, 21(6):571-580.
Matsuoka et al., "Ultrastructural characteristics of keloid fibroblasts," Am J Dermatopathol, vol. 10, pp. 505-508, Dec. 1988.
McCormack et al., "The effect of copper tripeptide and tretinoin on growth factor production in a serum-free fibroblast model," Arch Facial Plast Surg, vol. 3, pp. 28-32, Jan.-Mar. 2001.
McLemore et al. (2005) J Am Coll Surg 201(1): 30-6.
Merrifield, 1963, J. Am. Chem. Soc., 85: 2149-2154.
Myers et al., Computer Applic. Biol. Sci., 4:11-17 (1988).
Mosse et al. (1985) Lab Invest 53(5): 556-62.
Needleman et al., J. Mol. Biol., 48: 443 (1970).
Neidigh et al. (2002) Nature Structural Biology 9(6): 425-430.
Pearson et al., Methods in Molecular Biology, 24: 307-331 (1994).
Pearson et al., Proc. Natl. Acad. Sci., 85: 2444 (1988).
Pincus et al., "What Is the Natural-History of Rheumatoid-Arthritis," Rheumatic Disease Clinics of North America, 1993, 19, (1), 123-151.
Pineau et al., Proinflaminatory cytokine synthesis in the injured mouse spinal cord: multiphasic expression pattern and identification of the cell types involved,: J Comp Neurol, 2007, 500(2): p. 267-85.
Pinol et al., "Effect of minoxidil on DNA synthesis in cultured fibroblasts from healthy skin or keloids," Med Cutan Ibero Lat Am, vol. 18, pp. 13-17, 1990.
Podolin et al., "Attenuation of murine collagen-induced arthritis by a novel, potent, selective small molecule inhibitor of I kappa B kinase 2, TPCA-1 (2-[(aminocarbonyl)amino]-5-(4-fluorophenyl)-3-thiophenecarboxamide), occurs via reduction of proinflammatory cytokines and antigen-induced T cell proliferation," Journal of Pharmacology and Experimental Therapeutics, 2005, 312, (1), 373-381.
Polo et al., "Effect of TGF-beta2 on proliferative scar fibroblast cell kinetics," Ann Plast Surg, vol. 43, pp. 185-190, Aug. 1999.
Powell et al. (2003) Molecular and Cellular Biology, 23(15) 5376-5387.
Ridley et al., "Actions of 11-1 are Selectively Controlled by P38 Mitogen-Activated Protein Kinase: regulation of prostaglandin H synthase-2, metalloproteinases, and IL-6 at different levels", *J. Immunol.*, 1997, vol. 158, 3165-3173.
Ross et al., "High-content screening analysis of the p38 pathway: Profiling of structurally related p38 alpha kinase inhibitors using cell-based assays," Assay and Drug Development Technologies, 2006, 4, (4), 397.
Russel et al., "The effect of histamine on the growth of cultured fibroblasts isolated from normal and keloid tissue," J Cell Physiol, vol. 93, pp. 389-393, Dec. 1977.
Sahara et al., "Suppression of in vitro proliferative scar fibroblast contraction by interferon alfa-2b," Wound Repair Regen, vol. 1, pp. 22-27, Jan. 1993.
Saklatvala, "The p38 MAP kinase pathway as a therapeutic target in inflammatory disease," Current Opinion in Pharmacology, 2004, 4, (4), 372-377.
Sawhney et al., Macromolecules (1993) 26, 581-587.
Schenk et al., Signal perception and transduction: the role of protein kinases, *Biochemica et Biophyica Acta*, 1999, vol. 1449, 1-24.
Schwarze et al., Science, 1999, 285(54339: 1569-1572.
Seal et al., Biomacromolecules, 2003, 4: 1572-1582.
Sestier et al., "In vitro toxicity of magnetic fluids evaluated for macrophage cell lines," Journal of Magnetism and Magnetic Materials, 2002, 252, (1-3), 403-405.
Shi et al. (2002) Biol Chem 383:1519-1536 , 2002.
Silver et al., "Regeneration beyond the glial scar," Nature Reviews Neuroscience, 2004. 5(2): p. 146-156.
Smith and Waterman, Adv. Appl. Math., 2: 482 (1981).
Sousa et al. (2007) J Cell Biochem 100(6):1581-1592.
Stokoe, Biochem. J., 1993, 296 (Pt 3): 843-849.

(56) References Cited

OTHER PUBLICATIONS

Takemura et al., "Evaluation of a human monocytic cell line THP-1 model for assay of the intracellular activities of antimicrobial agents against Legionella pneumophila," Journal of Antimicrobial Chemotherapy, 2000, 46, (4), 589-594.
Tanaka et al., 1976, Bulletin of the Chemical Society of Japan, 49(10): 2821-2823.
Tang et al., Synthesis of urea oligomers and their antibacterial activity, Chem Commun, 2005, 1537-1539.
Terashima et al. (2002) J Am Coll Cardiol 39:228A.
Tessier et al. (2004) J Vasc Surg 40(1): 106-14.
Tew et al., De novo design of biomimetic antimicrobial polymers, PNAS, 2002, 99(8): 5110-5114.
Tapash et al., Transdermal and Topical Drug Delivery, pp. 249-297 (1997).
Tyagi et al., J Biol Chem., 2001, 276(5): 3254-3261.
Vassalli, 1992, Annu. Rev. Immunol., 10:411-452.
Verlardo et al., "Patterns of Gene Expression Reveal a Temporally Orchestrated Wound Healing Response in the Injured Spinal Cord," J. Neurosci.: 2004. 24(39): p. 8562-8576.
Vincent et al., "Human Skin Keloid Fibroblasts Display Bioenergetics of Cancer Cells," J Invest Dermatol, 128(3): 702-709, Mar. 2008.
Violette et al., Mimicking helical antibacterial peptides with nonpeptidic folding oligomers, Chemistry and Biology, 2006, 13(5): 531-538.
Wang et al., "Construction of animal models of keloid by tissue engineering," Di Yi Jun Yi Da Xue Xue Bao, vol. 25, pp. 815-819, 832, Jul. 2005.
Wang et al., "p27Kip1 overexpression causes apoptotic death in mammalian cells", Oncogene, Dec. 11, 1997, vol. 15, No. 24, 2991-2997.
Ward et al., "Design of a bioactive cell-penetrating peptide: when a transduction domain does more than transduce", *Journal of Peptide Science*, Oct. 2009, vol. 15, No. 10, 668-674.
Weibel et al., Am. J. Surg. 1973; 126: 345-53.
Woerly et al. (2001). "Spinal cord reconstruction using Neurogel™ Implants and functional recovery after chronic injury." Journal of Neuroscience Research, 66: 1187-1197.
Wooten et al., Comput. Chem., 17: 149-163 (1993).
Worm et al., "Aberrant p27Kip1 promoter methylation in malignant melanoma", Oncogene, Oct. 19, 2000, vol. 19, No. 44, 5111-5115.
Xia et al., "Increased CCN2 transcription in keloid fibroblasts requires cooperativity between AP-1 and SMAD binding sites," Ann Surg, vol. 246, pp. 886-895, Nov. 2007.
Xia et al., "P38 MAP kinase mediates transforming growth factor-beta2 transcription in human keloid fibroblasts," Am J Physiol Regul Integr Comp Physiol, vol. 290, pp. R501-R508, Mar. 2006.
Xu et al., Oncogene 25, 2987-2998, 2006.
Yamanishi et al., "Regulation of joint destruction and inflammation by p53 in collagen-induced arthritis," American Journal of Pathology 2002, 160, (1), 123-130.
Yamboliev et al., Am. J Physiol. Heart Circ Physiol., 278, H1899-1907, 2000.
Yang et al., "Establishment of an animal model of human hyperplastic scar in nude mice," Zhonghua Shao Shang Za Zhi, vol. 20, pp. 82-84, Apr. 2004.
Yang et al., "Early expression and cellular localization of proinflammatory cytokines interleukin-I beta, interleukin-6, and tumor necrosis factor-alpha in human traumatic spinal cord injury," Spine, 2004. 29(9): p. 966-71.
Zong, X., et al., "Prevention of postsurgery-induced abdominal adhesions by electrospun bioabsorable nanofibrous poly(lactide-co-clucolide)-based membranes," Am. Surg., 2004, 240(5): p. 910-5.
Colomer, Sub-Cellular Biochemistry, 2007, 45: 169-214.
Inhibitor Sourcebook, Second Edition, Publisher: Emd (2006), ASIN: B001O2J5A4 (www.emdchemicals.com/showBrochure/201001.140/ProNet.pdf).
Zhu et al., Mechanisms of Signal Transduction: MAPK-activated Protein Kinase 2 Differentially Regulates Plasmodium falciparum Glycosylphosphatidylinositol-induced Production of Tumor Necrosis Factor-α and Interleukin-12 in Macrophages, 2008; Journal of Biochem; 284: 15750-15761.
Schindler et al., Examination of the kinetic mechanism of mitogen-activated protein kinase activated protein kinase-2, Biochimica et Biophysica Acta, Jul. 29, 2002, 1598(1-2): 88-97.
Burgess et al., J of Cell Bio., 1990, 111: 2129-2138.
Bowie et al., Science, 1990, 247: 1306-1310.
Pawson et al., Science, 2003, 300: 445-452.
Zhongshu Song et al., "Fusarin C biosynthesis in Fusarium moniliforme and Fusarium venenatum," *Chembiochem*, 2004, 5(9): 1196-1203.
Morrison et al., "Combinatorial alanine-scanning," Current Opinion in Chemical Biology, 2001, 5:302-307.
Del Gaizo et al. A Novel TAT-Mitochondrial Signal Sequence Fusion Protein Is Processed, Stays in Mitochondria, and Crosses the Placenta, Molecular Therapy, 2003, 7(6):720-730.
Yu, Pey-Jen et al; "Vascular injury and modulation of MAPKs: A targeted approach to therapy of restenosis." Cell. Signal. (2007) 19 p. 1359-1371.
Tucker, Erik I. et al; "Prevention of vascular graft occlusion and thrombus-associated thrombin generation by inhibition of factor XI." Blood (2009) 113(4) p. 936-944.
Babapulle, Mohan N. et al; "A hierarchial bayesian meta analysis of randomized clinical trials of drug eluting stents." Lancet (2004) 364 p. 583-91.
Cyrus, Tillmann et al; "Effect of low dose aspirin on vascular inflammation, plaque stability, and atherogenesis in low density lipoprotein receptor deficient mice." Circulation (2002) 106 p. 1282-1287.
Dinarello, C. A.; "The IL-1 family and inflammatory diseases." Clin. Exp. Rheumatol. (2002) 20 (suppl. 27) p. S1-S13.
Tourneau Christophe Le et al; "Dose escalation methods in phase I cancer clinical trials." J. Natl. Cancer. Inst. (2009) 101 (10) p. 708-720, publication date May 20, 2009.
Schneider et al., 1998, In Vivo Evaluation of hsp27 as an Inhibitor of Actin Polymerization: Hsp27 Limits Actin Stress Fiber and Focal Adhesion Formation After Heat Shock, Journal of Cellular Physiology, 177: 575-584.
Beck et al., 2000, Molecular chaperones in the kidney: distribution, putative roles, and regulation, Am J Physiol Renal Physiol, 279: 203-215.
Keezer et al., Angiogenesis Inhibitors Target the Endothelial Cell Cytoskeleton through Altered Regulation of Heat Shock Protein 27 and Cofilin, Cancer Res, 63: 6405-6412.

\* cited by examiner

COMPOSITIONS AND METHODS FOR DELIVERY OF KINASE INHIBITING PEPTIDES

CROSS-REFERENCE TO RELATED APPLICATIONS

This application is a national stage entry under 35 USC §371(b) of International Application No. PCT/US2013/029860, filed Mar. 8, 2013, and claims the benefit under 35 USC §119(e) of U.S. Provisional Application Ser. No. 61/609,084, filed on Mar. 9, 2012, the entire disclosures of which are incorporated herein by reference.

GOVERNMENT RIGHTS CLAUSE

This invention was made with government support under HL106792 awarded by the National Institutes of Health. The government has certain rights in the invention.

TECHNICAL FIELD

The invention relates to compositions and methods for the treatment of inflammatory disease states. In particular, the invention relates to compositions and methods for the treatment of inflammatory disease states with a nanoparticle incorporated kinase inhibiting peptide.

BACKGROUND AND SUMMARY OF THE INVENTION

Nanoparticles are submicron materials that often possess different properties than bulk material of the same kind. Nanoparticles have been studied for uses in many fields, including diagnostic and therapeutic applications in the life sciences. Because of their small size and unique properties, nanoparticles often have enhanced distribution in the body compared to larger sized particles. Further, nanoparticles may be specifically directed to particular targets in the body by attaching one or more components to the nanoparticle surface (i.e. functionalization). Functionalization of a nanoparticle with a component having affinity for a specific target in the body can direct the nanoparticle to tissues containing the target molecule.

Expansion of nanoparticles at room temperature can facilitate rapid loading of degradation sensitive therapies by passive diffusion. Thermosensitive polymer poly(N-isopropylacrylamide), abbreviated poly(NIPAm), has a physiologically relevant lower critical solution temperature (LCST) between 31-33° C. This LCST causes the polymer to expand at room temperature and contract under physiological conditions. Charged carboxylic co-monomers, such as acrylic acid, are traditionally added to poly(NIPAm) nanoparticles in order to increase colloidal stability and provide a secondary site for chemical modification. In addition to carboxylic co-monomers, it is possible to incorporate sulfated co-monomer 2-acrylamido-2-methyl-1-propanesulfonic acid (AMPS) into poly(NIPAm) nanoparticles.

As described herein, the addition of AMPS into poly(NIPAm) nanoparticles greatly enhances the electrostatic attraction of kinase inhibiting peptides and the nanoparticles which results in increased drug loading. In addition, Applicants have shown that anti-inflammatory kinase inhibiting peptides can be used to target mitogen activated protein kinase activated protein kinase 2 (MK2) to reduce production of pro-inflammatory cytokines and suppress inflammation. As herein described, poly(NIPAm-AMPS) nanoparticles incorporated with or coupled to kinase inhibiting peptides can be used to selectively diffuse through cartilage and significantly suppress cytokine production. For example, the nanoparticle incorporated kinase inhibiting peptides described herein can be used for interarticular therapies, e.g. to treat inflammatory diseases.

Several embodiments of the invention are described by the following enumerated clauses:

1) A composition comprising at least one kinase inhibiting peptide incorporated with a nanoparticle, wherein the nanoparticle comprises at least one copolymerized monomer having an anionic side chain and at least one additional copolymerized monomer.

2) The composition of clause 1 wherein the kinase inhibiting peptide is an MK2 inhibitor peptide.

3) The composition of any one of clauses 1 and 2 wherein the amino acid sequence of the kinase inhibiting peptide has at least 90% sequence identity to a peptide selected from the group consisting of YARAAARQARAKALARQLGVAA, YARAAARQARAKALNRQLGVA, FAKLAARLYRKALARQLGVAA, KAFAKLAARLYRKALARQLGVAA, HRRIKAWLKKIKALARQLGVAA, YARAAARQARAKALNRQLAVAA, and YARAAARQARAKALNRQLAVA.

4) The composition of any one of clause 1 to 3 wherein the at least one copolymerized anionic monomer is 2-acrylamido-2-methyl-1-propanesulfonic acid.

5) The composition of any one of clauses 1 to 4 wherein the at least one additional copolymerized monomer is N-isopropylacrylamide.

6) The composition of any one of clauses 1 to 5 further comprising a crosslinker.

7) The composition of clause 6 wherein the crosslinker is selected from the group consisting of N,O-dimethacryloylhydroxylamine, divinyl adipate, N,N-Bis(acryloyl)cystamine, and N,N'-methylenebisacrylamide.

8) The composition of any one of clauses 1 to 6 further comprising a pharmaceutically acceptable carrier.

9) The composition of clause 8 wherein the carrier is a liquid carrier and is selected from the group consisting of saline, glucose, alcohols, glycols, esters, amides, and a combination thereof.

10) An effective dose of the composition of any of clauses 1 to 9 for administration to a patient, wherein the effective dose ranges from about 1 ng to about 1 mg per kilogram of body weight.

11) An effective dose of the composition of any of clauses 1 to 9 for administration to a patient, wherein the effective dose ranges from about 1 pg to about 10 ng per kilogram of body weight.

12) An effective dose of the composition of any of clauses 1 to 9 for administration to a patient, wherein the effective dose ranges from about 1 µg to about 100 µg per kilogram of body weight.

13) The composition of any one of clauses 1 to 12 wherein the kinase inhibiting peptide has at least 90% sequence identity to YARAAARQARAKALARQLGVAA.

14) The composition of any one of clauses 1 to 12 wherein the kinase inhibiting peptide has at least 90% sequence identity to YARAAARQARAKALNRQLGVA.

15) The composition of any one of clauses 1 to 12 wherein the kinase inhibiting peptide has at least 90% sequence identity to FAKLAARLYRKALARQLGVAA.

16) The composition of any one of clauses 1 to 12 wherein the kinase inhibiting peptide has at least 90% sequence identity to KAFAKLAARLYRKALARQLGVAA.

17) The composition of any one of clauses 1 to 12 wherein the kinase inhibiting peptide has at least 90% sequence identity to HRRIKAWLKKIKALARQLGVAA.

18) The composition of any one of clauses 1 to 12 wherein the kinase inhibiting peptide has at least 90% sequence identity to YARAAARQARAKALNRQLAVAA.

19) The composition of any one of clauses 1 to 12 wherein the kinase inhibiting peptide has at least 90% sequence identity to YARAAARQARAKALNRQLAVA.

20) The composition of any one of clauses 1 to 19 wherein the at least one copolymerized anionic monomer is 2-acrylamido-2-methyl-1-propanesulfonic acid, and wherein the at least one additional copolymerized monomer is N-isopropylacrylamide.

21) The composition of any one of clauses 1 to 20 wherein the at least one copolymerized anionic monomer is 2-acrylamido-2-methyl-1-propanesulfonic acid, wherein the at least one additional copolymerized monomer is N-isopropylacrylamide, and wherein the kinase inhibiting peptide is KAFAKLAARLYRKALARQLGVAA.

22) The composition of any one of clauses 1 to 21 wherein the at least one copolymerized anionic monomer is 2-acrylamido-2-methyl-1-propanesulfonic acid, wherein the at least one additional copolymerized monomer is N-isopropylacrylamide, wherein the crosslinker is N,O-dimethacryloylhydroxylamine, and wherein the kinase inhibiting peptide is KAFAKLAARLYRKALARQLGVAA.

23) The composition of any one of clauses 1 to 22 wherein the at least one additional copolymerized monomer and the copolymerized anionic monomer are present in the composition at a ratio selected from the group consisting of about 5:1, about 8:1, about 9:1, about 10:1, about 11:1, about 12:1, and about 15:1.

24) The composition of any one of clauses 1 to 23 wherein the at least one additional copolymerized monomer and the copolymerized anionic monomer are present in the composition at a ratio of about 10:1.

25) A method for treating osteoarthritis, the method comprising the step of administering a composition comprising at least one kinase inhibiting peptide incorporated with a nanoparticle, wherein the nanoparticle comprises at least one copolymerized anionic monomer and at least one additional copolymerized monomer.

26) The method of clause 25 wherein the kinase inhibiting peptide is an MK2 inhibitor peptide.

27) The method of any one of clauses 25 and 26 wherein the amino acid sequence of the kinase inhibiting peptide has at least 90% sequence identity to a peptide selected from the group consisting of YARAAARQARAKALARQLGVAA, YARAAARQARAKALNRQLGVA, FAKLAARLYRKALARQLGVAA, KAFAKLAARLYRKALARQLGVAA, HRRIKAWLKKIKALARQLGVAA, YARAAARQARAKALNRQLAVAA, and YARAAARQARAKALNRQLAVA.

28) The method of clause 25 to 27 wherein the at least one copolymerized sulfonic monomer is 2-acrylamido-2-methyl-1-propanesulfonic acid.

29) The method of any one of clauses 25 to 28 wherein the at least one additional copolymerized monomer is N-isopropylacrylamide.

30) The method of any one of clauses 25 to 29 wherein the nanoparticle further comprising a crosslinker.

31) The method of clause 30 wherein the crosslinker is selected from the group consisting of N,O-dimethacryloylhydroxylamine, divinyl adipate, N,N-Bis(acryloyl)cystamine, and N,N'-methylenebisacrylamide.

32) The method of any one of clauses 25 to 31 further comprising a pharmaceutically acceptable carrier.

33) The method of clause 32 wherein the carrier is a liquid carrier and is selected from the group consisting of saline, glucose, alcohols, glycols, esters, amides, and a combination thereof.

34) The method of any one of clauses 25 to 33 wherein the composition is administered to a patient in an effective dose, wherein the effective dose ranges from about 1 ng to about 1 mg per kilogram of body weight.

35) The method of any one of clauses 25 to 33 wherein the composition is administered to a patient in an effective dose, wherein the effective dose ranges from about 1 pg to about 10 ng per kilogram of body weight.

36) The method of any one of clauses 25 to 33 wherein the composition is administered to a patient in an effective dose, wherein the effective dose ranges from about 1 µg to about 100 µg per kilogram of body weight.

37) The method of any one of clauses 25 to 33 wherein the composition is administered to a patient in an effective dose, of any one of clauses 25 to 36 wherein the kinase inhibiting peptide has at least 90% sequence identity to YARAAARQARAKALARQLGVAA.

38) The method of any one of clauses 25 to 33 wherein kinase inhibiting peptide has at least 90% sequence identity to YARAAARQARAKALNRQLGVA.

39) The method of any one of clauses 25 to 33 wherein the kinase inhibiting peptide has at least 90% sequence identity to FAKLAARLYRKALARQLGVAA.

40) The method of any one of clauses 25 to 33 wherein the kinase inhibiting peptide has at least 90% sequence identity to KAFAKLAARLYRKALARQLGVAA.

41) The method of any one of clauses 25 to 33 wherein the kinase inhibiting peptide has at least 90% sequence identity to HRRIKAWLKKIKALARQLGVAA.

42) The method of any one of clauses 25 to 33 wherein the kinase inhibiting peptide has at least 90% sequence identity to YARAAARQARAKALNRQLAVAA.

43) The method of any one of clauses 25 to 33 wherein the kinase inhibiting peptide has at least 90% sequence identity to YARAAARQARAKALNRQLAVA.

44) The method of any one of clauses 25 to 43 wherein the at least one copolymerized anionic monomer is 2-acrylamido-2-methyl-1-propanesulfonic acid, and wherein the at least one additional copolymerized monomer is N-isopropylacrylamide.

45) The method of any one of clauses 25 to 44 wherein the at least one copolymerized anionic monomer is 2-acrylamido-2-methyl-1-propanesulfonic acid, wherein the at least one additional copolymerized monomer is N-isopropylacrylamide, and wherein the kinase inhibiting peptide is KAFAKLAARLYRKALARQLGVAA.

46) The method of any one of clauses 25 to 45 wherein the at least one copolymerized anionic monomer is 2-acrylamido-2-methyl-1-propanesulfonic acid, wherein the at least one additional copolymerized monomer is N-isopropylacrylamide, wherein the crosslinker is N,O-dimethacryloylhydroxylamine, and wherein the kinase inhibiting peptide is KAFAKLAARLYRKALARQLGVAA.

47) The method of any one of clauses 25 to 46 wherein the at least one additional copolymerized monomer and the copolymerized anionic monomer are present in the composition at a ratio selected from the group consisting of about 5:1, about 8:1, about 9:1, about 10:1, about 11:1, about 12:1, and about 15:1.

48) The method of any one of clauses 25 to 47 wherein the at least one additional copolymerized monomer and the copolymerized anionic monomer are present in the composition at a ratio of about 10:1.

49) The composition or method of any one of the preceding clauses wherein the anionic monomer is a sulfonic monomer.

50) The composition or method of any one of the preceding clauses wherein the composition is a pharmaceutical composition.

DETAILED DESCRIPTION OF THE ILLUSTRATIVE EMBODIMENTS

Figure 1:
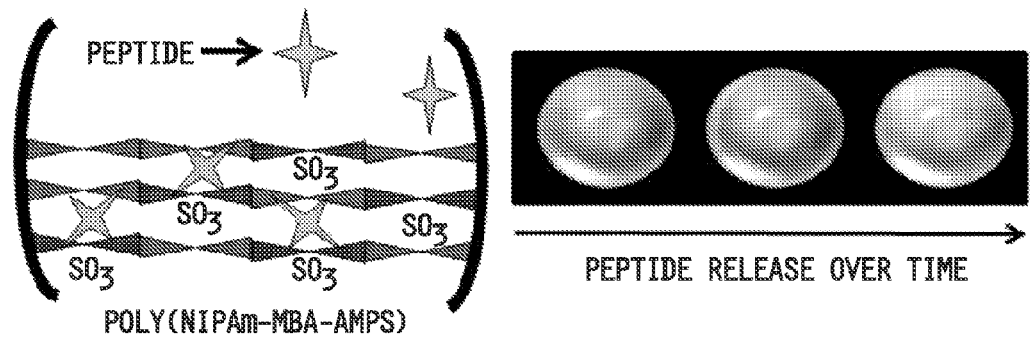
FIG. 1. Schematic representation of peptide release over time.

Several embodiments of the invention are described by the following enumerated clauses and each of the embodiments described in this Detailed Description section of the application apply to each of the following embodiments:

1) A composition comprising at least one kinase inhibiting peptide incorporated with a nanoparticle, wherein the nanoparticle comprises at least one copolymerized monomer having an anionic side chain and at least one additional copolymerized monomer.

2) The composition of clause 1 wherein the kinase inhibiting peptide is an MK2 inhibitor peptide.

3) The composition of any one of clauses 1 and 2 wherein the amino acid sequence of the kinase inhibiting peptide has at least 90% sequence identity to a peptide selected from the group consisting of YARAAARQARAKALARQLGVAA, YARAAARQARAKALNRQLGVA, FAKLAARLYRKA-LARQLGVAA, KAFAKLAARLYRKALARQLGVAA, HRRIKAWLKKIKALARQLGVAA, YARAAAR-QARAKALNRQLAVAA, and YARAAARQARAKALN-RQLAVA.

4) The composition of any one of clause 1 to 3 wherein the at least one copolymerized anionic monomer is 2-acrylamido-2-methyl-1-propanesulfonic acid.

5) The composition of any one of clauses 1 to 4 wherein the at least one additional copolymerized monomer is N-isopropylacrylamide.

6) The composition of any one of clauses 1 to 5 further comprising a crosslinker.

7) The composition of clause 6 wherein the crosslinker is selected from the group consisting of N,O-dimethacryloylhydroxylamine, divinyl adipate, N,N-Bis(acryloyl)cystamine, and N,N'-methylenebisacrylamide.

8) The composition of any one of clauses 1 to 6 further comprising a pharmaceutically acceptable carrier.

9) The composition of clause 8 wherein the carrier is a liquid carrier and is selected from the group consisting of saline, glucose, alcohols, glycols, esters, amides, and a combination thereof.

10) An effective dose of the composition of any of clauses 1 to 9 for administration to a patient, wherein the effective dose ranges from about 1 ng to about 1 mg per kilogram of body weight.

11) An effective dose of the composition of any of clauses 1 to 9 for administration to a patient, wherein the effective dose ranges from about 1 pg to about 10 ng per kilogram of body weight.

12) An effective dose of the composition of any of clauses 1 to 9 for administration to a patient, wherein the effective dose ranges from about 1 µg to about 100 µg per kilogram of body weight.

13) The composition of any one of clauses 1 to 12 wherein the kinase inhibiting peptide has at least 90% sequence identity to YARAAARQARAKALARQLGVAA.

14) The composition of any one of clauses 1 to 12 wherein the kinase inhibiting peptide has at least 90% sequence identity to YARAAARQARAKALNRQLGVA.

15) The composition of any one of clauses 1 to 12 wherein the kinase inhibiting peptide has at least 90% sequence identity to FAKLAARLYRKALARQLGVAA.

16) The composition of any one of clauses 1 to 12 wherein the kinase inhibiting peptide has at least 90% sequence identity to KAFAKLAARLYRKALARQLGVAA.

17) The composition of any one of clauses 1 to 12 wherein the kinase inhibiting peptide has at least 90% sequence identity to HRRIKAWLKKIKALARQLGVAA.

18) The composition of any one of clauses 1 to 12 wherein the kinase inhibiting peptide has at least 90% sequence identity to YARAAARQARAKALNRQLAVAA.

19) The composition of any one of clauses 1 to 12 wherein the kinase inhibiting peptide has at least 90% sequence identity to YARAAARQARAKALNRQLAVA.

20) The composition of any one of clauses 1 to 19 wherein the at least one copolymerized anionic monomer is 2-acrylamido-2-methyl-1-propanesulfonic acid, and wherein the at least one additional copolymerized monomer is N-isopropylacrylamide.

21) The composition of any one of clauses 1 to 20 wherein the at least one copolymerized anionic monomer is 2-acrylamido-2-methyl-1-propanesulfonic acid, wherein the at least one additional copolymerized monomer is N-isopropylacrylamide, and wherein the kinase inhibiting peptide is KAFAKLAARLYRKALARQLGVAA.

22) The composition of any one of clauses 1 to 21 wherein the at least one copolymerized anionic monomer is 2-acrylamido-2-methyl-1-propanesulfonic acid, wherein the at least one additional copolymerized monomer is N-isopropylacrylamide, wherein the crosslinker is N,O-dimethacryloylhydroxylamine, and wherein the kinase inhibiting peptide is KAFAKLAARLYRKALARQLGVAA.

23) The composition of any one of clauses 1 to 22 wherein the at least one additional copolymerized monomer and the copolymerized anionic monomer are present in the composition at a ratio selected from the group consisting of about 5:1, about 8:1, about 9:1, about 10:1, about 11:1, about 12:1, and about 15:1.

24) The composition of any one of clauses 1 to 23 wherein the at least one additional copolymerized monomer and the copolymerized anionic monomer are present in the composition at a ratio of about 10:1.

25) A method for treating osteoarthritis, the method comprising the step of
administering a composition comprising at least one kinase inhibiting peptide incorporated with a nanoparticle, wherein the nanoparticle comprises at least one copolymerized anionic monomer and at least one additional copolymerized monomer.

26) The method of clause 25 wherein the kinase inhibiting peptide is an MK2 inhibitor peptide.

27) The method of any one of clauses 25 and 26 wherein the amino acid sequence of the kinase inhibiting peptide has at least 90% sequence identity to a peptide selected from the group consisting of YARAAARQARAKALARQLGVAA, YARAAARQARAKALNRQLGVA, FAKLAARLYRKALARQLGVAA, KAFAKLAARLYRKALARQLGVAA, HRRIKAWLKKIKALARQLGVAA, YARAAAR-QARAKALNRQLAVAA, and YARAAARQARAKALN-RQLAVA.

28) The method of any one of clause 25 to 27 wherein the at least one copolymerized sulfonic monomer is 2-acrylamido-2-methyl-1-propanesulfonic acid.

29) The method of any one of clauses 25 to 28 wherein the at least one additional copolymerized monomer is N-isopropylacrylamide.

30) The method of any one of clauses 25 to 29 wherein the nanoparticle further comprising a crosslinker.

31) The method of clause 30 wherein the crosslinker is selected from the group consisting of N,O-dimethacryloylhydroxylamine, divinyl adipate, N,N-Bis(acryloyl)cystamine, and N,N'-methylenebisacrylamide.

32) The method of any one of clauses 25 to 31 further comprising a pharmaceutically acceptable carrier.

33) The method of clause 32 wherein the carrier is a liquid carrier and is selected from the group consisting of saline, glucose, alcohols, glycols, esters, amides, and a combination thereof.

34) The method of any one of clauses 25 to 33 wherein the composition is administered to a patient in an effective dose, wherein the effective dose ranges from about 1 ng to about 1 mg per kilogram of body weight.

35) The method of any one of clauses 25 to 33 wherein the composition is administered to a patient in an effective dose, wherein the effective dose ranges from about 1 pg to about 10 ng per kilogram of body weight.

36) The method of any one of clauses 25 to 33 wherein the composition is administered to a patient in an effective dose, wherein the effective dose ranges from about 1 µg to about 100 µg per kilogram of body weight.

37) The method of any one of clauses 25 to 33 wherein the composition is administered to a patient in an effective dose, of any one of clauses 25 to 36 wherein the kinase inhibiting peptide has at least 90% sequence identity to YARAAAR-QARAKALARQLGVAA.

38) The method of any one of clauses 25 to 33 wherein the kinase inhibiting peptide has at least 90% sequence identity to YARAAARQARAKALNRQLGVA.

39) The method of any one of clauses 25 to 33 wherein the kinase inhibiting peptide has at least 90% sequence identity to FAKLAARLYRKALARQLGVAA.

40) The method of any one of clauses 25 to 33 wherein the kinase inhibiting peptide has at least 90% sequence identity to KAFAKLAARLYRKALARQLGVAA.

41) The method of any one of clauses 25 to 33 wherein the kinase inhibiting peptide has at least 90% sequence identity to HRRIKAWLKKIKALARQLGVAA.

42) The method of any one of clauses 25 to 33 wherein the kinase inhibiting peptide has at least 90% sequence identity to YARAAARQARAKALNRQLAVAA.

43) The method of any one of clauses 25 to 33 wherein the kinase inhibiting peptide has at least 90% sequence identity to YARAAARQARAKALNRQLAVA.

44) The method of any one of clauses 25 to 43 wherein the at least one copolymerized anionic monomer is 2-acrylamido-2-methyl-1-propanesulfonic acid, and wherein the at least one additional copolymerized monomer is N-isopropylacrylamide.

45) The method of any one of clauses 25 to 44 wherein the at least one copolymerized anionic monomer is 2-acrylamido-2-methyl-1-propanesulfonic acid, wherein the at least one additional copolymerized monomer is N-isopropylacrylamide, and wherein the kinase inhibiting peptide is KAFAKLAARLYRKALARQLGVAA.

46) The method of any one of clauses 25 to 45 wherein the at least one copolymerized anionic monomer is 2-acrylamido-2-methyl-1-propanesulfonic acid, wherein the at least one additional copolymerized monomer is N-isopropylacrylamide, wherein the crosslinker is N,O-dimethacryloylhydroxylamine, and wherein the kinase inhibiting peptide is KAFAKLAARLYRKALARQLGVAA.

47) The method of any one of clauses 25 to 46 wherein the at least one additional copolymerized monomer and the copolymerized anionic monomer are present in the composition at a ratio selected from the group consisting of about 5:1, about 8:1, about 9:1, about 10:1, about 11:1, about 12:1, and about 15:1.

48) The method of any one of clauses 25 to 47 wherein the at least one additional copolymerized monomer and the copolymerized anionic monomer are present in the composition at a ratio of about 10:1.

49) The composition or method of any one of the preceding clauses wherein the anionic monomer is a sulfonic monomer.

50) The composition or method of any one of the preceding clauses wherein the composition is a pharmaceutical composition.

In any of the various embodiments described herein, the following features may be present where applicable, providing additional embodiments of the invention. For all of the embodiments, any applicable combination of embodiments is also contemplated. Any applicable combination of the above-described embodiments in the enumerated clauses is also considered to be in accordance with the invention.

In various embodiments of the compositions and methods described herein, a nanoparticle incorporated kinase inhibiting peptide can be used. As used herein the terms "nanoparticle incorporated kinase inhibiting peptide" and "kinase inhibiting peptide(s) incorporated with a nanoparticle(s)" are used interchangeably and refer to one or more kinase inhibiting peptides incorporated with one or more nanoparticles.

A nanoparticle is understood by those of skill in the art to refer to a particle having at least one dimension of submicron size. Nanoparticles may be composed from one or more of several types of materials, for example monomers [e.g., sulfonic monomers such as sulfonic monomer is 2-acrylamido-2-methyl-1-propanesulfonic acid (AMPS)], polymers [e.g., poly(lactic-co-glycolic acid) (PLGA), poly(N-vinylcaprolactam)(PVCL), and poly(N-isopropylacrylamide)(PNIAm)], metals, semiconductors, and the like. For a review see Garg et al. (2007) *Pharmaceutical Reviews* 5(6), available at http://www.pharmainfo.net/reviews/nanoparticles-review, incorporated herein by reference.

The nanoparticles may also be composed of a combination of material types, for example, as a core/shell structure. Core/shell nanoparticles are nanostructures that have a core made of a material coated with another material. For review of core/shell nanostructures see Zhang et al. (2008) *Recent Patents on Biomedical Engineering* 1:34-42, incorporated herein by reference. Illustratively, a core/shell nanoparticle may have a core and shell comprising one or more of several types of materials, for example monomers (e.g., AMPS), polymers (e.g., PLGA, PVCL, and/or pNIPAM), metals (e.g., gold), semiconductors, and the like. In one illustrative embodiment, the core/shell nanoparticle may have a core comprising, for example, pNIPAM and a shell comprising AMPS.

In one embodiment, the nanoparticle can comprise one or more monomers and/or polymers polymerized to form the nanoparticle. For example, the nanoparticle can comprise at least one copolymerized anionic monomer (e.g., a sulfonic monomer, e.g., 2-acrylamido-2-methyl-1-propanesulfonic acid (AMPS)), and at least one additional copolymerized monomer, e.g., a thermosensitive polymer such as poly(N-isopropylacrylamide)(PNIAm), polymerized to form the nanoparticle. In one embodiment, the at least one copolymerized monomer and the copolymerized anionic (e.g., sulfonic) monomer are present in the composition at a ratio selected from the group consisting of about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 18:1, about 20:1, about 25:1, about 30:1. about 35:1, about 40:1, and about 50:1.

In one embodiment, the amount of anionic (e.g., sulfonic) monomer incorporated into the nanoparticle is about 7.5% to about 10%. In one embodiment, the amount of anionic (e.g., sulfonic) monomer incorporated into the nanoparticle is about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, or about 9% to about 10%. In another embodiment, the amount of anionic (e.g., sulfonic) monomer incorporated into the nanoparticle is about 0.5% to about 5%, about 1% to about 5%, about 1.5% to about 5%, about 2% to about 5%, about 2.5% to about 5%, about 5% to about 8%, about 6% to about 8%, or about 2.5% to about 7.5%. In another embodiment, the amount of anionic (e.g., sulfonic) monomer incorporated into the nanoparticle is about 0.5%, about 2.5%, about 5%, about 7.5%, about 10%, about 12%, or about 15%.

As used herein an anionic monomer refers to a monomer comprising a group that can be ionized to form an anion. Typical groups include, but are not limited to, carboxylic acids, sulfonic acids, sulfates, phosphonic acids, and phophates. Illustrative examples of anionic monomers include acrylic acid, methacrylic acid, itaconic acid, fumaric acid, crotonic acid, mono-ester derivatives of diacids, such as monomethyl itaconate, monomethyl fumarate, and monobutyl fumarate acrylamidealkylalkane sulfonic acids (e.g. 2-acrylamido-2-methyl-1-propane sulfonic acid), maleic acid, maleic acid monoesters, sulfoethyl(meth)acrylate, sodium styrene sulfonate, vinyl sulfonic acids, and the like, and alkali metal salts or ammonium salts thereof.

Illustrative examples of phosphorus acid containing monomers include allyl phosphate; mono- or diphosphate of bis(hydroxymethyl)fumarate, 2-phosphoethyl(meth)acrylate, 2-phosphopropyl(meth)acrylate, 3-phosphopropyl (meth)acrylate, phosphobutyl(meth)acrylate, and 3-phospho-2-hydroxypropyl(meth)acrylate. Additionally illustrative examples include phosphoalkyl crotonates, phosphoalkyl maleates, phosphoalkyl fumarates, phosphodialkyl (meth)acrylates, phosphodialkyl crotonates, and allyl phosphate can all be used. Additional illustrative examples of phosphorus acid containing monomers are vinyl phosphonic acid, allyl phosphonic acid, 2-acrylamido-2-methylpropanephosphinic acid, α-phosphonostyrene, and 2-methylacrylamido-2-methylpropanephosphinic acid. It is understood that the each of the forgoing examples include the alkali metal salts or ammonium salts thereof.

In one embodiment, the nanoparticle further comprises a crosslinker. In one embodiment, the crosslinker is a degradable crosslinker. In another embodiment, the crosslinker is selected from the group consisting of collagenase sensitive crosslinkers, hydrolytically degradable crosslinkers [e.g., N,O-dimethacryloylhydroxylamine (DMHA)], and the like. In another embodiment, the crosslinker is selected from the group consisting of ethylene dimethacrylate (EDMA), N,O-dimethacryloylhydroxylamine (DMHA), divinyl adipate, N,N-Bis(acryloyl)cystamine, and N,N'-methylenebisacrylamide (MBA). In another embodiment, the crosslinker composition can be combinations of any of these crosslinkers, including the combinations of one or more degradable crosslinker with one or more non-degradable crosslinker. In one embodiment, the amount of crosslinker in the nanoparticle is about 0.5 mole %, 1.0 mole %, 1.5 mole %, 2.0 mole %, 2.5 mole %, 3.0 mole %, 3.5 mole %, 4.0 mole %, 4.5 mole %, 5.0 mole %, 5.5 mole %, 7.5 mole %, and 10 mole %. In another embodiment, the amount of crosslinker in the nanoparticle can be from about 0.5 to about 5.0 mole %, 1.0 to about 5.0 mole %, 1.5 to about 5.0 mole %, 2.0 to about 5.0 mole %, 2.5 to about 5.0 mole %, 3.0 to about 5.0 mole %, 3.5 to about 5.0 mole %, 4.0 to about 5.0 mole %, or 4.5 to about 5.0 mole %.

In one embodiment, the nanoparticles described herein can have at least one dimension of about 1 nm to about 700 nm, about 1 nm to about 500 nm, about 1 nm to about 250 nm, about 100 nm to about 700 nm, about 100 nm to about 500 nm, about 100 to about 250 nm, about 250 to about 700 nm, about 250 to about 500 nm, or about 500 nm to about 700 nm. In various embodiments, the nanoparticles described herein can have at least one dimension of about 1 nm to about 100 nm, about 1 nm to about 10 nm, about 1 nm to about 20 nm, about 1 nm to about 30 nm, about 1 nm to about 40 nm, about 1 nm to about 50 nm, about 1 nm to about 60 nm, about 1 nm to about 70 nm, about 1 nm to about 80 nm, or about 1 nm to about 90 nm. In various embodiments, the nanoparticles described herein can have at least one dimension of about 30 nm to about 100 nm, about 40 nm to about 100 nm, about 50 nm to about 100 nm, about 60 nm to about 100 nm, about 20 nm to about 80 nm, about 30 nm to about 50 nm, or about 20 nm to about 50 nm. These various nanoparticle size ranges are also contemplated where the term "about" is not included.

In one illustrative embodiment, the nanoparticle is coupled to a "stabilizer." A stabilizer, for example, can inhibit or can prevent aggregation of the nanoparticles. Illustrative examples of stabilizers include, but are not limited to, a polyethylene glycol (PEG), a dextran, a peptide, an alkane-thiol, and an oligonucleotide-thiol. Peptide stabilizers, for example, those having the amino acid sequence CALNN and its derivatives, are described by Levi at el. (2004) *J. Am. Chem. Soc.* 126: 10076-10084, incorporated herein by reference. Alkane-thiols and oligonucleotide-thiols are described by Jans et al. (2010) *Nanotechnology* 21: 1-8 and Cardenas et al. (2006) *Langmuir* 22: 3294-3299, respectively, each of which is incorporated herein by reference. The molecular weight of the stabilizer may be varied according to the size of the coupled polypeptides to effectively maintain stability of the nanoparticle with minimal interference in specific binding of the polypeptide to its target.

In one embodiment, a kinase inhibiting peptide is provided, wherein the kinase inhibiting peptide comprises a sequence according to the general Formula I:

Z1-X1-X2-X3-X4 X5-X6-X7-X8-X9-X10-Z2 wherein Z1 and Z2 are independently absent or are transduction domains;
X1 is KA;
X2 is L;
X3 is selected from the group consisting of V, L, I, A, G, Q, N, S, T, and C;
X4 is R;
X5 is Q;
X6 is L;
X7 is selected from the group consisting of S, A, C, T, and G;
X8 is V;
X9 is A; and
X10 is A or is absent.

In one embodiment, the transduction domain is selected from the group consisting of YARAAARQARA, FAKLAARLYR, KAFAKLAARLYR, YGRKKKRRQRRR, WLRRIKAWLRRI, and HRRIKAWLKKI.

In one embodiment, a kinase inhibiting peptide is provided wherein the amino acid sequence is the sequence according to the general Formula I above, and wherein the sequence is selected from the group consisting of YARAAARQARAKALARQLGVAA, YARAAARQARAKALNRQLGVA, FAKLAARLYRKALARQLGVAA, KAFAKLAARLYRKALARQLGVAA, HRRIKAWLKKIKALARQLGVAA, YARAAARQARAKALNRQLAVAA, and YARAAARQARAKALNRQLAVA.

In one embodiment, the kinase inhibiting peptides comprise an amino acid sequence selected from the group consisting of YARAAARQARAKALARQLGVAA, YARAAARQARAKALNRQLGVA, FAKLAARLYRKALARQLGVAA, KAFAKLAARLYRKALARQLGVAA, HRRIKAWLKKIKALARQLGVAA, YARAAARQARAKALNRQLAVAA, YARAAARQARAKALNRQLAVA, or an amino acid sequence with 80%, 85%, 90%, 95%, or 98% homology to any of these seven amino acid sequences. In one embodiment, the kinase inhibiting peptide inhibits a mitogen-activated protein kinase-activated protein kinase 2 (MK2).

Conservative and/or nonconservative amino acid substitutions are contemplated for all of the above-described peptides. Non-conservative substitutions are possible provided that these do not excessively affect the kinase inhibiting activity of the peptide.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in TABLE 1.

TABLE 1

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |

TABLE 1-continued

| For Amino Acid | Replace With |
| --- | --- |
| Valine | D-Val, Leu, D-Leu, Ile, D-Ile, Met, D-Met |

In one embodiment, the kinase inhibiting peptide is synthesized according to solid phase peptide synthesis protocols that are well-known by persons of skill in the art. In one embodiment, a peptide precursor is synthesized on a solid support according to the well-known Fmoc protocol, cleaved from the support with trifluoroacetic acid and purified by chromatography according to methods known to persons skilled in the art.

In another embodiment the synthetic peptide is synthesized utilizing the methods of biotechnology that are well known to persons skilled in the art. In one embodiment a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium according to methods known by persons skilled in the art (e.g., by affinity purification). Recombinant DNA technology methods are described in Sambrook et al., "Molecular Cloning: A Laboratory Manual", 3rd Edition, Cold Spring Harbor Laboratory Press, (2001), incorporated herein by reference, and are well-known to the skilled artisan.

In one embodiment, the nanoparticle incorporated kinase inhibiting peptide described herein can be used to target and/or treat inflammatory disease states. In one embodiment, the inflammatory disease state is selected from the group consisting of scarring (e.g., hyperplastic scarring and glial scarring), adhesions, keloids, arthritis (e.g. rheumatoid arthritis and osteoarthritis), chronic obstructive pulmonary disease, atherosclerosis, intimal hyperplasia, Crohn's disease, inflammatory bowel disease, lupus erythematosus, tendonitis, psoriasis, gliosis, type II diabetes mellitus, type I diabetes mellitus, Alzheimer's disease, and inflammation.

In one embodiment, the nanoparticle is loaded with the kinase inhibiting peptide at about 5% w/w to about 50% w/w, about 5% w/w to about 10% w/w, about 5% w/w to about 20% w/w, about 5% w/w to about 30% w/w, about 7.5% w/w to about 15% w/w, about 7.5 w/w to about 30% w/w, about 15% w/w to about 50% w/w, about 20% w/w to about 30% w/w, or about 20% w/w to about 50% w/w of the peptide. In these embodiments, "w/w" denotes "weight/weight".

In any of the embodiments described herein, the nanoparticle incorporated kinase inhibiting peptides can be administered alone or in combination with suitable pharmaceutical carriers or diluents. Diluent or carrier ingredients used in the compositions containing kinase inhibiting peptides incorporated with nanoparticles can be selected so that they do not diminish the desired effects of the nanoparticle incorporated kinase inhibiting peptides. Examples of suitable dosage forms include aqueous solutions of the nanoparticle incorporated kinase inhibiting peptide incorporated with nanoparticles, for example, a solution in isotonic saline, 5% glucose or other well-known pharmaceutically acceptable liquid carriers such as alcohols, glycols, esters and amides.

"Carrier" is used herein to describe any ingredient other than the active component(s) in a formulation. The choice of carrier will to a large extent depend on factors such as the particular mode of administration, the effect of the carrier on solubility and stability, and the nature of the dosage form. In one illustrative aspect, the carrier is a liquid carrier. In one illustrative aspect, the liquid carrier is a pharmaceutically acceptable carrier.

"Pharmaceutically acceptable" as used in this application, for example, with reference to salts and formulation components such as carriers, includes "veterinarily acceptable", and thus includes both human and animal applications independently. For example, a "patient" as referred to herein can be a human patient or a veterinary patient, such as a domesticated animal (e.g., a pet).

Pharmaceutically acceptable salts, and common methodologies for preparing pharmaceutically acceptable salts, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. A preferred salt is the hydrochloride salt.

The compositions described herein and their salts may be formulated as pharmaceutical compositions for systemic administration. Such pharmaceutical compositions and processes for making the same are known in the art for both humans and non-human mammals. See, e.g., REMINGTON: THE SCIENCE AND PRACTICE OF PHARMACY, (1995) A. Gennaro, et al., eds., 19th ed., Mack Publishing Co. Additional active ingredients may be included in the composition containing a nanoparticle incorporated kinase inhibiting peptide, or a salt thereof.

In one illustrative embodiment, pharmaceutical compositions for use with a composition comprising kinase inhibiting peptides incorporated with nanoparticles for parenteral administration comprise: a) a pharmaceutically active amount of the nanoparticle incorporated kinase inhibiting peptide; b) a pharmaceutically acceptable pH buffering agent to provide a pH in the range of about pH 4.5 to about pH 9; c) an ionic strength modifying agent in the concentration range of about 0 to about 300 millimolar; and d) water soluble viscosity modifying agent in the concentration range of about 0.25% to about 10% total formula weight or any combinations of a), b), c) and d) are provided.

In various illustrative embodiments, the pH buffering agents for use in the compositions and methods herein described are those agents known to the skilled artisan and include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES.

In another illustrative embodiment, the ionic strength modulating agents include those agents known in the art, for example, glycerin, propylene glycol, mannitol, glucose, dextrose, sorbitol, sodium chloride, potassium chloride, and other electrolytes.

Useful viscosity modulating agents include but are not limited to, ionic and nonionic water soluble polymers; crosslinked acrylic acid polymers such as the "carbomer" family of polymers, e.g., carboxypolyalkylenes that may be obtained commercially under the Carbopol® trademark; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; gums such as tragacanth and xanthan gum; sodium alginate; gelatin, hyaluronic acid and salts thereof, chitosans, gellans or any combination thereof. Typically, non-acidic viscosity enhancing agents, such as a neutral or a basic agent are employed in order to facilitate achieving the desired pH of the formulation.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

In one embodiment, the solubility of the nanoparticle incorporated kinase inhibiting polypeptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a nanoparticle incorporated kinase inhibiting peptide may be formulated as a solid, semi-solid, or thixotropic liquid for administration as an implanted depot providing modified release of the active compound.

In other embodiments, nanoparticle incorporated kinase inhibiting peptides and compositions containing them can be administered topically. A variety of dose forms and bases can be applied to the topical preparations, such as an ointment, cream, gel, gel ointment, plaster (e.g. cataplasm, poultice), solution, powders, and the like. These preparations may be prepared by any conventional method with conventional pharmaceutically acceptable carriers or diluents as described below.

For example, vaseline, higher alcohols, beeswax, vegetable oils, polyethylene glycol, etc. can be used. In the preparation of a cream formulation, fats and oils, waxes, higher fatty acids, higher alcohols, fatty acid esters, purified water, emulsifying agents etc. can be used. In the preparation of gel formulations, conventional gelling materials such as polyacrylates (e.g. sodium polyacrylate), hydroxypropyl cellulose, hydroxypropyl methyl cellulose, polyvinyl alcohol, polyvinylpyrrolidone, purified water, lower alcohols, polyhydric alcohols, polyethylene glycol, and the like are used. In the preparation of a gel ointment preparation, an emulsifying agent (preferably nonionic surfactants), an oily substance (e.g. liquid paraffin, triglycerides, and the like), etc. are used in addition to the gelling materials as mentioned above. A plaster such as cataplasm or poultice can be prepared by spreading a gel preparation as mentioned above onto a support (e.g. fabrics, non-woven fabrics). In addition to the above-mentioned ingredients, paraffins, squalane, lanolin, cholesterol esters, higher fatty acid esters, and the like may optionally be used. Moreover, antioxidants such as BHA, BHT, propyl gallate, pyrogallol, tocopherol, etc. may also be incorporated. In addition to the above-mentioned preparations and components, there may optionally be used any other conventional formulations for incorporation with any other additives.

In various embodiments, the dosage of the nanoparticle incorporated kinase inhibiting peptides can vary significantly depending on the patient condition, or the disease state being treated (e.g., arthritis), the route of administration and tissue distribution, and the possibility of co-usage of other therapeutic treatments. The effective amount to be administered to a patient is based on body surface area, patient weight or mass, and physician assessment of patient condition.

Suitable dosages of the nanoparticle incorporated kinase inhibiting peptides can be determined by standard methods, for example by establishing dose-response curves in laboratory animal models or in humans in clinical trials. Illustratively, suitable dosages of nanoparticle incorporated kinase inhibiting peptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 µg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

Exemplary of tissues that may be targeted in accordance with the methods and compositions described herein include submucosa tissues (e.g., intestinal, urinary bladder tissue, and stomach tissue), collagen, pericardial tissue, skin tissue, bone, cartilage, tendon, and other connective tissues of any animal.

In one embodiment, the compositions described herein can be used for targeted drug delivery (e.g., to target drugs to tissues using the kinase inhibiting polypeptide as the targeting agent). For example, the compositions can be used for targeted delivery of drugs to specific tissues, and further to increase solubility of drugs under physiological conditions. Solubility limits have prevented the use of numerous effective drugs. However, solubility problems can be overcome by the use of nanoparticles, in which the insoluble compound is encapsulated. In other embodiments, the nanoparticles can be used to control drug release using engineered nanoparticles with specifically designed geometries and degradation profiles, making possible the release of effective drug doses over long periods of time.

Peptides can be incorporated with or coupled to nanoparticles by employing a variety of chemistries, for example, such as those described in Bioconjugate Techniques (Greg T. Hermanson, Academic Press; 2 edition (May 2, 2008)), incorporated herein by reference, or as described in the examples in this application.

For purposes of this specification and appended claims, unless otherwise indicated, all numbers expressing quantities, percentages or proportions, and other numerical values used in the specification and claims, are understood as being modified in all instances by the term "about." Accordingly, unless indicated to the contrary, the numerical parameters set forth in the following specification and attached claims are approximations that may vary depending upon the desired properties sought to be obtained by the present invention.

In another embodiment, the compositions and methods described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Example 1

Chemicals

N-isopropylacrylamide (NIPAm) was purchased from Polysciences Inc. (Warrington, Pa., USA). N,N'-methylenebisacrylamide (MBA), sodium dodecyl sulfate (SDS; 10% w/v in water), 2-acrylamido-2-methyl-1-propanesulfonic acid (AMPSA), and potassium persulfate were acquired from Sigma-Aldrich (St. Louis, Mo., USA). NIPAm, MBA, and AMPSA were stored under nitrogen at 4° C. All water used in synthesis, dialysis, and testing was treated by a MilliQ system (Millipore, Billerica, Mass., USA; 18.2 MΩ·cm resistivity).

Example 2

Nanogel Synthesis

NIPAm-containing nanogels were synthesized using standard precipitation polymerization. Briefly, the nanogel compositions described in Table 1 were formed by dissolving varying amounts of NIPAm, and AMPSA in 30 ml degassed MilliQ water in a three neck round bottom flask.

TABLE 1

| Molar Reactant Percentages | | | | | | |
|---|---|---|---|---|---|---|
| Reaction % AMPS | 0% | 2.5% | 5% | 7.5% | 10% | 15% |
| NIPAm | 838.7 mg | 816.4 mg | 794.1 mg | 773.2 mg | 752.3 mg | 710.4 mg |
| AMPS | 0 mg | 38.3 mg | 76.5 mg | 114.8 mg | 153.1 mg | 190.9 mg |

Then, 28.5 mg of MBA was dissolved in 10 ml of MilliQ water and 164 µl of a 10% SDS in MilliQ water solution were added, and the mixture was heated to 80° C. under nitrogen. After 30 minutes, 33.7 mg potassium persulfate, pre-dissolved in 10 ml degassed water, was added to the mixture to initiate polymerization. After 4 hours, the reaction was cooled to room temperature. Then, the mixture was dialyzed against MilliQ water for 7 days using a 15,000 MWCO membrane. Post dialysis concentrations varied between 6-15 mg/ml and were diluted or concentrated as necessary through lyophilzation and resuspension. To lyophilize nanoparticle, solutions were frozen to −80 C for 12 hours and then placed into a lyophilizer until the liquid was completely removed.

Example 3

Nanogel Characterization

Nanoparticles from three different reactions were characterized to validate repeatability of the synthesis for size and zeta (ζ) potential measurements. The hydrodynamic diameter of nanoparticles generated under each reaction condition was measured with dynamic light scattering (DLS) using a Nano-ZS90 Zetasizer (Malvern, Westborough, Mass., USA) that was calibrated with polystyrene beads. Samples in disposable polystyrene cuvettes underwent 12 measurements per sample. For static temperature measurements, samples were equilibrated at the desired temperature for 5 minutes. Temperature sweep samples were equilibrated for 2 minutes for each half-degree temperature change. Sample zeta (ζ) potentials were measured by a Nano-ZS90 Zetasizer in folded capillary cells after DLS in MilliQ water. TEM was conducted at the Purdue University Life Science Microscope facility on a FEI/Philips CM-100 Transmission Electron Microscope at 100 Kv using an uranyl acetate stain (UA) at pH 4.5. Discharged TEM sample grids were placed onto the top of a droplet of sample for 2 minutes. Then UA stain was added and samples were dried briefly before imaging at room temperature.

Effect of AMPS Addition on Particle Size

Figure 2:
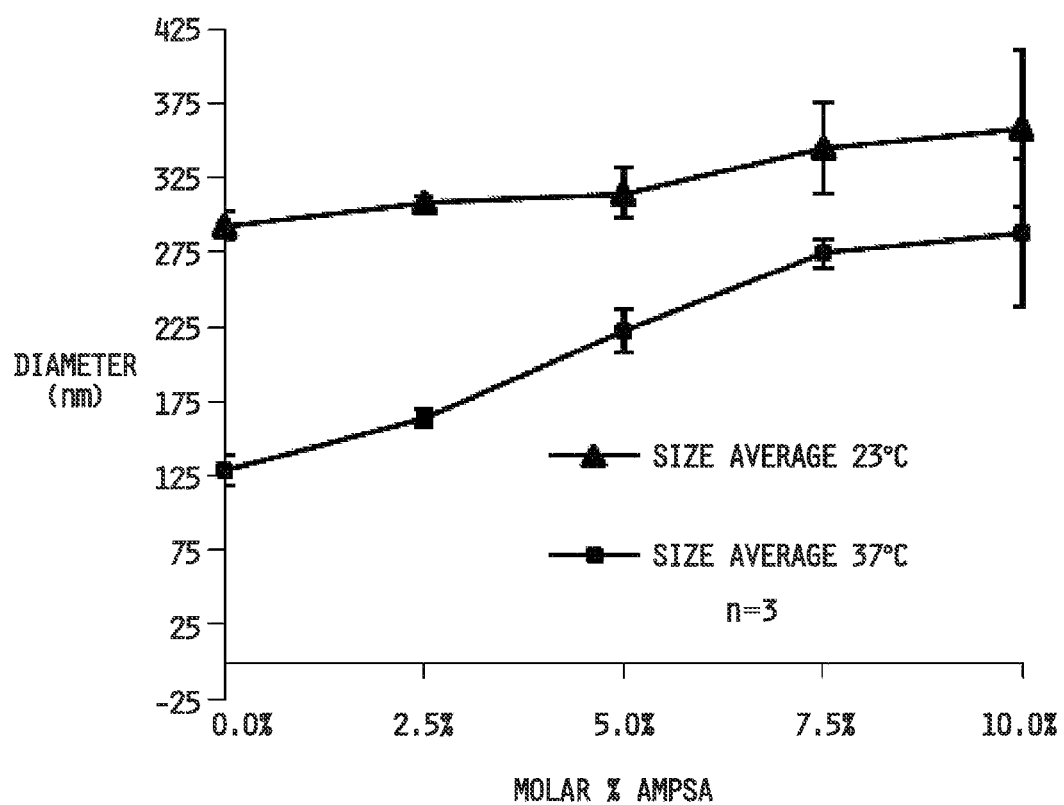
FIG. 2. Dynamic light scattering (DLS) hydrodynamic diameter measurements of poly(NIPAm-MBA-AMPS) nanoparticles at 23° C. and 37° C. n=number of separate reactions measured.

The addition of AMPS has a profound impact on the size and thermodynamic swelling of typical NIPAm systems. This allows AMPS to be used to tune the physical properties of the system. Dynamic light scattering (DLS) size measurements of nanoparticles as a function of increasing monomer reaction ratio of AMPS to NIPAm are shown in FIG. 1. This data demonstrates a general trend of increased size with increased incorporation of AMP as both 23° C. and 37° C. (FIG. 2).

Stable particle formation with the addition of 5% molar AMPS into the poly(NIPAm-MBA) reaction was observed. AMPS addition was varied to determine parameters to control charge dependent release of therapeutic peptides from these nanoparticles. Results showed increasing hydrodynamic diameter with increasing starting monomer percent of AMPS for measurements at 37° C. until an upper limit of stability between 7.5%-10% AMPS in the reaction mixture was reached. At 23° C. particle size did not significantly vary with AMPS. Particles did not degrade or aggregate when stored at 4° C. for over 18 months in MilliQ water.

Figure 3:
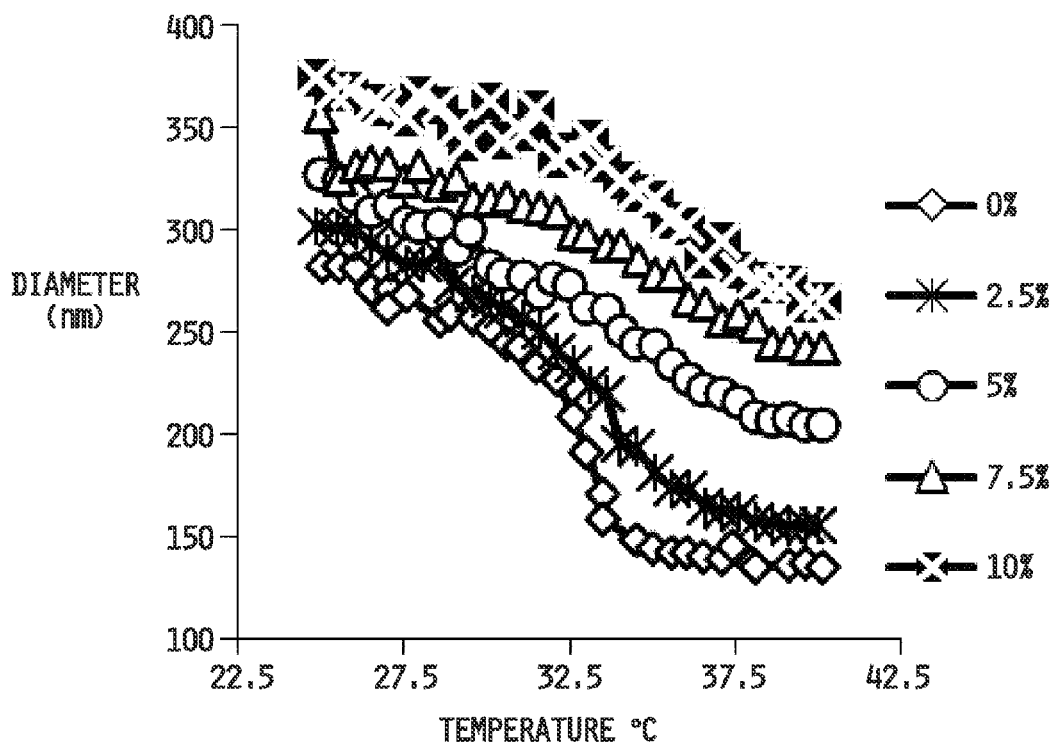
FIG. 3. DLS temperature sweep from 23° C. to 40° C. of poly(NIPAm-MBA-AMPS) nanoparticles.

The ability of poly(NIPAm-MBA-AMPS) nanoparticles to respond to temperature was maintained with the incorporation of AMPS. However, as indicated by the relative differences of particle size in FIG. 2, the thermodynamic swelling ratio was shown to decrease in magnitude with increasing AMPS incorporation presumably due to an increase in overall hydrophilicity of the NIPAm polymer. This is consistent with research demonstrating that as hydrophilic content is added to a hydrophobic polymer backbone, the effect is an increase in overall system solubility. As seen in studies using NIPAm as the primary constituent of a bulk polymer, the phase transition temperature, or lower critical solution temperature (LCST), shifts to higher temperatures as the AMPS content of the polymer increases (FIG. 3). The change in hydrodynamic diameter over a temperature sweep of 0.5° C. per 5 minutes from 25° C. to 40° C. is shown in FIG. 3. Nanoparticles synthesized from MBA-NIPAm were used as a control and were shown to have a LSCT consistent with literature around 31-33° C.

Increasing the addition of AMPS increased the LCST and the solvation energy of the copolymer leading to a reduction in swelling ratio. Specifically additions of AMPS above 5% led to swelling ratios of 1.25±0.04 as compared to a swelling ratio of 2.3±0.25 for 0% AMPS particles.

Zeta Potential Measurements

Figure 4:
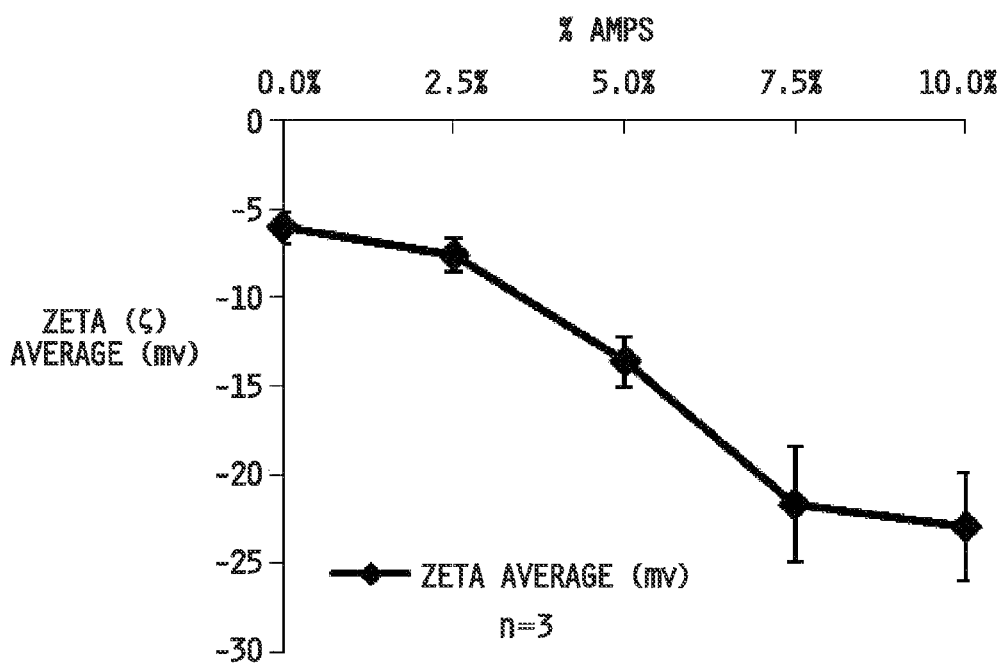
FIG. 4. Zeta potential (c) measurements of poly(NIPAm-MBA-AMPS) nanoparticles. n=number of separate reactions measured.

AMPS incorporation and colloidal stability were indirectly measured by zeta (ζ) potential in MilliQ water. FIG. 4, as a general trend, shows that zeta potential increased in magnitude with the addition of up to 10% AMPS. However there is no statistical difference between the 7.5% and 10% zeta measurements. Similarly the sizing data from FIG. 2 shows that there is no statistically relevant size difference between 7.5% and 10% particles. Also FIG. 2 shows an increase in the standard deviation of nanoparticle size with increasing AMPS. Together, these three inferences suggest the presence of an upper limit of AMPS monomer incorporation between 7.5%-10% under the reaction conditions studied and that the composition of nanoparticles formed with 7.5 and 10% AMPS in the monomer feed ratio are substantially similar. Increasing AMPS further, above 10%, inhibited particle formation.

Transmission Electron Microscopy (TEM)

Figure 5:
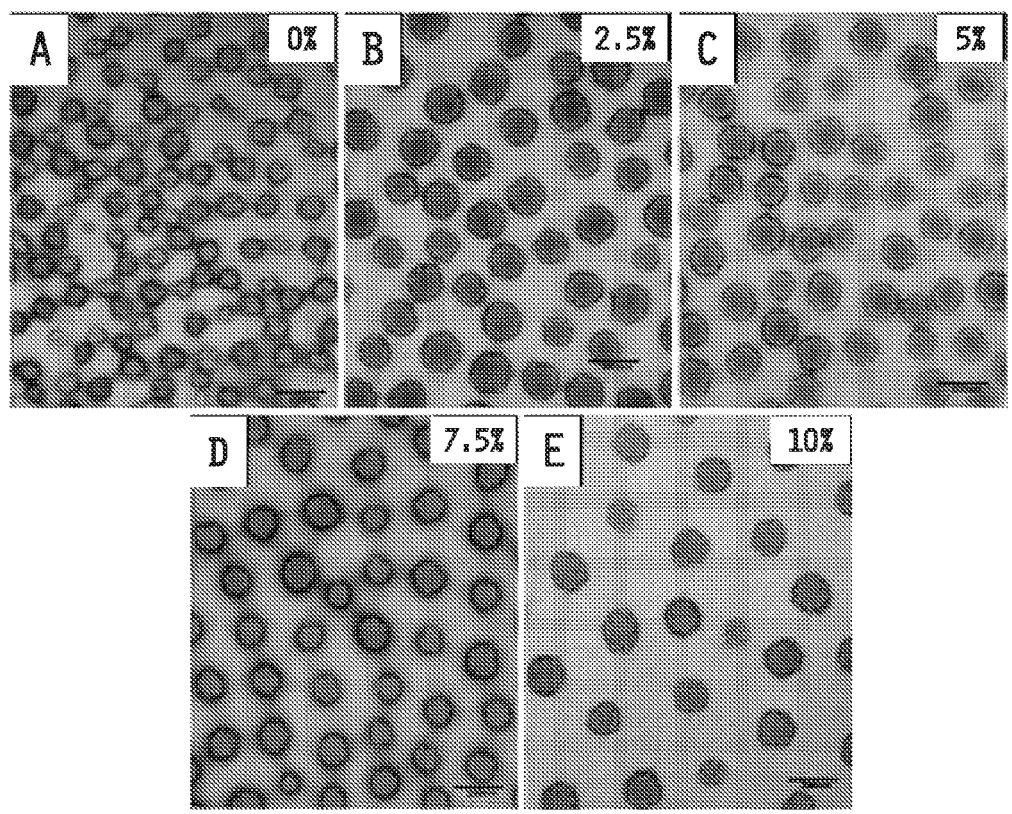
FIG. 5. TEM images of poly(NIPAm-MBA-AMPS) nanoparticles from 0% AMPS to 10% AMPS, 0%-A, 2.5%-B, 5%-C, 7.5%-D, 10%-E. Images are shown at 52 k magnification with a scale bar of 200 nm.

FIG. 5 shows TEM images of nanoparticles from reactions of increasing concentrations of AMPS (from 0% to 10%). TEM images show that particles containing AMPS are more uniform than those without AMPS. Also, zeta potential measurements, an indication of colloidal stability, size uniformity, and uniformity of spacing, were confirmed as particles with AMPS were more uniform and evenly spaced than particles without AMPS in FIG. 5A. The decreased particle diameter found using TEM as compared to DLS is due to DLS measurements being conducted in MilliQ water as compared to TEM images taken with particles stained by UA on a dried TEM plate.

Example 4

Activated Partial Thromboplastin Time

Activated partial thromboplastin time (aPTT) was measured using a Hemochron® Response whole blood coagulation system. 2 ml citrated bovine whole blood and 200 μL nanoparticles in phosphate buffered saline (PBS) pH 7.4 (1.5 mg/ml final concentration in blood) were added to Hemochron® tubes containing colloidal kaolin activating agent and 0.02% thimerosal preservative agent. PBS was calcium and magnesium free. The tubes were then measured and aPTT was recorded. The aPTT for each sample was measured in triplicate. Controls consisted of PBS without nanoparticles, a 6 mg/ml purified bovine collagen solution (Advanced Biomatrix, San Diego, Calif., USA), and 0.01 mg/ml (final concentration) heparin (Sigma Aldrich, St. Louis, Mo., USA). Measurements with heparin were stopped after 1000 seconds.

Blood Interaction Assays

As part of a preliminary assessment of utilizing poly (NIPAm-MBA-AMPS) as a blood contacting drug delivery vehicle, whole blood studies were done to determine the hemocompatibility of this system. Table 2 shows coagulation times of various treatments of AMPS nanoparticles, 100 μl/ml blood to a final concentration of 1.5 mg/ml.

TABLE 2

Blood - Nanoparticle Interaction

| | Whole Blood Coagulation Time (s) | | Normalized Whole Blood % Hemolysis | |
| --- | --- | --- | --- | --- |
| | Average (n = 3) | StDev | Average (n = 3) | StDev |
| Blood | 236 | 14.3 | — | — |
| PBS | 235 | 17.3 | 0% | 0.11% |
| 0.0% | 238 | 15.7 | −0.07% | 0.10% |

TABLE 2-continued

Blood - Nanoparticle Interaction

| | Whole Blood Coagulation Time (s) | | Normalized Whole Blood % Hemolysis | |
|---|---|---|---|---|
| | Average (n = 3) | StDev | Average (n = 3) | StDev |
| 2.5% | 234 | 11.8 | 0.44% | 0.75% |
| 5.0% | 237 | 14.9 | 1.51% | 1.40% |
| 7.5% | 227 | 7.3 | 0.00% | 0.07% |
| 10.0% | 227 | 7.2 | 0.69% | 0.20% |
| Collagen 6 mg/ml | 26 | 7.7 | — | — |
| Heparin[I] | >1000 | NA | — | — |
| Triton X-100[II] | — | — | 100% | 4.29% |

[I]Heparin concentration was .001 mg/ml
P > .05 as compared to Heparin
[II]Triton X-100 was .01% by volume
P > .05 as compared to Triton X-100

No difference in coagulation time between treatment and control (PBS and Collagen) were observed, P>0.05, showing that the nanoparticles did not affect coagulation. A negative control of a 6 mg/ml bovine collagen solution was shown to induce clotting. As a positive control, heparin was seen to inhibit coagulation. After 1000 seconds, experiments in the presence of heparin were stopped due to lack of clotting. Hemolytic assay ASTM standard protocol F756 was used to check if hemolysis occurred upon the addition of poly(NIPAm-MBA-AMPS) to the blood. Table 2 shows no statistically relevant hemolysis (P>0.05) to be present for blood incubated with the 1.5 mg/ml concentration of the nanoparticles at 37° C. for 3 hours. The data in Table 2 further indicates that poly(NIPAm-BIS-AMPS) nanoparticles are hemocompatible. This suggests that nanoparticles may be useful for a blood contacting in vivo drug release.

Example 5

Hemolysis

Hemolysis assays were performed following ASTM F756 with a BioSpec-1601 spectrophotometer (Shimadzu, Columbia, Md., USA). Determination of total blood hemoglobin was accomplished by using Drabkin's reagent and measuring the absorbance of free hemoglobin in solution at 540 nm. The total blood hemoglobin concentration was used to adjust the hemoglobin content of the blood sample to 10 mg±1 mg by adding blood and an equivalent amount of 1×PBS solution. Percent hemolysis was normalized by dividing total hemolysis determined by a 0.01% v/v of Triton X-100, subtracting the absorbance of blood only, and setting absorbance of PBS to zero. Blood, 1 ml, was incubated with 100 μl of a 1.5 mg/ml solution of the nanoparticles in PBS at 37° C. for three hours under gentle shaking. After three hours samples were centrifuged at 750 g for 15 minutes. Supernatant was removed, added 1:1 to equivalent volume of Drabkins reagent, and incubated for 15 minutes before measurement. Absorbance measurements at 540 nm were then recorded using a spectrophotometer.

Example 6

Peptide Synthesis and Purification

Therapeutic peptides for use in drug release studies were synthesized using standard 9-fluorenylmethyloxycarbonyl (FMOC) chemistry on Knorr-amine resin (Synbiosci Corp, Livermore, Calif., USA). Two amino acid coupling steps were used to attach amino acids (Synbiosci Corp, Livermore, Calif., USA). For the first coupling step, N-hydroxybenzotriazole (HoBt) and N,N'-diisopropylcarbodiimide (DIC) were incubated with amino acid and resin for 30 minutes. An second 30-minute coupling used 2-(1Hbenzotriazole-1-yl)-1,1,3,3-tetramethyluronium hexafluorophosphate (HBTU), lutidine, and amino acid to ensure high yields of pure product. After synthesis peptides were cleaved with a cocktail of trifluoroacetic acid (Sigma-Aldrich, St. Louis, Mo., USA), triisopropyl silane (TCI America, Boston, Mass., USA), ethane dithiol (Alfa Asara, Ward Hill, Mass., USA), and MilliQ water. Peptide was immediately precipitated in ether, recovered by centrifugation, solubilized in MilliQ water, and lyophilized. Peptides were purified on a FPLC AKTA Explorer (GE Healthcare, Pittsburgh, Pa., USA) with a 22/250 C18 prep-scale column (Grace Davidson, Deerfield, Ill., USA) and an acetonitrile gradient with 0.1% trifluoroacetic acid. Peptide molecular weight was confirmed by time matrix-assisted laser desorption ionization time of flight (MALDI TOF) mass spectrometry with a 4800 Plus MALDI TOF/TOF Analyzer (Applied Biosystems, Foster City, Calif., USA).

Example 7

Drug Loading & Release

In order to ensure proper drug loading, purified peptide was first dissolved in MilliQ water to create a 1 mg/ml loading solution. Then this solution was added to lyophilized nanoparticles of 0%, 5%, and 10% AMPS such that the final particle concentration in solution was 2 mg/ml. Then, the drug-nanoparticle loading solution complex was allowed to incubate for 24 hours at 4° C., to ensure particle swelling and facilitate peptide uptake in the particles, prior to centrifugation at 55,000 rpm in an Optima L-90k Ultracentrifuge (Beckman Coulter, Indianapolis, Ind., USA). Then diluent was isolated from the pellet. Both nanoparticle pellet and diluent were lyophilized for later analysis. Loaded nanoparticles were suspended in either MilliQ water or sterile PBS at pH 7.4 (Invitrogen, Grand Island, N.Y., USA) at a concentration of 0.5 mg/ml loaded particles. Measurement of free peptide released into the solution was conducted using fluorescence analysis in a Costar 96-well plate by adding 20 μl of a sample solution to 180 μl fluoraldehyde o-Phthalaldehyde (OPA) solution (Thermo Scientific, Waltham Mass., USA). Fluorescent measurements of drug release were taken at every 15 minutes for three hours, then every six hours until day two, and every 12 hours until day three. After three days samples were taken every 24 to 48 hours until day 13. A final point was taken at 21 days. To ensure that only free peptide, and not particles, was present in the measurement sample, each sample was run through a 100,000 MW cutoff membrane microcentrifuge tube (Omega, Norcross, Ga., USA) prior to fluorescent analysis. Testing also revealed no free peptide stuck to this size exclusion membrane and that the membrane completely separated out the nanoparticles from the solution (data not shown). Images of particles containing fluorescein isothiocyanate (FITC) labeled peptide were taken with an Olympus FV1000 confocal microscope.

Positively charged MAPKAP Kinase 2 (MK2) inhibiting peptide KAFAKLAARLYRKALARQLGVAA (abbreviated KAFAK), binds strongly to sulfated glycosaminoglycans through electrostatic interactions. KAFAK, a strong inhibitor of MK2, shows potential as a therapy for chronic inflammation conditions associated with MK2 mediated increases in cytokine activity such as rheumatoid arthritis. However, because of the highly non-specific nature of the CPP associated with KAFAK and the susceptibility to enzymatic degradation, delivery of these serum sensitive therapeutic peptides is difficult in vivo without a site specific injection into an arthritic joint. A controlled release vehicle with a high loading capacity is useful to maintain the therapeutic activity of KAFAK over long timescales without repeated injections. Due to the strong affinity of KAFAK for sulfated moieties, AMPS doped poly(NIPAm) nanoparticles provide a tunable loading capacity based on the amount of incorporated AMPS. NIPAm was used as the polymer backbone to ensure the high molecular weight drug KAFAK was able to efficiently diffuse into the nanoparticle cores while they are expanded below the LCST, while above the LCST at physiological conditions they remain protected from proteases. Nanoparticle loading efficiencies, as a percent of final particle weight composed of KAFAK are shown in Table 3.

TABLE 3

Drug Loading Efficiency as Percent
Drug Mass Per Loaded Particle

| Particle Composition | Mass % Drug in Each Loaded Particle after 24 hours of loading | StDev |
|---|---|---|
| 0% AMPS | 17.8% | 7.1% |
| 5% AMPS | 45.3% | 9.5% |
| 10% AMPS | 60.5% | 6.2% |

Table 3 indicates that the addition of only 5% AMPS yields roughly a 3× increase in the amount of drug loaded into the particles utilizing a passive diffusion loading method in MilliQ water over a 24-hour incubation at 4° C. Further addition of AMPS to 10% results in roughly a 4× increase over the amount of drug loaded without AMPS.

Figure 6:
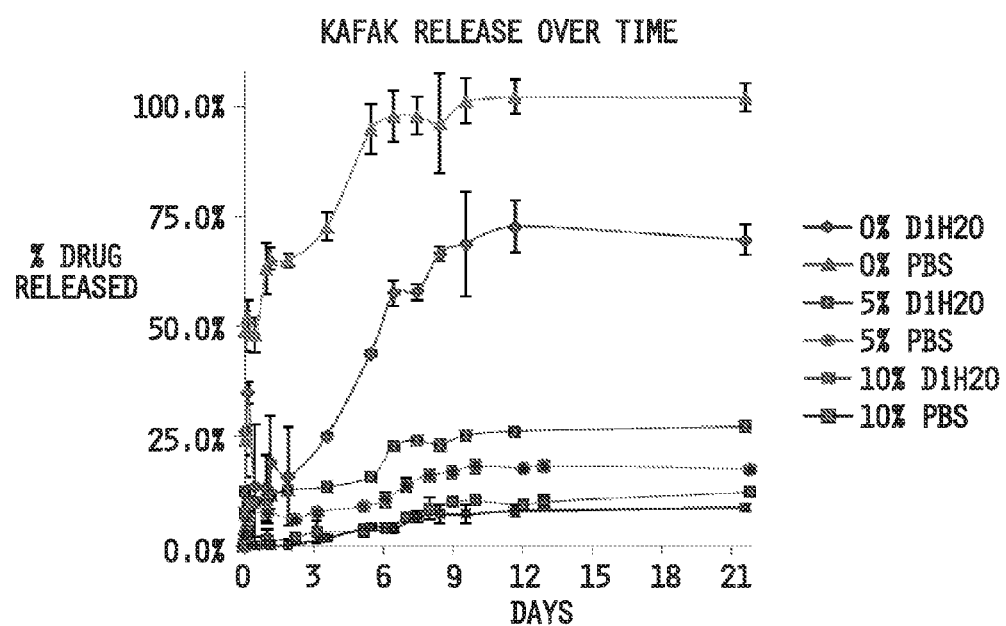
FIG. 6. Drug release profiles of KAFAK from 0%, 5%, and 10% AMPS containing particles in MilliQ water and PBS over a 21 day period at 37° C.

In order to test the electrostatic mechanism of drug binding, release studies of KAFAK were conducted in both PBS and MilliQ water to determine how particles would release bound KAFAK peptide. FIG. 6 demonstrates that electrostatic interactions do indeed have a profound effect on the drug release kinetics because particles with AMPS release much less KAFAK. Also, in every case the amount of KAFAK released in MilliQ water was significantly less than the amount of KAFAK released in a PBS environment. After 1 week 0% AMPS particles released near 100% of their drug in PBS, therefore it is reasonable to assume that the KAFAK peptide is not prohibitively encumbered by the shrunken polymer network over long time scales. However, the movement of KAFAK is retarded in the shrunken network because the amount of KAFAK loaded overnight at 4° C. requires 1 week at 37° C. to fully release. Taken together these observations demonstrate that the loading and release mechanism is driven by both physical hindrance and electrostatic interactions between KAFAK and the copolymer. After release KAFAK integrity was confirmed by MALDI TOF mass spectroscopy.

Figure 7:
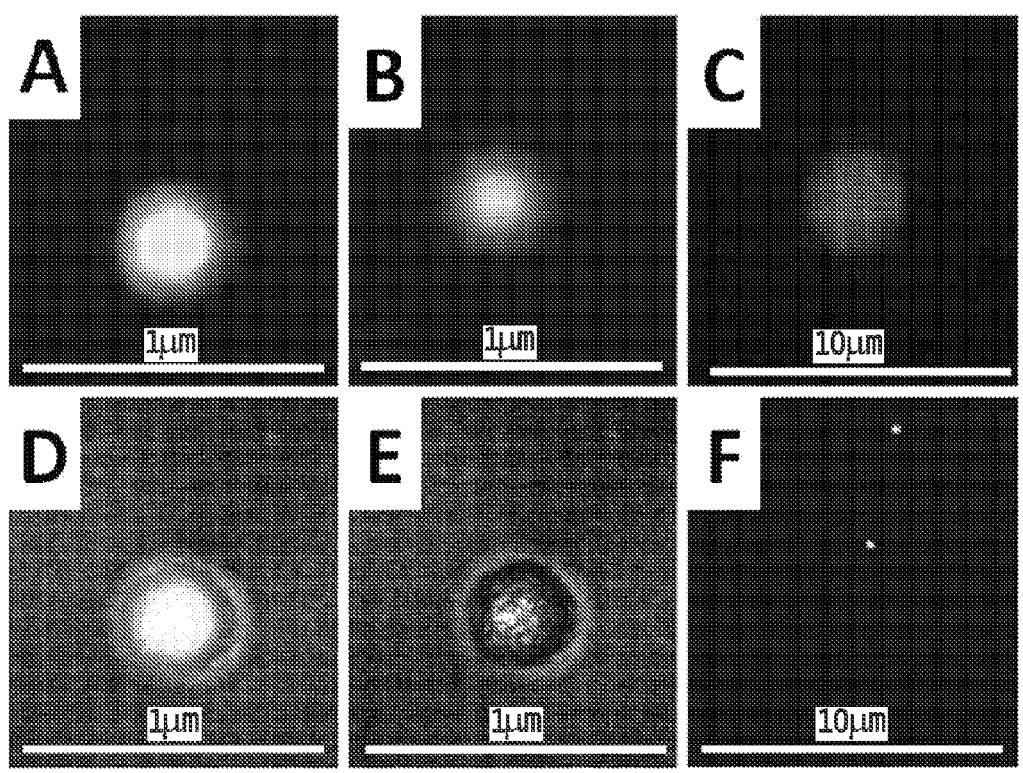
FIG. 7. Confocal image of FITC labeled KAFAK inside 5% AMPS poly(NIPAm-MBA-AMPS) nanoparticle. A is particle at time zero. B is particle after releasing for 21 days at 37° C. in PBS. C is particle after incubation in serum at 37° C. for 12 hours and incubation in 2× NaCl PBS for 24 hours at 4° C. D is an overlay of fluorescence and light image at time zero. E is the light image at time zero. F is a zoomed out image after releasing for 21 days at 37° C. in PBS.

In addition, although actual mass of drug released were comparable between the 10% AMPS particles and the 0% AMPS particles in the PBS environment, the actual percent of initially loaded KAFAK released from the 10% was only 25% compared to nearly 100% by the 0% AMPS particles. 10% particles also released ~3-7% more KAFAK than 5% particles. This is most likely due to the reduced shrinking ability of the 10% particles at 37° C. (19.4%) as compared to the 5% particles (29.3%). Enhanced particle contraction at 37° C. causes a reduction in void space between polymer strands that, combined with a high negative charge, further hindered KAFAK escape from the particle cores as shown in FIG. 7.

Example 8

Serum Studies

Samples tested include: peptide alone, serum alone, peptide in serum, and KAFAK loaded 5% AMPS nanoparticles in serum. Each sample volume also contained 0.5×PBS except when stated. Samples containing peptide initially contained 0.5 mg of peptide alone or 1.12 mg of loaded 5% AMPS particles with an equivalent amount of 0.5 mg peptide. Samples with serum were 0.5× serum and 0.5×PBS. Samples without serum were 0.5×PBS and 0.5× MilliQ water. Peptide alone, serum alone, peptide in serum, loaded nanoparticles alone, and loaded nanoparticles in serum were incubated for 12 hours at 37° C. on a shaker. After the 12 hour incubation, samples not containing nanoparticles were placed in the fridge at 4° C. for 24 hours before evaluation. Samples containing nanoparticles were centrifuged for 2 hours at room temperature at 30,000 rpm in an Optima L-90k Ultracentrifuge (Beckman Coulter, Indianapolis, Ind., USA). The nanoparticle pellet was briefly washed with MilliQ water and then resuspended in solution of 0.5×PBS and 0.5× MilliQ water. Samples were then placed in the fridge for 24 hours. Before the 24 hour nanoparticle sample was placed in the fridge to incubate, but after the pellet was dissolved, an additional amount of 0.257 molar concentration of NaCl was added to induce peptide release. This brought the final NaCl concentration to 0.342 molar or twice normal salt concentration in PBS. Additional NaCl was added to facilitate total release by introducing additional counter ions. Samples were evaluated by reverse phase chromotography on a FPLC (AKTA Explorer, GE Healthcare, Pittsburgh Pa., USA) with a 22/250 C18 prep-scale column (Grace Davidson, Deerfield, Ill., USA) and an acetonitrile gradient with 0.1% trifluoroacetic acid. Peptide was quantified by integrating the area under the peak of the FPLC. Peptide molecular weight was confirmed by time of flight MALDI mass spectrometry with a 4800 Plus MALDI TOF/TOF Analyzer (Applied Biosystems, Foster City, Calif., USA).

FIG. 7 indicates that KAFAK has released from the layer close to the surface of the poly(NIPAm-MBA-AMPS) nanoparticle after 21 days in a PBS solution but that KAFAK remained entrapped within the particle cores. Although FIG. 6 demonstrates that a significant amount of KAFAK is released from the nanoparticles containing AMPS there is still a significant amount of KAFAK locked within the particles.

To determine the ability of the poly(NIPAM-MBA-AMPS) nanoparticles to deliver KAFAK in the physiological environment, an enzymatic degradability assay in serum was conducted to determine if the peptide could be protected from degradation while within the particles in body fluids. The data in Table 4 indicates that KAFAK peptide degraded within 12 hours without a carrier to prevent degradation. Poly(NIPAM-MBA-AMPS) nanoparticles helped protect KAFAK from degradation in serum by hindering the mobility of large proteases into the core of the drug-nanoparticle complex. This results in a large amount of KAFAK continuing to be present in the nanoparticle even after 12 hours of incubation at 37° C. in serum.

TABLE 4

KAFAK Degradability Assay in Serum

| Sample | Integral of KAFAK Peak between 30-31% Acetonitrile | % Recovery |
|---|---|---|
| A) Serum Control 12 hours at 37° C. & 24 hours at 4° C. | 0 mAU*ml | 0% |
| B) KAFAK Peptide Control 12 hours at 37° C. & 24 hours at 4° C. | 593.3 mAU*ml | 100% |
| C) Serum & KAFAK Control 12 hours at 37° C. & 24 hours at 4° C. | 0 mAU*ml | 0% |
| D) Serum & Loaded Nanoparticles 12 hours at 37° C. Then purify & release 24 hours at 4° C. in 2x salt | 93.8 mAU*ml | 15.8% |
| E) Loaded Nanoparticles Control 12 hours at 37° C. Then purify & release 24 hours at 4° C. in 2x salt | 238.1 mAU*ml | 40.1% |

FIG. 6 and Table 4 both demonstrate the difficulty of separating KAFAK from the AMPS containing nanoparticles after loading has occurred. Confocal images in FIG. 7C indicate that even after incubation with serum for 12 hours and further incubation at low temperature with 2× salt concentration some KAFAK still remains bound within the core of the nanoparticle. Similarly, releasing KAFAK from nanoparticles without serum yielded only a 40.13% recovery after 24 hours at 4° C. in 2× salt. The difference in the control recovery and the 15.8% recovery from the sample containing serum and nanoparticles is likely due to either KAFAK degradation taking place at the surface of the particle, or a competitive binding of serum proteins causing increased release of surface bound KAFAK during the 12 hour incubation. Regardless of either outcome, a significant portion of KAFAK remains protected from serum degradation when loaded into poly(NIPAM-MBA-AMPS) nanoparticles. KAFAK integrity was confirmed by MALDI TOF MS.

Example 9

DMHA Synthesis

N,O-dimethacryloylhydroxylamine (DMHA) was synthesized according to methods previously reported by Ulbrich et. al. Briefly, 10.1 g of Hydroxylamine (VWR International, Radnor, Pa., USA) was dissolved in 50 ml pyridine (Mallinckrodt Chemicals, St. Louis, Mo., USA). Then 25.4 g of methacryloyl chloride (Alfa Aesar, Ward Hill, Mass., USA) was added drop wise in an ice bath. 20 minutes after methacryloyl chloride was added the reaction was then stirred at room temperature for 4 hours. The reaction was neutralized with 21 ml of concentrated HCL (Sigma-Aldrich) and dissolved in 100 ml Chloroform (Honeywell, Morristown, N.J., USA). The product was washed with four 150 ml washes of MilliQ water and the organic layer was separated and dried over anhydrous $MgSO_4$ (Mallinckrodt Chemicals). Chloroform was evaporated in a vacuum and the product was dissolved in diethyl ether (Mallinckrodt Chemicals). Heptane (VWR International) was slowly added until a crystalline compound was precipitated. Yield (24%); melting point: 54-56° C.; Purity and composition was confirmed by using a Varian Unity 300 MHz NMR spectrometer at the Purdue Core NMR Facility.

Example 10

Nanogel Synthesis

NIPAm-containing nanogels were synthesized using standard precipitation polymerization. Briefly, the nanogel compositions described in Table 5 were formed by dissolving NIPAm, MBA, and 76.5 mg (5 mole %) AMPSA in 30 ml degassed MilliQ water in a three neck round bottom flask.

TABLE 5

Nanoparticle Cross linking Composition

| Mole % DMHA | 2.5% | 5% | 4.5% | 3.5% |
|---|---|---|---|---|
| Mole % MBA | 0% | 0% | 0.5% | 1.5% |
| NIPAm | 789.8 mg | 768.5 mg | 768.5 mg | 768.5 mg |

DMHA was dissolved in 10 ml of dimethyl sulfoxide (DMSO). After addition of the DMHA 575 µl of a 10% SDS in MilliQ water solution were added, and the mixture was heated to 75° C. under nitrogen. 33.7 mg of potassium persulfate was dissolved in 10 ml degassed MilliQ water and added after 30 minutes to initiate polymerization. After 4 hours, the reaction was removed from heat and allowed to cool to room temperature. Particles were dialyzed against MilliQ water for 7 days using a 15,000 MWCO membrane. Post dialysis concentrations varied between 6-15 mg/ml and were diluted or concentrated as necessary through lyophilization and resuspension. To lyophilize nanoparticle, solutions were frozen to −80° C. for 12 hours and then placed under lyophilizer vacuum until the liquid was removed.

Example 11

Characterization of Nanogels

After calibration with polystyrene beads a Nano-ZS90 Zetasizer (Malvern, Westborough, Mass., USA) was used to measure nanoparticle diameter through dynamic light scattering (DLS). Samples were equilibrated for 2 minutes for each half-degree temperature change for a temperature sweep or 5 minutes for a static temperature measurement. Zeta (ζ) potentials were measured at 23° C. by a Nano-ZS90 Zetasizer in folded capillary cells in MilliQ water. TEM was conducted at the Purdue University Life Science Microscope facility on a FEI/Philips CM-100 Transmission Electron Microscope at 100 Kv using an uranyl acetate stain (UA) at pH 4.5. Discharged TEM sample grids were placed onto the top of a droplet of sample for 2 minutes. Then UA stain was added and samples were briefly dried before imaging at room temperature.

Figure 9:
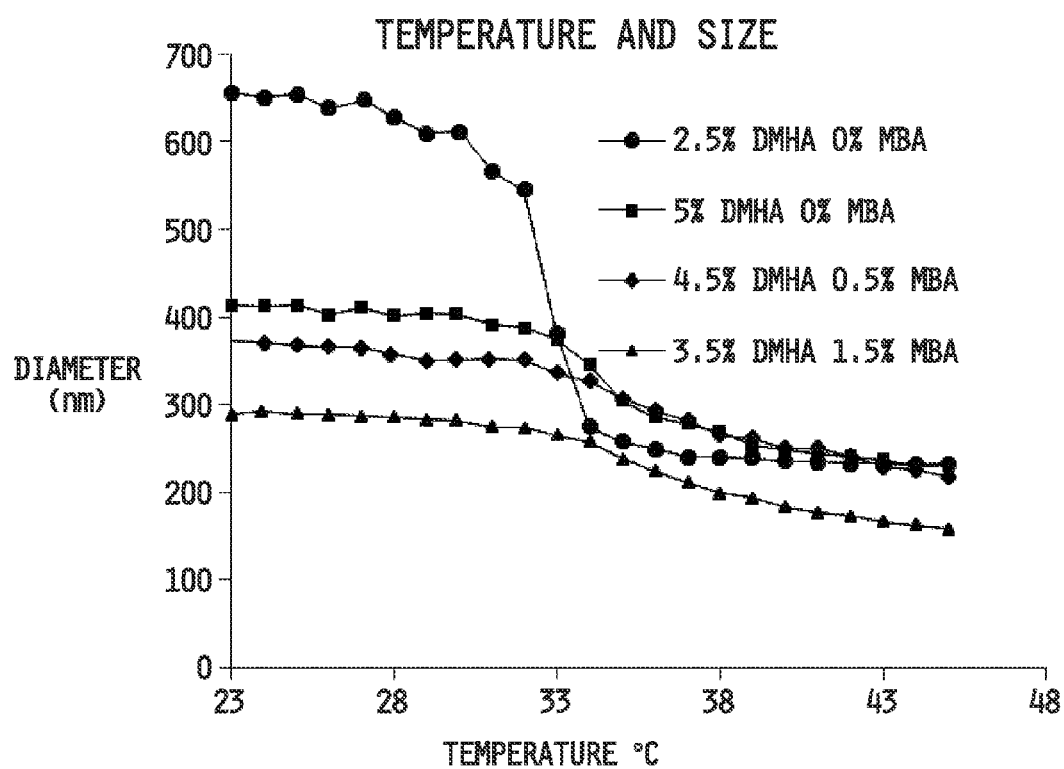
FIG. 9. Hydrodynamic diameter measurements of poly (NIPAm-AMPS) nanoparticles supplemented with varying molar percentages of DMHA and or MBA cross-linker.

Poly(NIPAm-AMPS-MBA) nanoparticles exhibit thermosensitivity similarly to traditional Poly(NIPAm-MBA) nanoparticles with swelling ratios between 1.3-1.5. Also, prior studies indicated that a composition of 5 mole % AMPS is sufficient to allow for enhanced KAFAK loading and increased colloidal stability in physiological electrolyte environments. Addition of DMHA crosslinker in place of a fraction of or all of the MBA greatly impacts nanoparticle swelling and size as indicated in FIG. 9.

Addition of DMHA in place of some or all of the MBA allowed for an increased swelling ratio as compared to formulations with MBA alone. Because the 2.5% DMHA particles contain the least amount of cross-linking, they exhibited the greatest swelling ratio.

Figure 8:
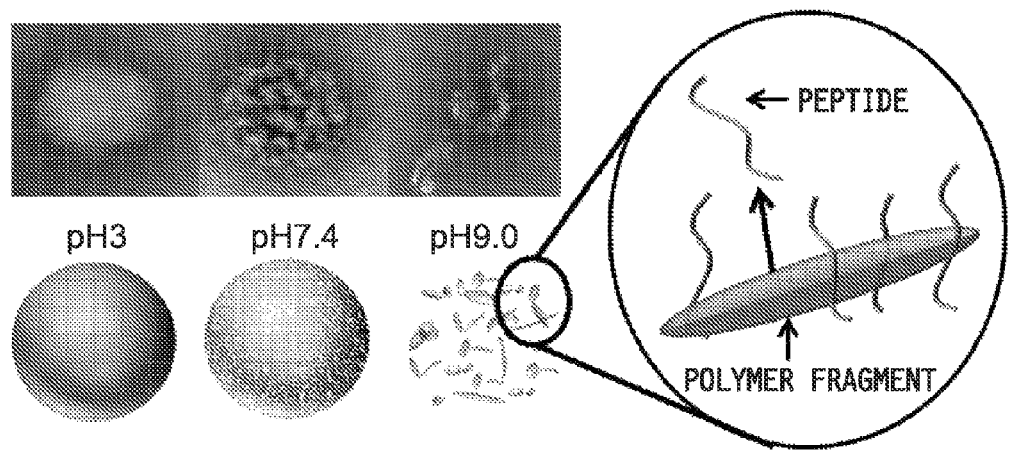
FIG. 8. Schematic representation of pH sensitive drug delivery system.
Figure 10:
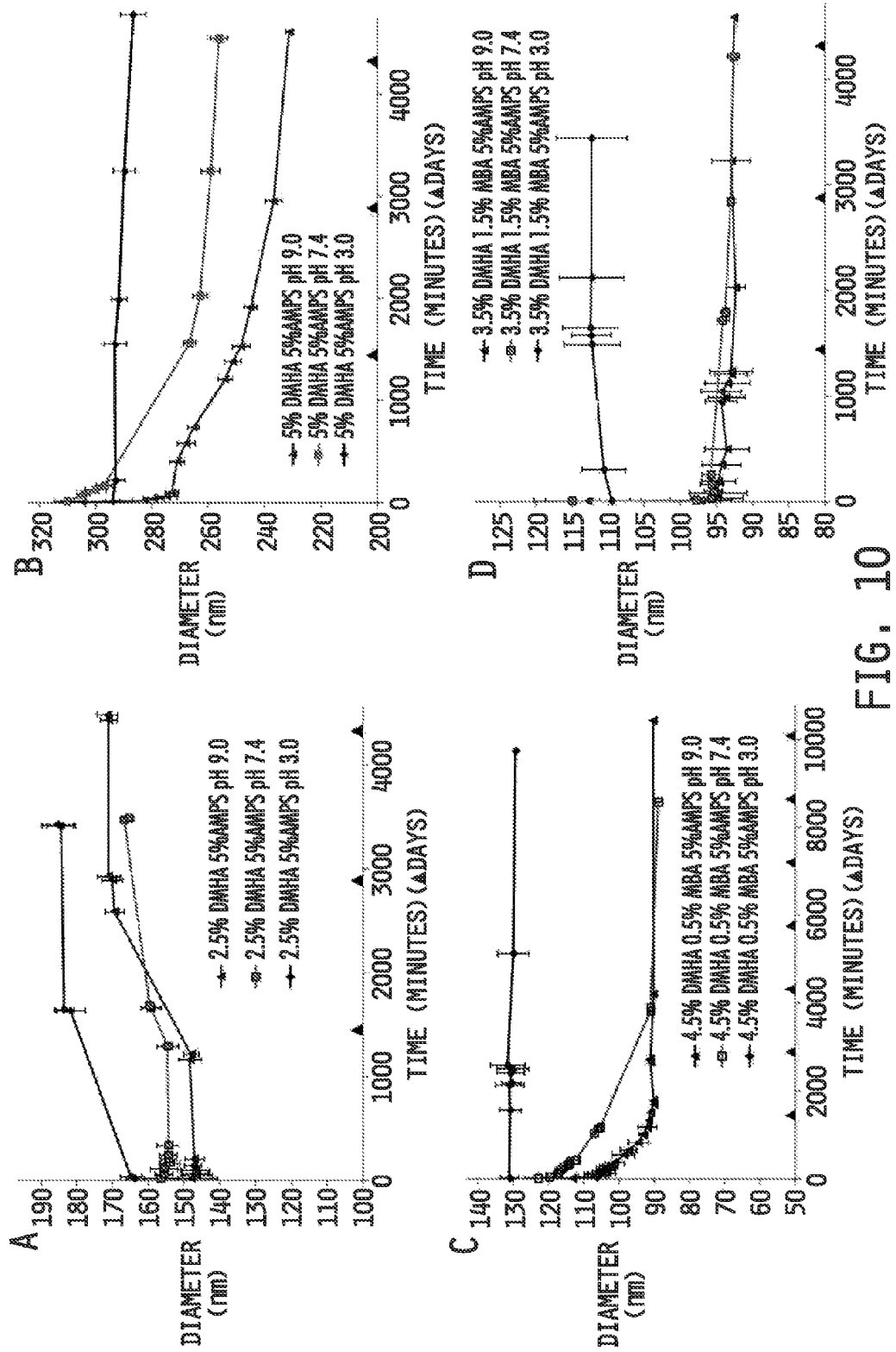
FIG. 10. Degradation over time in different pH environments of poly(NIPAM-AMPS) nanoparticles containing 5 mole % AMPS. A) 2.5 mole % DMHA. B) 5 mole % DMHA. C) 4.5 mole % DMHA 0.5 mole % MBA. D) 3.5% DMHA 1.5 mole % MBA. Samples were held at 37° C. throughout the time of degradation and measurement.

After adding the nanoparticles containing DMHA to PBS of pH 3.0, 7.4, and 9.0, a shift in particle size was observed as the DMHA crosslinks degraded over time (FIG. 8). The rate of particle swelling and shrinking was proportional to the mole % of DMHA or MBA crosslinker. FIG. 10 demonstrates that the degradation of the 5% DMHA occurred over approximately 3 days in basic pH, and appears to have occurred more rapidly at the particle surface. Particle size remained constant when particles were exposed to conditions at pH 3.0 suggesting that little degradation occurred at acidic pH. FIG. 10C shows the 4.5% DMHA 0.5% MBA nanoparticles degraded in 1-2 days, while FIG. 11D shows that the 3.5% DMHA 1.5% MBA nanoparticles degraded in 1 day. FIG. 10A suggests that the 2.5% DMHA nanoparticles degraded in just minutes, as opposed to the slower degradation seen in the more highly crosslinked systems.

Also noted in FIG. 10, the rate of DMHA breakdown, and as a result nanoparticle degradation, increased with increasing pH. As shown in FIG. 10, subtle adjustments to the crosslinking composition is a useful parameter to adjust particle size and degradation kinetics in basic environments.

Zeta Potential Measurements

Adjustments to cross-linking composition does not have a profound impact on Zeta potential for particle compositions with 5 mole % total crosslinking content according to Table 6. However, the 2.5% DMHA composition has a much lower zeta potential due to the irregular and large size of the particles at 23° C. as shown by TEM in supplementary information.

TABLE 6

Zeta Potential and Drug Loading

| Type of Cross linking | Drug Loading % | StDev | Zeta Potential (mv) | StDev |
| --- | --- | --- | --- | --- |
| 2.5% DMHA 0% MBA | 11.8% | 6.3% | −6.4 | 1.65 |
| 5% DMHA 0% MBA | 24.3% | 4.1% | −15.6 | 1.70 |
| 4.5% DMHA 0.5% MBA | 29.2% | 4.6% | −16.5 | 1.42 |
| 3.5% DMHA 1.5% MBA | 26.7% | 5.9% | −18.3 | 2.17 |

Zeta potential of particles did highly correlate to drug loading efficiency due to the reliance of electrostatic effects for diffusive loading. Particles containing 5 mole % total crosslinker were able to load between 24.3% and 29.2% w/w but particles with only 2.5 mole % crosslinker was only able to sequester 11.8% w/w of KAFAK. The lower loading capacity of the 2.5 mole % also correlates to the lower zeta potential, and thus may be due to a lower charge to volume ratio in these particles.

TEM Analysis

Figure 11:
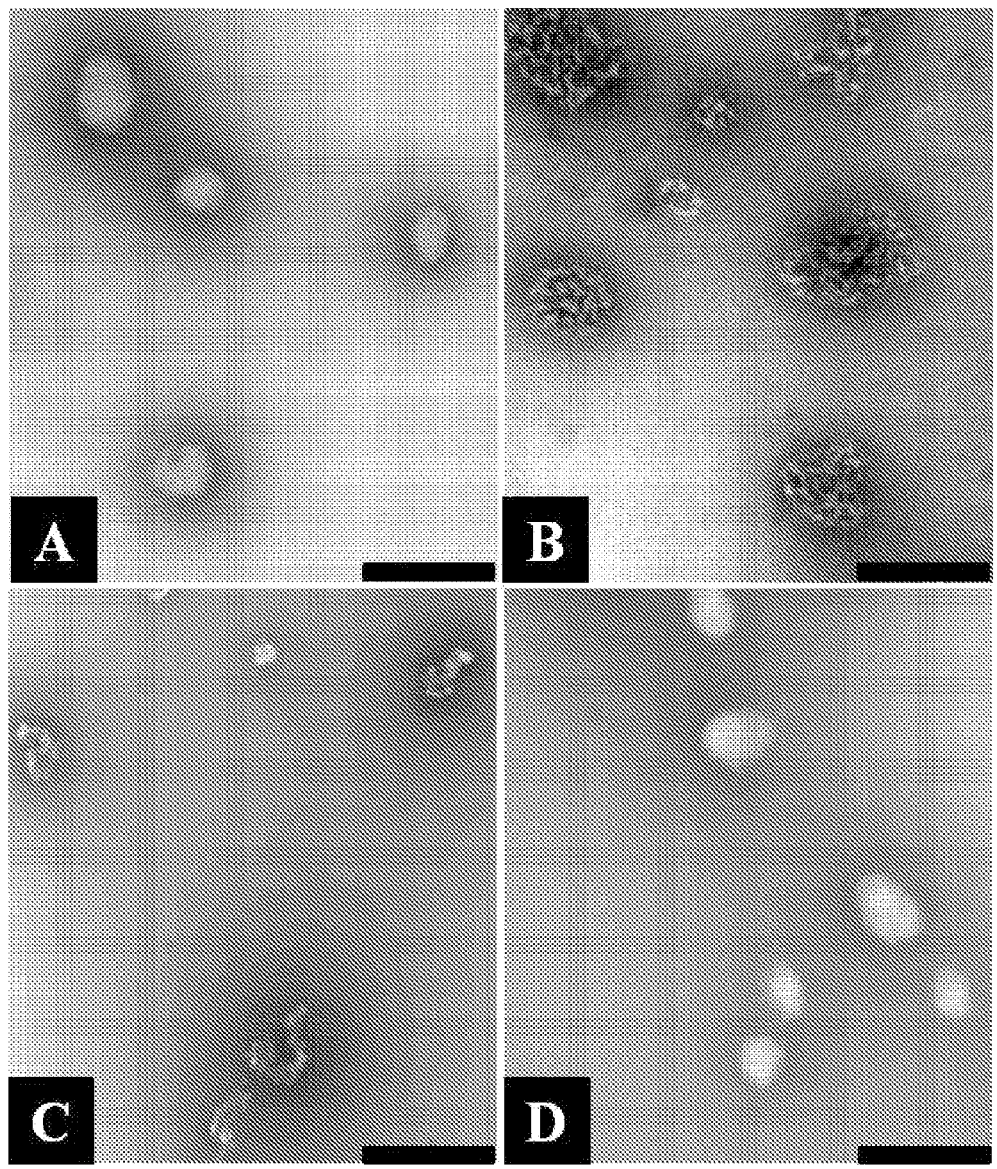
FIG. 11. TEM micrographs of Poly(NIPAm-DMHA-AMPS) nanoparticles containing 5 mole % DMHA and 5 mole % AMPS. A) pH 3.0 PBS after 4 Days at 37° C. B) pH 7.4 PBS after 4 Days at 37° C. C) pH 9.0 after PBS 4 Days at 37° C. D) Lyophilized 4 days and resuspended in MilliQ Water for 4 hours at 23° C. prior to TEM. Scale Bar is 500 nm.
Figure 15:
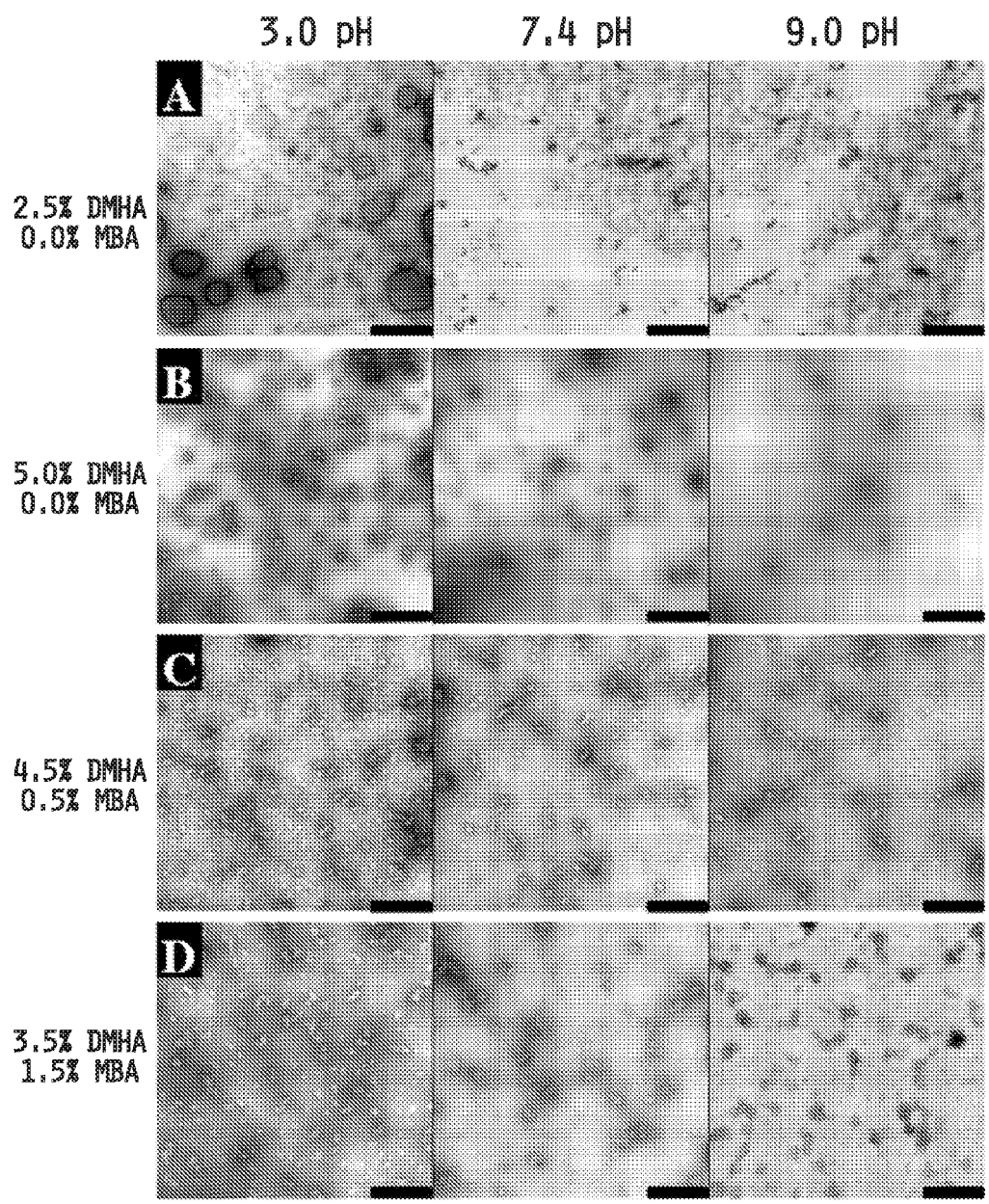
FIG. 15. TEM Images of poly(NIPAm-AMPS) nanoparticles with different compositions of cross-linker at pH 3.0, 7.4, and 9.0 over a 4 day incubation at 37° C. Scale bar is 1000 nm.

TEM images in FIG. 11 show particle integrity at various pH environments for 5% DMHA particles. TEM images of the other particle formulations can be seen in FIG. 15. TEM confirms that particles maintained integrity as long as they were not introduced to an environment with a pH>5. It also confirms that particles were able to maintain this integrity even through lyophilization in a deionized MilliQ water environment. After 4 days of incubation time at pH 3.0 particles did not show significant signs of degradation, but at pH 7.4 nanoparticles pitted and started to fragment. At pH 9.0 and at 4 days nanoparticles had broken down into smaller polymer fragments.

TEM images indicated that particles were largely stable at pH 3.0 for four days. However, after introducing the particles to an environment above pH 5.0 degradation occurs more rapid as a function of higher pH. Degradation took place at 37° C. for both the TEM images of FIG. 12 and the dynamic light scattering of FIG. 10. However, TEM was conducted at room temperature in a dried state and as a result, DMHA only particles were held together at 37° C. due to phase seperation above the LCST. As a consequence, they show up on TEM as fragments or highly degraded particles after incubation in basic conditions. Conversely, particles containing MBA did remain mostly intact due to non-degradable crosslinking.

Example 12

Drug Loading & Release—Study 2

Peptide synthesis and purification was performed as described above. Purified peptide was dissolved in MilliQ water to create a 30 mg/ml loading solution. Then this solution was added to 60 mg lyophilized nanoparticles with 5% AMPS and varying amounts of cross-linker. Then, the drug-nanoparticle loading solution complex was allowed to incubate for 24 hours at 4° C. in the swollen state. After incubation 9 ml of MilliQ water was added and particles underwent 1 hour of centrifugation at 35,000 rpm and 37° C. in an Optima L-90k Ultracentrifuge (Beckman Coulter, Indianapolis, Ind., USA). Nanoparticle pellet was briefly resuspended in 2 ml MilliQ water and was lyophilized. Loaded nanoparticles were suspended in sterile PBS at pH 3.0, pH 7.4, or pH 9.0 (Invitrogen, Grand Island, N.Y., USA) at a concentration of 0.5 mg/ml loaded particles. Measurement of free peptide released into the solution and the amount of peptide loaded were determined using fluorescence analysis with a fluoraldehyde o-Phthalaldehyde (OPA) solution (Thermo Scientific, Waltham Mass., USA). For drug release studies fluorescent measurements of drug release were taken every 30 minutes for the first hour, then at 2 hours, 4 hours, 20 hours, and every day afterward for 7 days. A final measurement was taken at 10 days. To ensure that only free peptide, and not particles or their fragments, were present in the measurement sample, each sample was run through a 100K molecular weight cutoff membrane microcentrifuge tube (Omega, Norcross, Ga., USA) prior to fluorescent analysis. Testing revealed no free peptide stuck to this size exclusion membrane and the membrane separated the nanoparticles from the solution (unpublished results). Images of particles containing fluorescein isothiocyanate (FITC) labeled peptides were taken with an Olympus FV1000 confocal microscope.

Figure 12:
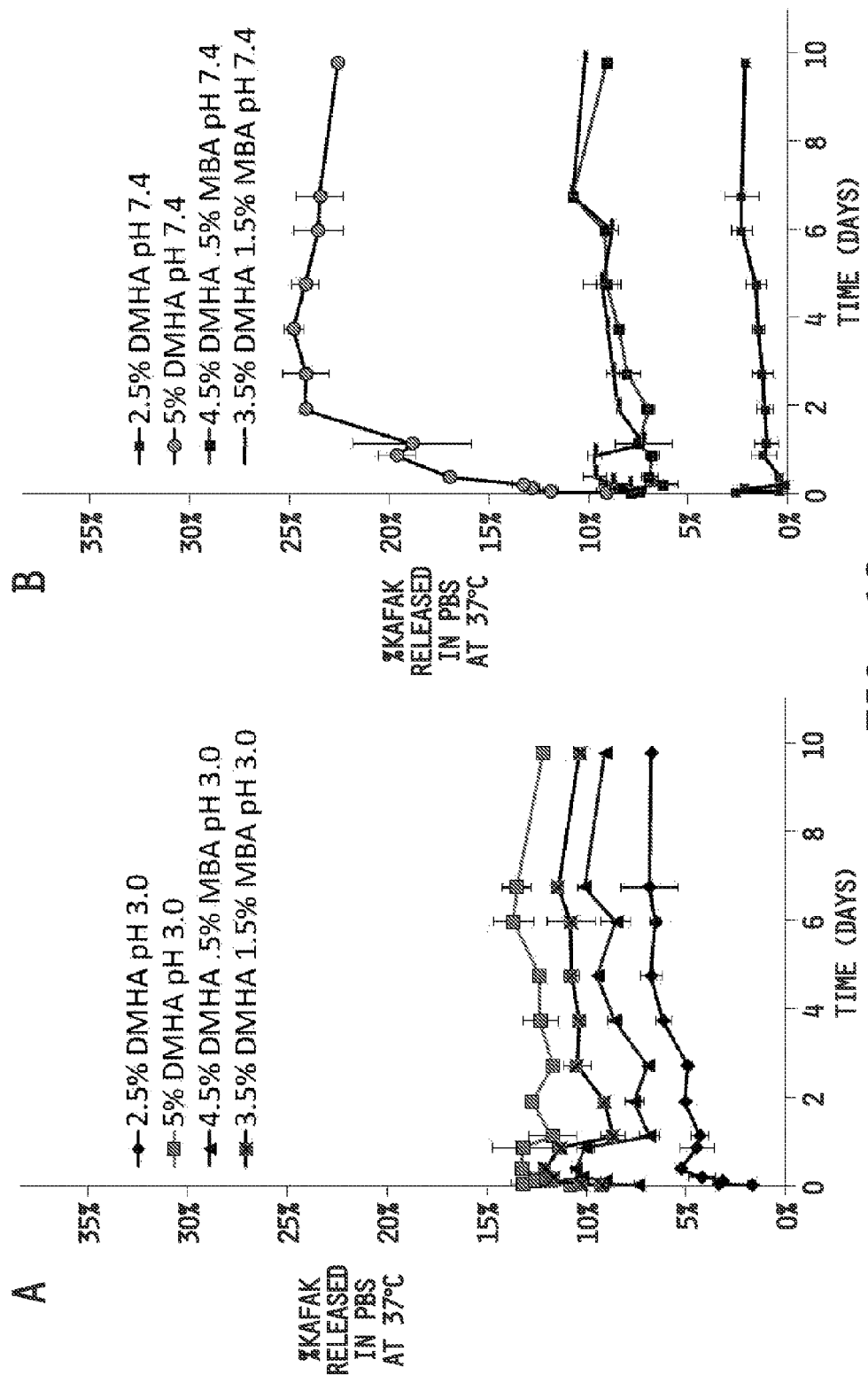
FIG. 12. 10 day release profile of poly(NIPAm-AMPS) nanoparticles varying MBA and DMHA. Measurement of free soluble KAFAK only. A) Release profile of nanoparticles in pH 3.0 PBS and 37° C. B) Release profile of nanoparticles in pH 7.4 PBS and 37° C.

In order to determine the impact of hydrolytic degradation on drug release, measurements of free KAFAK were taken and the data is shown in FIG. 12. The amount of free peptide released from 5% DMHA particles was only 5-10% more than the amount released from non-degradable poly(NI-PAm-MBA-AMPS) nanoparticles as reported previously. Very little free KAFAK was actually released from particles containing only 2.5% DMHA.

Figure 16:
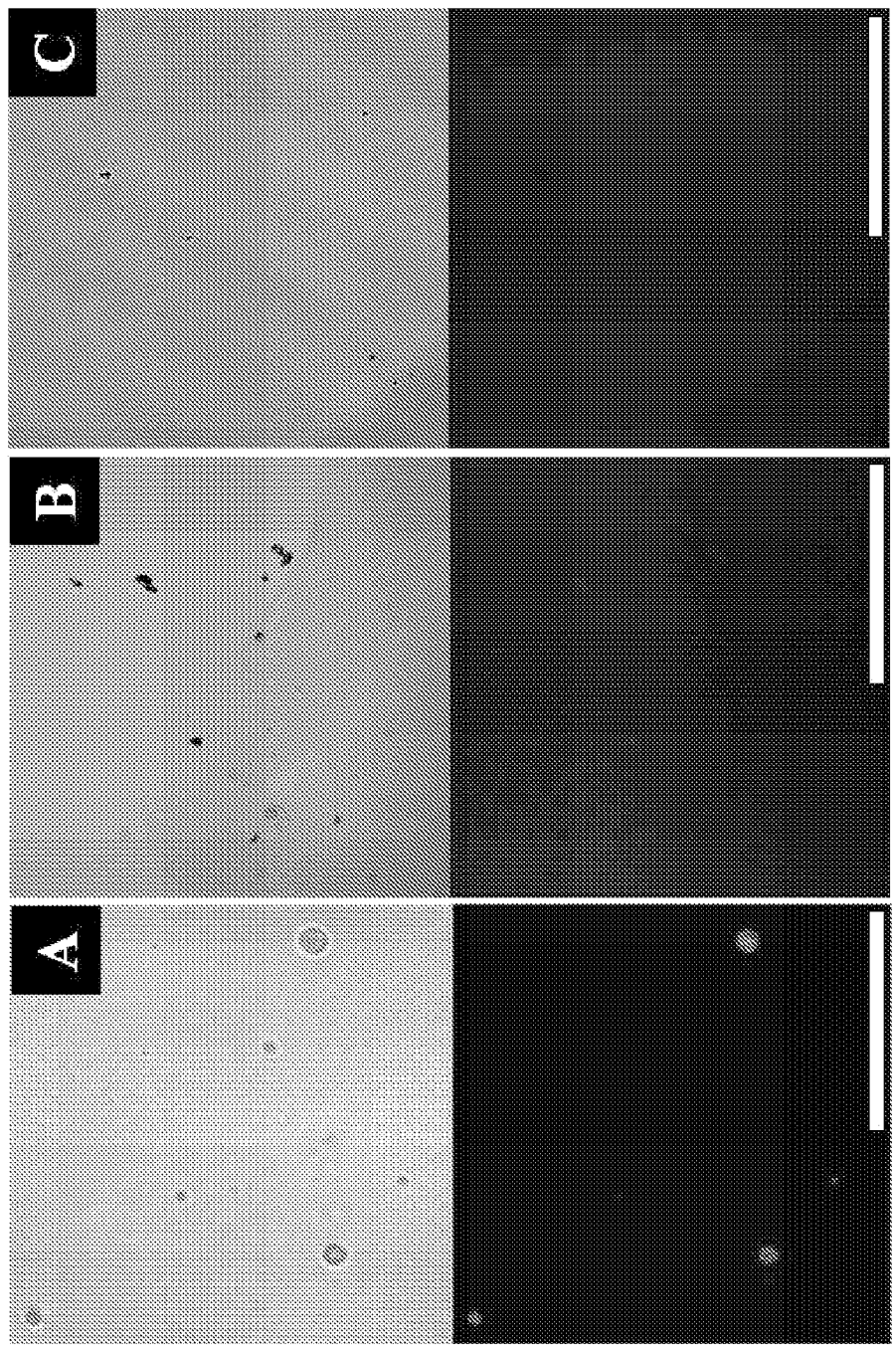
FIG. 16. Confocal image of FITC labeled KAFAK loaded inside poly(NIPAm-DMHA-AMPS) nanoparticles. A) Image after 1 hour in pH 7.4 PBS at 37° C. B) Image after 24 hours in PBS pH 7.4 at 37° C. C) Image after 4 days in PBS pH 7.4 at 37° C. Images were taken at 23° C. Instrument was set to eliminate background signal for image A and the same settings were used for images B and C. Scale bar is 5000 nm.

Nanoparticles containing only 5% DMHA showed a degradation dependent KAFAK release profile that correlates to the size measurements in FIG. 10. Also, particles with 5% DMHA did not release free peptide under pH 3.0 conditions because the DMHA does not break down below pH 5.0. Since this drug release study measured only the amount of free KAFAK by using a seperatory membrane, which seperated free peptide from peptide bound to polymer fragemnts in addition to that still encapsulated in the nanopartilces, it is likely that additional KAFAK released from degradable particles is associated with individual polymer chains and polymer fragments and retained with the particles during seperation with the membrane filter. This is supported by the release of KAFAK at 10 days from the 2.5% and 5% DMHA nanoparticles at pH 7.4, as well as the confocal images of the degraded particles over 4 days at pH 7.4 (FIG. 16).

Example 13

Confocal Images

Utilizing FITC-labeled KAFAK showed, through confocal imaging, that KAFAK is loaded inside the nanoparticles. This is consistent with prior studies with non-degradable poly(NIPAm-MBA-AMPS) nanoparticles. In FIG. 16, particles after 1 hour exhibited little sign of degradation or release of KAFAK. Particles after 24 hours released nearly all KAFAK but large polymer fragments with associated KAFAK are barely visible. Similarly after 4 days nearly all fragments have been degraded but there are still faint pieces of polymer fragments with associated KAFAK. Based on the drug release results shown in FIG. 12 and FIG. 16, it is likely that KAFAK is weakly bound to fragmented polymer strands unless other charged materials neutralize the interaction and cause a final dissociation and release of the KAFAK from the fragments. This is also evident in FIG. 13, which demonstrates that nearly all loaded KAFAK is therapeutically active after 4 days of release in PBS at pH 7.4.

Example 14

Cell Culture

Immortalized human monocytes (THP-1, ATCC, Manassas, Va., USA) were grown in RPMI 1640 with L-glutamine (Mediatech Inc, Manassas, Va., USA) supplemented with 0.05 mM (3-mercaptoethanol (Sigma-Aldrich), 10 mM HEPES (Mediatech Inc), 1 mM sodium pyruvate (Mediatech Inc), 10% fetal bovine serum (Thermo Scientific) and 1% penicillin/streptomycin (Mediatech Inc). Cells were used between passage numbers 4 and 8 and maintained at 37° C. with 5% $CO_2$.

Example 15

In Vitro Inflammatory Model

THP-1 cells were seeded at a density of 200,000 cells/ml and treated with 10 ng/ml phorbol 12-myristate 13-acetate (PMA) (Sigma-Aldrich) for 48 hours to cause differentiation (confirmed by the monocytes becoming adherent). After a media change, cells were treated with 50 ng/ml lipopolysaccharide (LPS) (Sigma-Aldrich), MK2 inhibitor peptide in PBS (Sigma-Aldrich), or nanoparticles in PBS (Sigma-Aldrich). Control samples received PBS in place of LPS and/or therapy treatments with nanoparticles. After 6 h incubation in the cell culture incubator, the supernatant was collected and stored at −80° C. until cytokine analysis could be performed. The number of live cells was determined using the CellTiter 96 AQueous One Proliferation Assay Reagent (Promega, Madison, Wis., USA). 20 µl of reagent was added directly to 100 µl of cells and media. After 2 h of incubation in the cell culture incubator, the absorbance was read at 490 nm with a correction at 650 nm.

Example 16

Cytokine Analysis

TNF-α production was determined with a human ELISA development kit (Peprotech, Rocky Hill, N.J.). Capture antibody was coated overnight onto Nunc MaxiSorp 96-well plates. The plate was washed and incubated for one hour with 1% bovine serum albumin (Sera Life Sciences, Milford, Mass.) in PBS solution. After washing blocking buffer away, samples and standards were incubated with gentle shaking for 2 hours. After washing the samples, plates were incubated with a detection antibody for one hour, washed, and incubated with avidin-horse radish peroxidase conjugate for 30 minutes. The samples were developed by adding 2,2'-azino-bis(3-ethylbenzthiazoline-6-sulphonic acid) (ABTS) liquid substrate (Sigma-Aldrich) and read on absorbance plate reader at 405 nm with a correction at 650 nm. TNF-α production was analyzed at 25 minutes. TNF-α was normalized to cell number with CellTiter data.

The inhibition of MK2 by KAFAK results in suppression of TNF-α expression in addition to other pro-inflammatory cytokines downstream of MK2 in the inflammation cascade. Studies of THP1 human monocyte cell line confirmed that KAFAK released from the nanoparticles is active in vitro.

Figure 13:
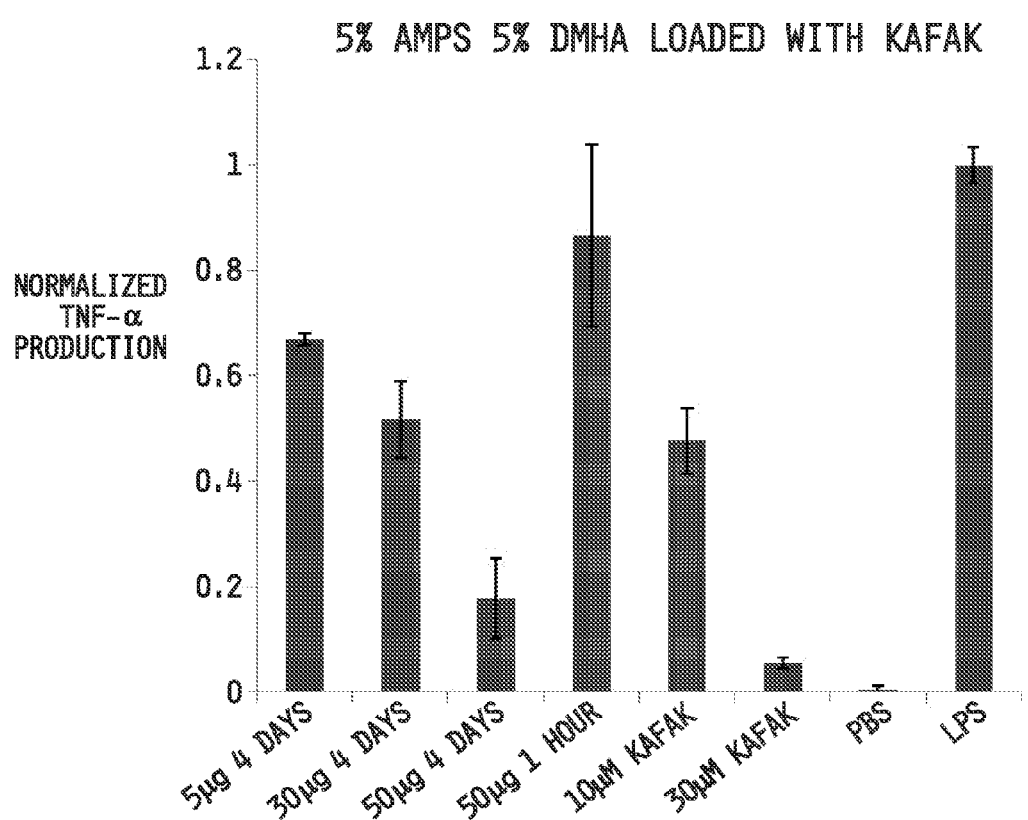
FIG. 13. ELISA results using poly(NIPAm-DMHA-AMPS) nanoparticles loaded with KAFAK to inhibit TNF-α production in THP1 human monocytes.
Figure 14:
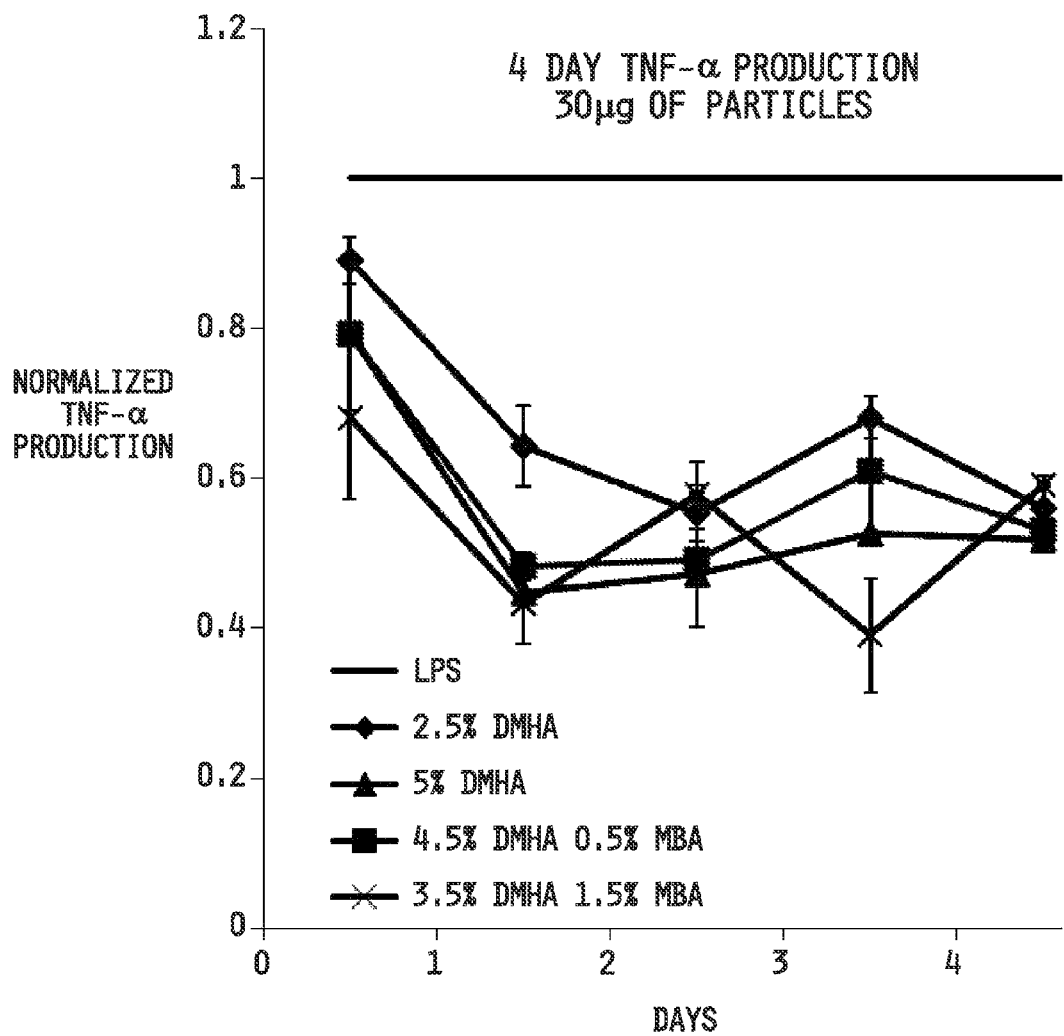
FIG. 14. 4 day release study ELISA results of TNF-α production of KAFAK loaded poly(NIPAm-AMPS) nanoparticles with varying amounts of DMHA and MBA crosslinker.

FIG. 13 indicates that different dosages of KAFAK lodaded 5% DMHA nanoparticles yield a dose dependent inhibition of TNF-α production after 4 days. Also, a 50 µg dose of KAFAK loaded 5% DMHA 5% AMPS nanoparticles did not sufficiently reduce TNF-α expression after only 1 hour of time to in PBS pH 7.4. This is consistent with nanoparticle degradation kinetics in FIG. 10 and release profile concentration of FIG. 12. Taken together this information indicates that in vitro therapeutic concentration of KAFAK is dependent on the kinetics of particle breakdown. Controlled release of the sequestered KAFAK, primarily via nanoparticle erosion, yields inhibition of TNF-α production over time as shown for a 4-day time period in FIG. 14. This data demonstrates that the nanoparticle system can both sequester KAFAK and release it in a biologically active form over several days.

Particles with 2.5% DMHA were initially loaded with 11.8% w/w KAFAK compared to between 24.3-29.2% w/w for nanoparticles containing 5 mole % crosslinker. As a result 2.5% DMHA particles are less effective than the latter particles over the 4 day release period. Particles containing 5% crosslinker released enough therapeutically active KAFAK to inhibit approximately 50% TNF-α production after day 1. The amount of drug released correlates well with the therapeutic window of KAFAK in THP1 Human Monocytes, which was previously reported to be between 10 µM and 30 µM. Increasing the dose above 30 µg to the upper toxicity limit of 60 µg (30 µM KAFAK) will improve the therapeutic efficacy of KAFAK as is seen with the 5% DMHA particle data shown in FIG. 13.

Figure 17:
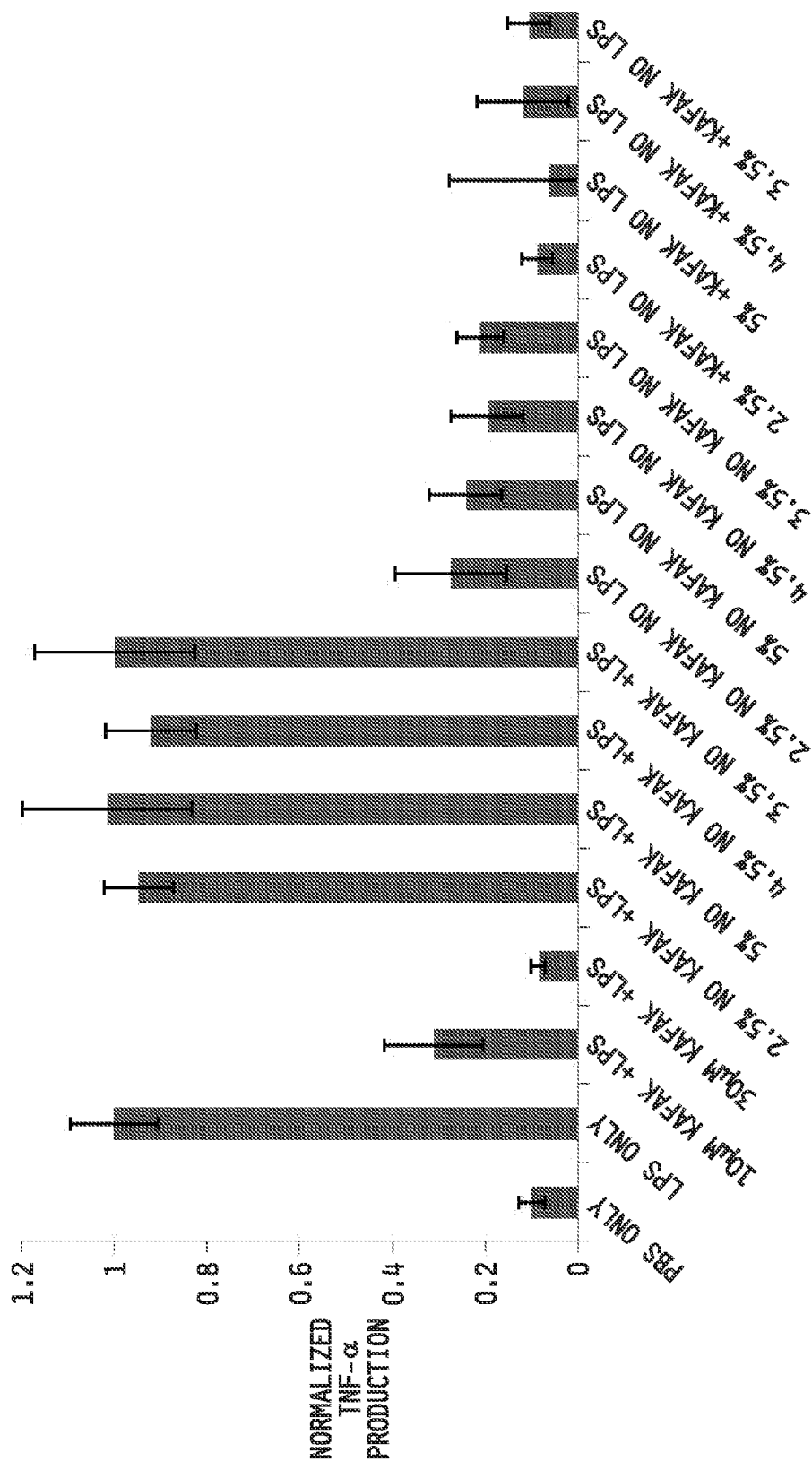
FIG. 17. Normalized TNF-α production with different control treatments of poly(NIPAm-DMHA/MBA-AMPS) nanoparticles with and without KAFAK and LPS.
Figure 18:
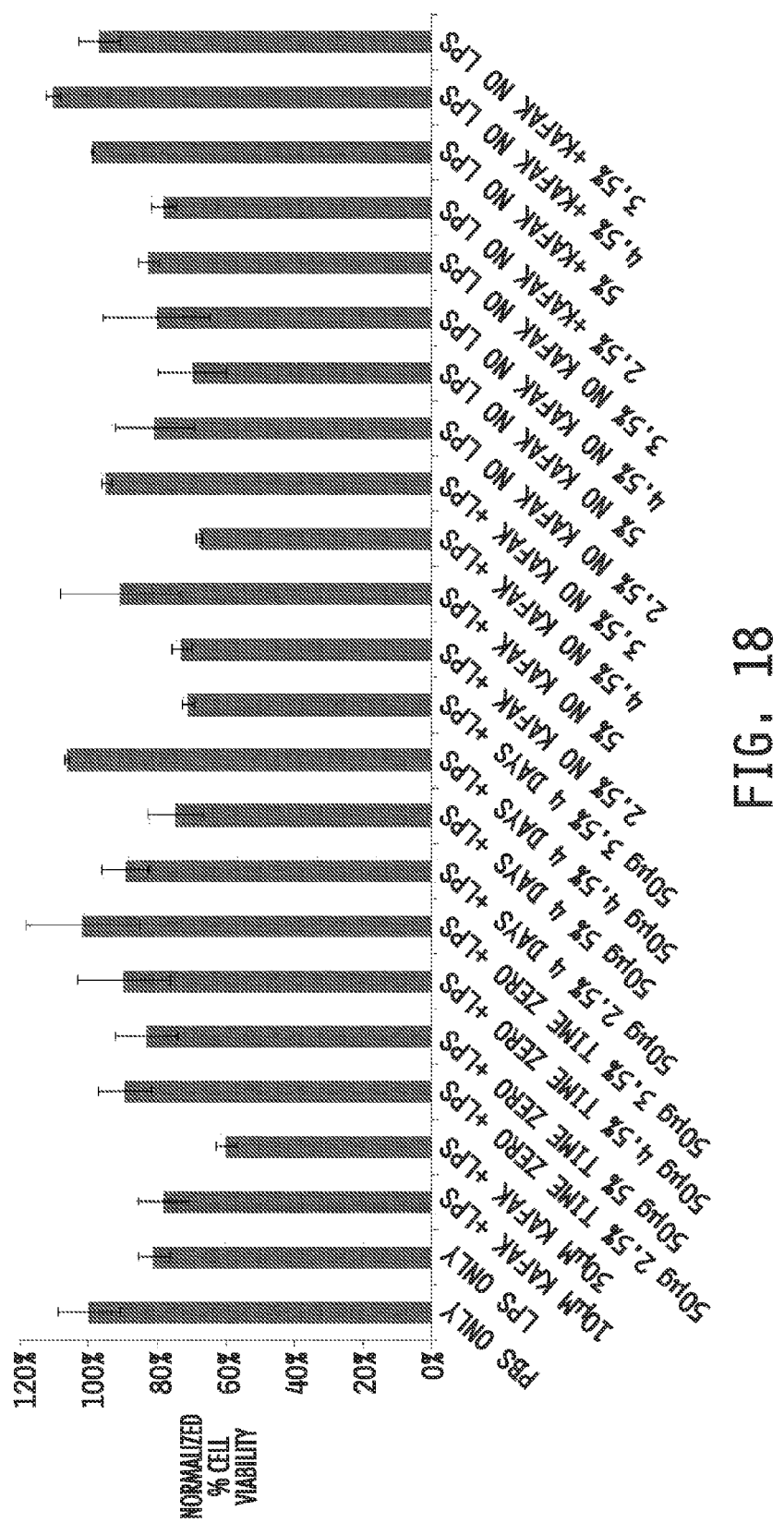
FIG. 18. CellTitre cell viability results with different control treatments of poly(NIPAm-DMHA/MBA-AMPS) nanoparticles with and without KAFAK and LPS.

In order to determine nanoparticle toxicity and also normalize THP1 cell number to TNF-α production, the number of viable cells was determined using a CellTiter 96 AQueous One Proliferation Assay Reagent. According to this method cell viability was not impacted by the addition of nanoparticles indicating minimal if any toxicity (FIG. 18).
ELISA Inflammation Studies of TNF-α Expression As shown in FIG. 17, nanoparticles of all crosslinker composition tested in this study did not induce or inhibit TNF-α expression alone. Nanoparticles were initially solubilized in PBS pH 7.4 for 1 hour prior to the 6-hour incubation study. This ensured that both nanoparticles and degradation fragments were involved in the inflammation analysis. Overall, without the addition of lipopolysaccharide (LPS), no upregulation of TNF-α was seen in treatments of only particles, particles with KAFAK, or KAFAK alone. Similarly, there was no down-regulation of the inflammatory effect of LPS without the addition of KAFAK either alone or loaded in particles. Also, CellTitre live dead analysis shown in FIG. 18 demonstrated that the nanoparticles alone did not exhibit statistically significant toxicity to cells through the assay.

Example 17

Nanogel Synthesis

NIPAm-containing nanogels were synthesized using standard precipitation polymerization. Briefly, the nanogel compositions described in Table 7 were formed by dissolving 768.5 mg NIPAm, MBA if required, and AMPSA in 30 ml degassed MilliQ water in a three neck round bottom flask.

TABLE 7

Nanoparticle Cross linking Composition

| Mole % AMPS | 0% | 5% | 10% | 5% |
| Mole % MBA | 2% | 2% | 2% | 0% |
| Mole % DMHA | 0% | 0% | 0% | 5% |

If DMHA was added it was pre-dissolved in 10 ml of dimethyl sulfoxide (DMSO). If DMHA was not added, 10 ml of DMSO was added to the reaction flask after 5 minutes. After addition of the DMHA or DMSO alone, 575 µA of a 10% SDS in MilliQ water solution were added, and the mixture was heated to 75° C. under nitrogen. 33.7 mg of potassium persulfate was dissolved in 10 ml degassed MilliQ water and added after 30 minutes equilibration to initiate polymerization. After 4 hours, the reaction was removed from heat and allowed to cool to room temperature. Particles were dialyzed against MilliQ water for 7 days using a 15,000 MWCO membrane. Post dialysis concentrations varied between 6-15 mg/ml and were diluted or concentrated as necessary through lyophilzation and resuspension. To lyophilize nanoparticle, solutions were frozen to −80° C. for 12 hours and then placed under lyophilizer vacuum until the liquid was removed.

Example 18

Nanogel Characterization

After calibration with polystyrene beads a Nano-ZS90 Zetasizer (Malvern, Westborough, Mass., USA) was used to measure nanoparticle diameter through dynamic light scattering (DLS). Samples were equilibrated for 2 minutes for each half-degree temperature change for a temperature sweep or 5 minutes for a static temperature measurement. Zeta (ς) potentials were measured at 23° C. by a Nano-ZS90 Zetasizer in folded capillary cells in MilliQ water. TEM was conducted at the Purdue University Life Science Microscope facility on a FEI/Philips CM-100 Transmission Electron Microscope at 100 Kv using an uranyl acetate stain (UA) at pH 4.5. Discharged TEM sample grids were placed onto the top of a droplet of sample for 2 minutes. Then UA stain was added and samples were briefly dried before imaging at room temperature.

Figure 20:
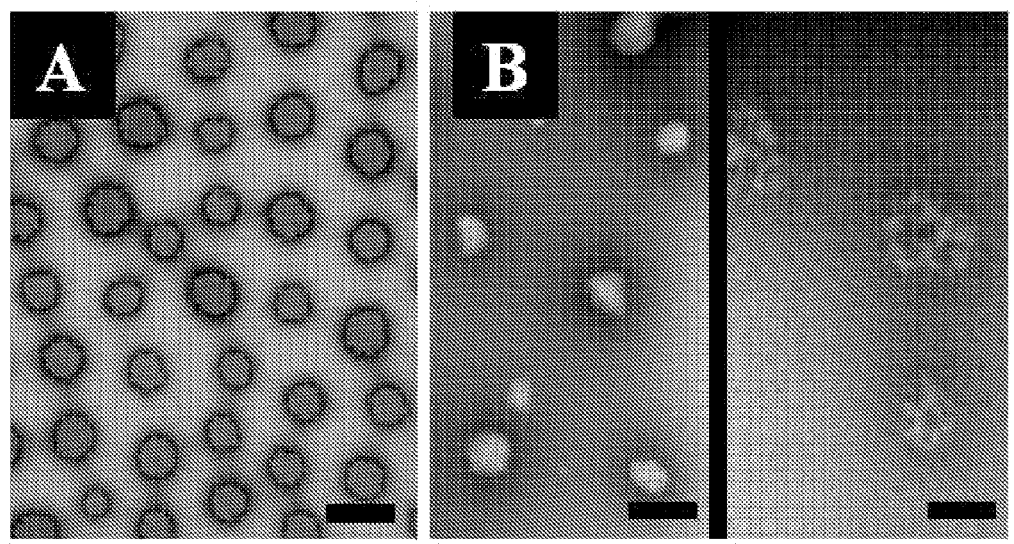
FIG. 20. A) Poly(NIPAm-5% AMPS-MBA) nanoparticles incubated in pH 7.4 PBS at 37° C. for 4 days. B) Poly (NIPAm-5% AMPS-DMHA) nanoparticles after 4 days incubation at 37° C. in PBS pH 3.0 (left) and pH 7.4 (right). Scale is 200 nm.

Adjustments to reaction conditions produced nanoparticles with sizes ranging between 100 nm and 400 nm in solution. Utilizing 5% AMPS co-monomer content produced particles with circular shape that do not readily aggregate and are capable of loading therapeutic peptides. FIG. 20 demonstrates that particles containing 5% AMPS form spherical nanoparticles when cross-linked with MBA or DMHA.

Figure 19:
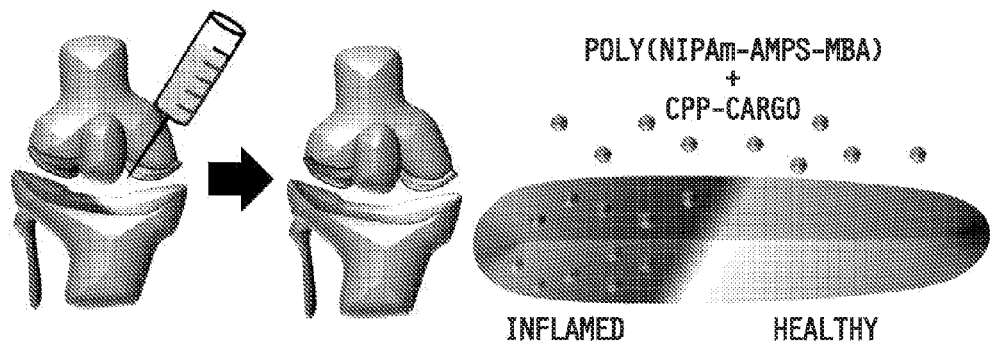
FIG. 19. Schematic representation of inter articular therapy.

Incorporation of MBA produces nanoparticles that do not degrade under physiologically relevant temperature and pH (FIG. 19). However, it is also possible to incorporate pH sensitive cross-linker DMHA that degrades slowly over time under physiologically relevant environments. This selective degradation has been shown to be a useful property for drug release. In addition, use of AMPS allows for increased Zeta potential and increased drug loading of cationic cell penetrating peptide KAFAK accordingly.

Example 19

Drug Loading into Nanoparticles

Peptide synthesis and purification was performed as described above. Purified peptide was dissolved in MilliQ water to create a 30 mg/ml loading solution. Then this solution was added to 60 mg lyophilized nanoparticles with 5% AMPS and varying amounts of cross-linker. Then, the drug-nanoparticle loading solution complex was allowed to incubate for 24 hours at 4° C. in the swollen state. After incubation 9 ml of MilliQ water was added and particles underwent 1 hour of centrifugation at 35,000 rpm and 37° C. in an Optima L-90k Ultracentrifuge (Beckman Coulter, Indianapolis, Ind., USA). Nanoparticle pellet was briefly re-suspended in 2 ml MilliQ water and was lyophilized. Loaded nanoparticles were suspended in sterile PBS or media (Invitrogen, Grand Island, N.Y., USA) at required concentrations. Measurement of free peptide released into the solution and the amount of peptide loaded was determined using fluorescence analysis with a fluoraldehyde o-Phthalaldehyde (OPA) solution (Thermo Scientific, Waltham Mass., USA). Images of particles containing fluorescein isothiocyanate (FITC) labeled peptides were taken with an Olympus FV1000 confocal microscope.

Table 8 demonstrates that varying the molar concentration of AMPS contained within nanoparticle formulations has a direct impact on the amount of drug loaded. It is also important to point out that passive drug loading by diffusion can be easily achieved with poly(NIPAm-AMPS) nanoparticles due to a LCST between 31-33° C.

TABLE 8

Poly(NIPAm-AMPS) Nanoparticle Properties

| | 0% AMPS 2% MBA | 5% AMPS 2% MBA | 10% AMPS 2% MBA | 5% AMPS 5% DMHA |
|---|---|---|---|---|
| Drug Loading by weight | 17.8 ± 7.1% | 45.3 ± 9.5% | 60.5 ± 6.2% | 24.30 ± 4.10% |
| Zeta Potential | −6.1 ± 0.9 mv | −13.6 ± 1.4 mv | −22.9 ± 3.3 mv | −15.6 ± 1.7 mv |
| Diameter at 23° C. | 293.8 ± 10.0 nm | 315.1 ± 17.4 nm | 358.1 ± 52.1 nm | 408.2 ± 6.6 nm |

TABLE 8-continued

| | Poly(NIPAm-AMPS) Nanoparticle Properties | | | |
|---|---|---|---|---|
| | 0% AMPS 2% MBA | 5% AMPS 2% MBA | 10% AMPS 2% MBA | 5% AMPS 5% DMHA |
| Diameter at 37° C. | 129.1 ± 10.5 nm | 222.6 ± 14.5 nm | 288.3 ± 49.8 nm | 232.5 ± 4.7 nm |
| Chondrocyte Viability | 107.8 ± 11.7% | 99.4 ± 11.4% | 104.5 ± 3.3% | 102.7 ± 6.2% |
| Macrophage Viability | 107.1 ± 4.4% | 110.7 ± 2.5% | 105.7 ± 3.7% | 90.7 ± 10.2% |

Figure 21:
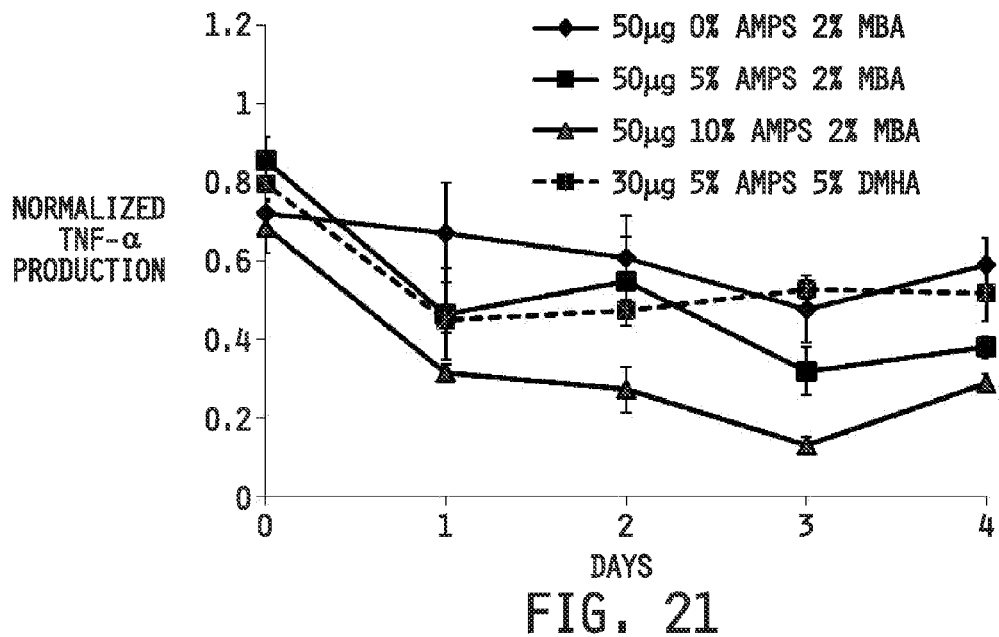
FIG. 21. TNFα production over time in macrophages for varying nanoparticle compositions.

This LCST allows for particles to be larger by a factor of 1.2 to 2.2 below the LCST. This variation in swelling at lower temperature is directly related to incorporation of AMPS. As shown in Table 8, none of the poly(NIPAm-AMPS) nanoparticles show a statistically significant decrease in cell viability of chondrocytes or macrophages. Poly(NIPAm-AMPS) nanoparticles protect KAFAK from serum proteases thus enabling the long term release shown and suppression of pro-inflammatory cytokine TNF-α in macrophages in FIG. 21. This long term suppression was based directly on the amount of therapeutically active KAFAK delivered.

Example 20

In Vitro Inflammatory Macrophage Model

THP-1 Immortalized human monocytes were grown as described above. THP-1 cells were seeded at a density of 200,000 cells/ml and treated with 10 ng/ml phorbol 12-myristate 13-acetate (PMA) (Sigma-Aldrich) for 48 hours to cause differentiation (confirmed by the monocytes becoming adherent). After a media change, cells were treated with 50 ng/ml lipopolysaccharide (LPS) (Sigma-Aldrich), MK2 inhibitor peptide in PBS (Sigma-Aldrich), or nanoparticles in PBS (Sigma-Aldrich). Control samples received PBS in place of LPS and/or therapy treatments with nanoparticles. After 6 h incubation in the cell culture incubator, the supernatant was collected and stored at −80° C. until cytokine analysis could be performed. The number of live cells was determined using the CellTiter 96 AQueous One Proliferation Assay Reagent (Promega, Madison, Wis., USA). 20 µl of reagent was added directly to 100 µl of cells and media. After 2 h of incubation in the cell culture incubator, the absorbance was read at 490 nm with a correction at 650 nm.

Reduction in TNF-α activity in macrophages begins after 1 day of treatment with KAFAK loaded nanoparticles in vitro and is sustained with further dosages of treatment with drug releasing nanoparticles. Also demonstrated is that degradable nanoparticle formulations containing DMHA release the greatest amount of therapeutically active KAFAK. This is most likely due to the previously reported phenomenon of poly(NIPAm-MBA-AMPS) nanoparticles where KAFAK is not able to release completely from non-degradable nanoparticle systems.

Figure 22:
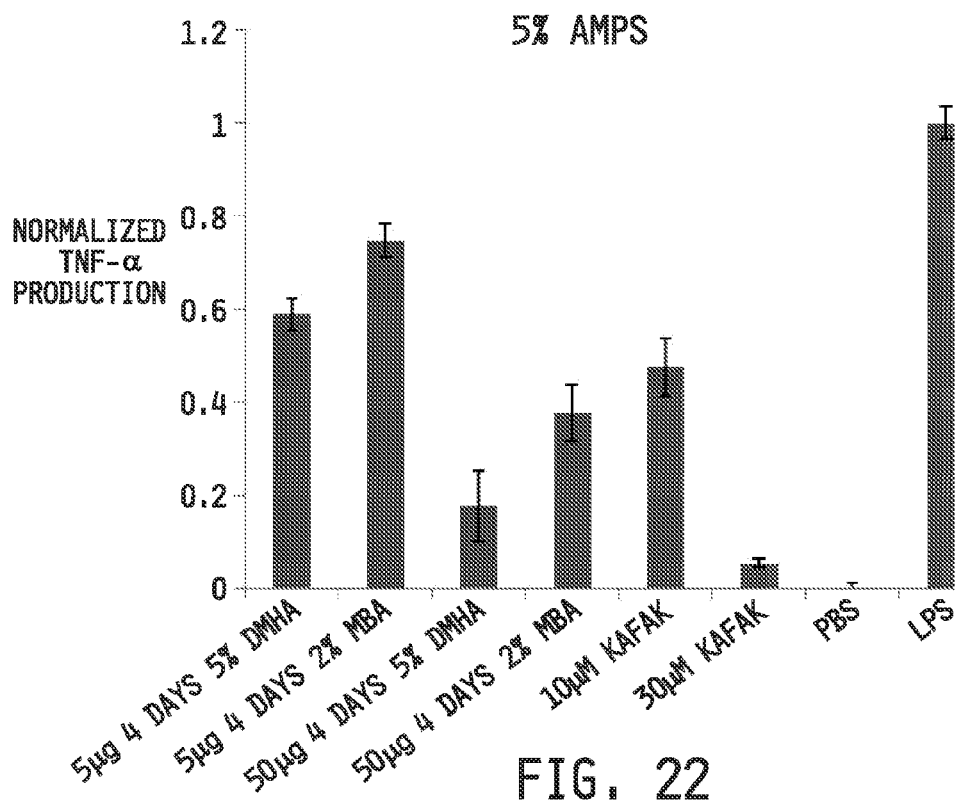
FIG. 22. TNFα production with various compositions of nanoparticles and varying amounts to show it has a dose dependent response and a time dependent response.

FIG. 22 demonstrates that a dose dependent response is achieved by varying the concentration of nanoparticles. FIG. 22 also shows, similar to FIG. 21, that degradable nanoparticles containing DMHA instead of MBA have a greater therapeutic effect due to increase in the amount of therapeutically available KAFAK.

Suppression of TNF-α has been previously shown to be an essential sign of down regulation of the pro-inflammatory cytokine cascade in macrophages. Poly(NIPAm-AMPS) nanoparticles loaded with KAFAK are able to suppress this cascade in macrophages.

Example 21

Chondrocyte Isolation and Culture

Primary chondrocytes were harvested from three-month-old bovine knee joints obtained from an abattoir within 24 hours of slaughter (Dutch Valley Veal, South Holland, Ill., USA). Cartilage slices, 150-200 µm thick were shaved from the lateral femoral condyle and washed three times in serum free DMEM medium (50 µg/mL ascorbic acid 2-phosphate, 100 µg/mL sodium pyruvate, 0.1% bovine serum albumin, 100 units/mL penicillin, 100 µg/mL streptomycin and 25 mM HEPES) prior to digestion with 3% fetal bovine serum (FBS) and 0.2% collagenase-P (Roche, Indianapolis, Ind., USA) at 37° C. for six hours. Released chondrocytes were filtered through 70 µm cell strainer and centrifuged at 1000 rpm three times for five minutes each in medium listed above supplemented with 10% FBS. The cell pellet was re-suspended in 10% FBS supplemented media and plated at 10,000 cells/mL cell density in a 37° C., 5% $CO_2$ humidified incubator until confluent. Cells were used between passage 2 and 4 and seeded at 100,000 cells/ml for experiment. To test the effect of nanoparticles and KAFAK on chondrocyte viability, treatments of nanoparticles and KAFAK were added to chondrocytes and incubated for 6 hours. The number of live cells after 6 hours was determined using the CellTiter 96 AQueous One Proliferation Assay Reagent (Promega, Madison, Wis., USA). 20 µl of reagent was added directly to 100 µl of cells and media. After 2 h of incubation in the cell culture incubator, the absorbance was read at 490 nm with a correction at 650 nm.

Example 22

Ex Vivo Inflammatory Model

Cartilage plugs were obtained from three month old bovine knee joints obtained from an abattoir within 24 hours of slaughter (Dutch Valley Veal, South Holland, Ill., USA). The plugs were removed from the load bearing region of the femoral condoyle using a 3 mm diameter cork borer. They were then washed three times in serum free medium and equilibrated for three days in 5% FBS supplemented media. Osteoarthritis (OA)-like conditions were simulated by removal of native aggrecan using a previously described protocol. Briefly, plugs were treated with 0.5% (w/v) trypsin in HBSS for 3 hours at 37° C. After trypsin treatment plugs were washed three times in HBSS and incubated with 20% FBS to inactivate residual trypsin activity. Inflammation was initiated in the plugs by treating with 20 ng/mL Il-1β. Nanoparticle treatments as specified in Table1, were added after day two of culture. Fresh IL-1β and nanoparticles were added every two days for an eight day culture period. Media aliquots were collected and stored in −80° C. till further analysis.

Example 23

Analysis of TNF-α in Human Macrophages

TNF-α production was determined with a human ELISA development kit (Peprotech, Rocky Hill, N.J.). Capture antibody was coated overnight onto Nunc MaxiSorp 96-well plates. The plate was washed and incubated for one hour with a 1% bovine serum 1% bovine serum albumin (Sera Life Sciences, Milford, Mass.) in PBS solution. After washing blocking buffer away, samples and standards were incubated with gentle shaking for 2 hours. After washing the samples, plates were incubated with a detection antibody for one hour, washed, and incubated with avidin-horse radish peroxidase conjugate for 30 minutes. The samples were developed by adding 2,2'-azino-bis(3-ethylbenzthiazoline-6-sulphonic acid) (ABTS) liquid substrate (Sigma-Aldrich) and read on absorbance plate reader at 405 nm with a correction at 650 nm. TNF-α production was analyzed at 25 minutes. TNF-α was normalized to cell number with Cell-Titer data.

Example 24

Confocal Analysis of Nanoparticles in Bovine Knee Plugs

Bovine cartilage plugs were either trypsin treated to simulate OA-like conditions or left in cell culture media to maintain healthy tissue like environment. Treatments of nanoparticles loaded with FITC labeled KAFAK were re-suspended at 0.5 mg/ml concentration in PBS. Control treatment of FITC KAFAK only was re-suspended at 0.15 mg/ml concentration. Diffusion through the plug was carried out by pipetting 10 µL of treatment or control solution onto articular surface every ten minutes for one hour. Excess solution was removed prior to next treatment.

After the last treatment, plugs were incubated for 1 hour at 37° C. and washed with 1×PBS three times. A mid sagittal cut was made through the plug to examine diffusion into the plugs from the top edge. Diffusion of FITC KAFAK was monitored using a 488 nm laser excitation on a confocal microscope (Olympus IX81) at 23° C.

Figure 23:
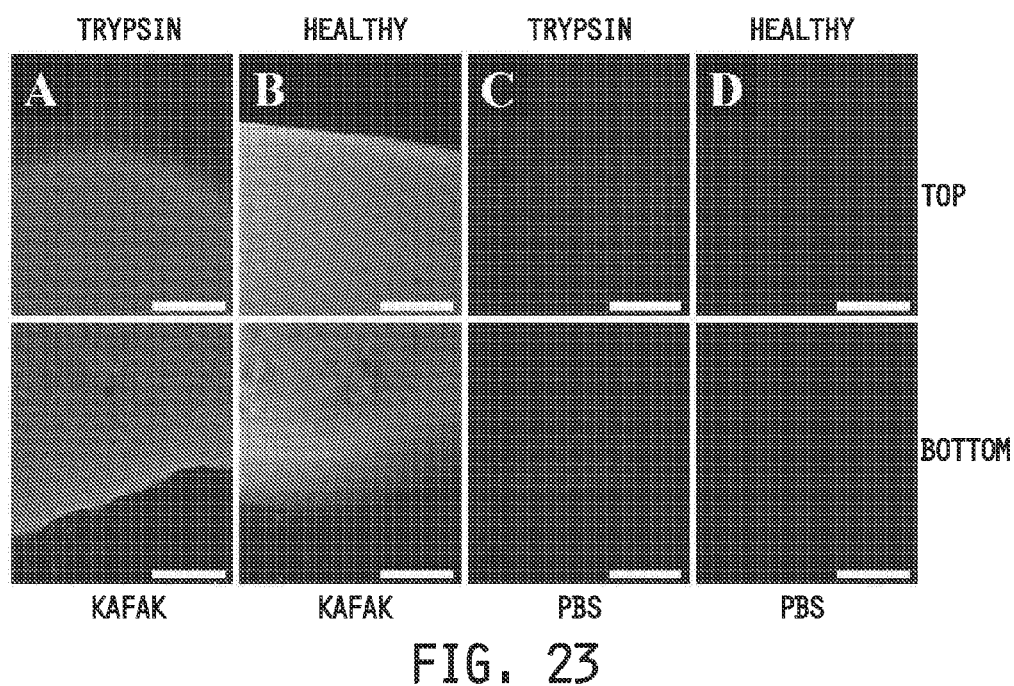
FIG. 23. Confocal of FITC labled KAFAK in Nanoparticles (Scale is 50 um).
Figure 24:
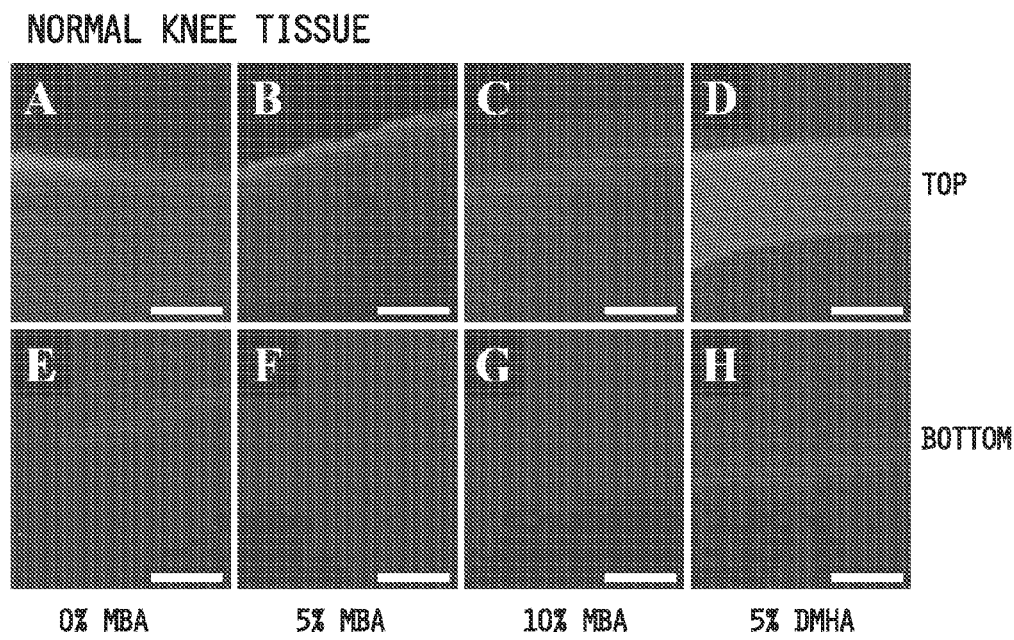
FIG. 24. Confocal of FITC labled KAFAK in Nanoparticles (Scale is 50 um).
Figure 25:
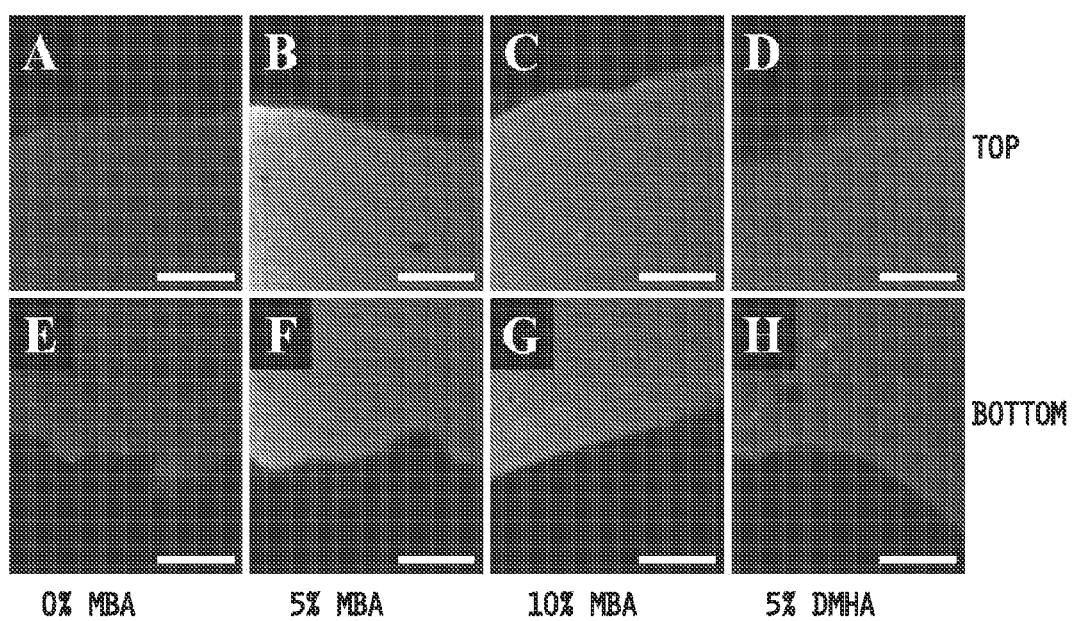
FIG. 25. Confocal of FITC labled KAFAK in Nanoparticles (Scale is 50 um).

To determine how nanoparticles would be distributed in an OA-like environment a bovine knee cartilage plug model was used. Trypsinizing the cartilage matrix removed native aggrecan, creating an unhealthy environment for chondrocytes. Diffusion was depicted by an increase in fluorescence. When treated with KAFAK alone (FIG. 23) there was no selectivity for treatment of healthy tissue or damaged tissue. However, when healthy tissue was exposed to nanoparticles loaded with KAFAK (FIG. 24), very little KAFAK was able to diffuse into the healthy knee plugs. The exception however was that some degradation fragments from DMHA degradable cross-linked particles were able to diffuse a short distance into the healthy cartilage (FIG. 24 D). When nanoparticles loaded with KAFAK were added to damaged cartilage plugs the nanoparticles were able to efficiently deliver KAFAK, diffusing from the top articular surface to the end deep zone. Overall, FIGS. 23, 24, and 25 show that KAFAK poly (NIPAm-APS) can be used specifically for targeting OA-induced tissue. Healthy tissue will not allow diffusion of these nanoparticles.

Example 25

Analysis of IL-6 in Bovine Knee Ex Vivo Model

IL-6 production was determined with a bovine IL-6 ELISA development kit (Thermo Scientific, Rockford, Ill., USA). Capture antibody was coated overnight onto Nunc MaxiSorp 96-well plates. The plate was washed and incubated for one hour with a 5% sucrose 4% bovine serum albumin (Sera Life Sciences, Milford, Mass.) in PBS solution. After washing blocking buffer away, samples and standards were incubated with gentle shaking for one hour. After washing the samples, plates were incubated with a detection antibody for one hour, washed, and incubated with Streptavidin-HRP for 30 minutes. The samples were developed by adding 3,3',5,5'-tetramethylbenzidine (TMB) liquid substrate for 20 minutes before adding a 0.16M sulfuric acid stop solution. The plate was read on absorbance plate reader at 450 nm with a correction at 550 nm. IL-6 production was normalized to plug weight and to the negative control.

Figure 26:
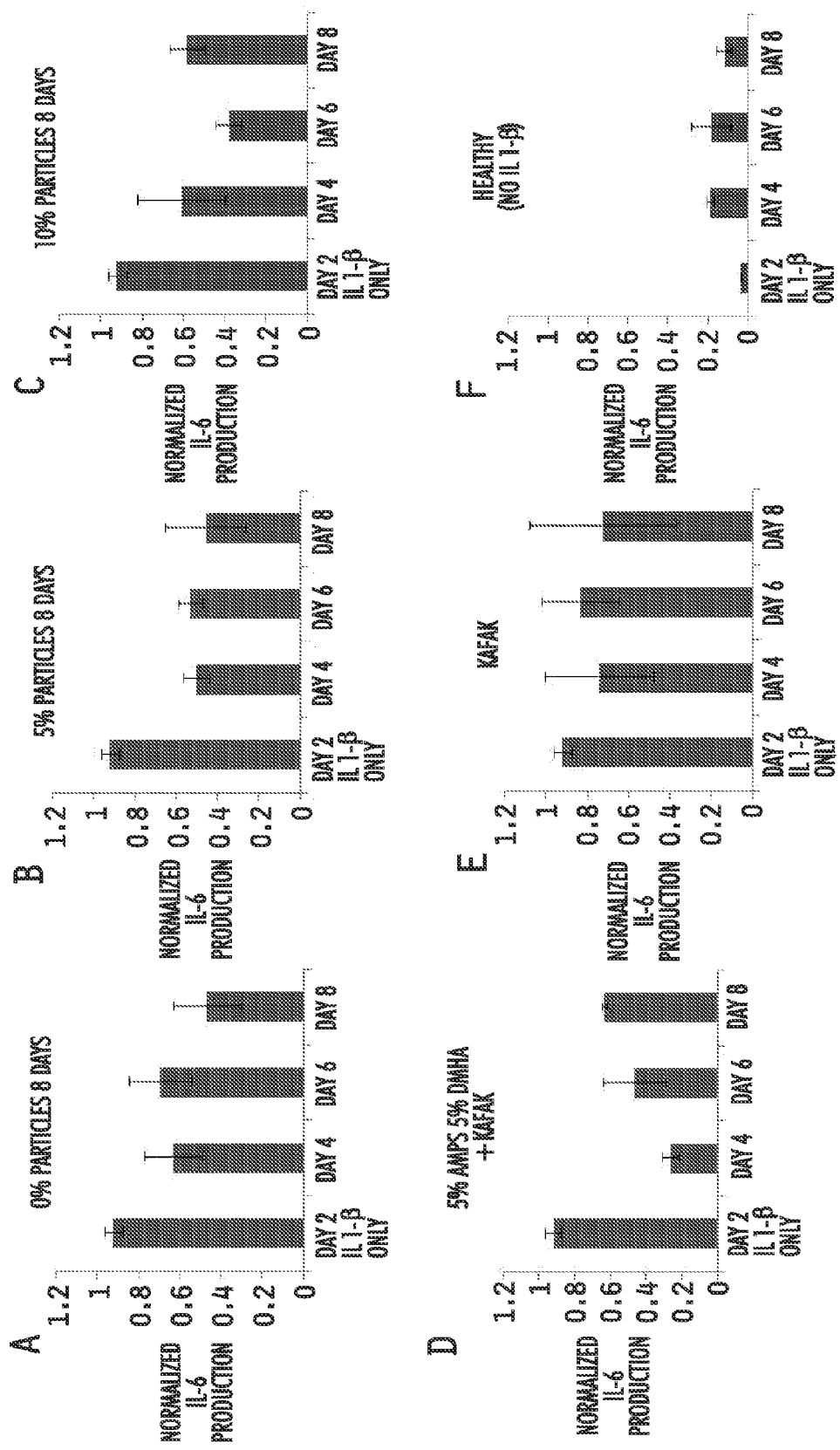
FIG. 26. IL-6 Production in Cartilage Plugs when dosed with 50 μg nanoparticles loaded with KAFAK. Plots are normalized to negative control using IL-1β only.

Nanoparticles loaded with KAFAK were then used to determine the therapeutic efficacy of reducing pro-inflammatory cytokine production in an inflamed cartilage plug. FIG. 26 demonstrates that after 2 days of IL-1B stimulated inflammation KAFAK loaded nanoparticles are able to reduce the production of IL-6 for 6 days of treatment. Similarly to FIG. 22, particles containing DMHA (FIG. 26 D) were able to release more therapeutically active KAFAK quicker than particles containing MBA. However, a slight reduction in activity was seen in KAFAK released from DMHA over time most likely due to enzymatic degradation of unprotected KAFAK free in serum. This was confirmed by a lack of therapeutic activity between 2 day measurements of KAFAK alone and was similar to previously reported serum half-life of KAFAK being less than 12 hours.

Example 26

Drug Loading & Release of Yara Nanoparticles

Nanoparticle Synthesis: NIPAm-AMPS-AAc nanoparticles were synthesized in a standard precipitation reaction. The monomers were dissolved in deionized water, and the solution was heated to 70° C. Potassium persulfate was then added to initiate polymerization. After 4 hours, the resultant nanoparticles were purified and lyophilized. Size and temperature sensitivity of the nanoparticles were measured via dynamic light scattering on a Malvern NANO-ZS90 Zetasizer.

Figure 27:
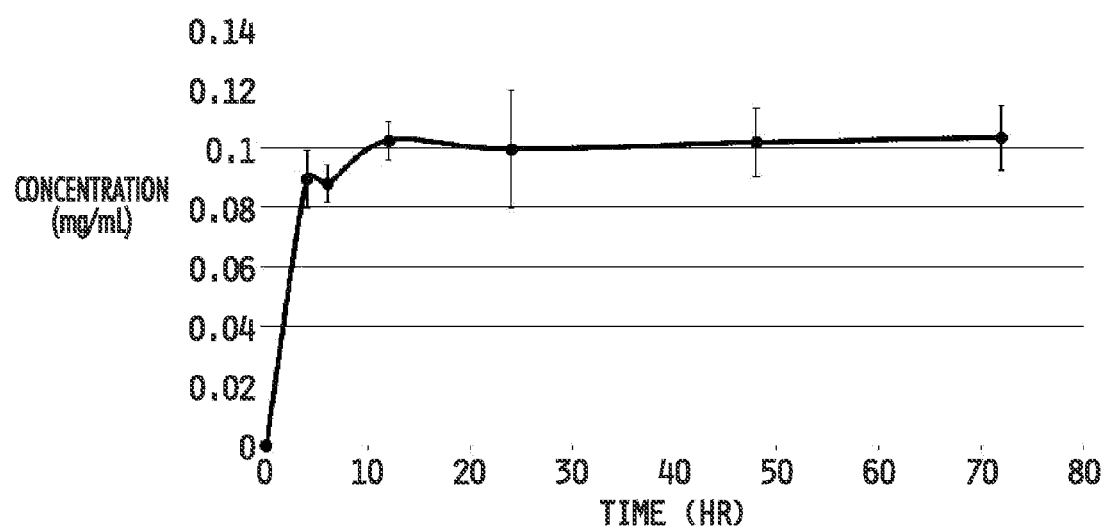
FIG. 27. Drug release profile of YARA from NIPAM-AMPS-AAc containing particles (crosslinked with MBA) in PBS over a 72 hour period.

YARA Peptide Loading and Release: Approximately 2 mg/mL of unmodified nanoparticles were incubated with 1 mg/mL of YARAAARQARAKALARQLGVAA (abbreviated YARA) peptide for 24 hours at 4° C. Nanoparticles loaded with YARA were then centrifuged and resuspended in PBS (pH 7.4). Aliquots of the suspension were obtained at various time points over 72 hours. FIG. 27 shows the results of a fluoraldehyde OPA assay used to quantify the amount of YARA peptide released from the nanoparticles over 72 hours.

What is claimed is:

1. A composition comprising:
   (i) at least one kinase inhibiting peptide incorporated with a nanoparticle, wherein the kinase inhibiting peptide is of Formula I:

Z1-X1-X2-X3-X4 X5-X6-X7-X8-X9-X10-Z2 wherein Z1 and Z2 are independently absent or are transduction domains;
   X1 is KA;
   X2 is L;
   X3 is selected from the group consisting of V, L, I, A, G, Q, N, S, T, and C;
   X4 is R;
   X5 is Q;
   X6 is L;
   X7 is selected from the group consisting of S, A, C, T, and G;
   X8 is V;
   X9 is A; and
   X10 is A or is absent,
   wherein the nanoparticle comprises at least one copolymerized monomer having an anionic side chain and at least one additional copolymerized monomer, wherein the at least one copolymerized anionic monomer is 2-acrylamido-2-methyl-1-propanesulfonic acid (AMPS), wherein the AMPS is effective to increase drug loading and control drug release;
   (ii) a crosslinker, wherein the crosslinker is selected from the group consisting of N,O dimethacryloylhydroxylamine, divinyl adipate, N,N-Bis(acryloyl)cystamine and N,N'-methylenebisacrylamide; and
   (iii) a stabilizer that is coupled to the nanoparticle, wherein the stabilizer is effective to reduce aggregation of the nanoparticles to maintain the stability of the nanoparticles.

2. The composition of claim 1 wherein the kinase inhibiting peptide is an MK2 inhibitor peptide.

3. The composition of claim 1 wherein the amino acid sequence of the kinase inhibiting peptide has at least 90% sequence identity to a peptide selected from the group consisting of YARAAARQARAKALARQLGVAA (SEQ ID NO: 1), YARAAARQARAKALNRQLGVA (SEQ ID NO: 2), FAKLAAR LYRKALARQLGVAA (SEQ ID NO: 3), KAFAKLAARLYRKALARQLGVAA (SEQ ID NO: 4), HRRIKAWLKKIKALARQLGVAA (SEQ ID NO: 5), YARAAARQARAKALNRQLAVAA (SEQ ID NO: 6) and YARAAARQARAKALNRQLAVA (SEQ ID NO: 7).

4. The composition of claim 1 wherein the at least one additional copolymerized monomer is N-isopropylacrylamide.

5. A dose of the composition of claim 1 effective to treat inflammation for administration to a patient in need thereof, wherein the effective dose ranges from about 1 pg to about 10 ng per kilogram of body weight.

6. The composition of claim 1 wherein the at least one copolymerized anionic monomer is 2-acrylamido-2-methyl-1-propanesulfonic acid, and wherein the at least one additional copolymerized monomer is N-isopropylacrylamide.

7. The composition of claim 1 wherein the at least one additional copolymerized monomer and the copolymerized anionic monomer are present in the composition at a ratio of about 10:1.

8. A method for treating osteoarthritis, the method comprising the step of administering a composition comprising:
(i) at least one kinase inhibiting peptide incorporated with a nanoparticle,
wherein the kinase inhibiting peptide is of Formula I:

Z1-X1-X2-X3-X4X5-X6-X7-X8-X9-X10-Z2 wherein Z1 and Z2 are independently absent or are transduction domains;
X1 is KA;
X2 is L;
X3 is selected from the group consisting of V, L, I, A, G, Q, N, S, T, and C;
X4 is R;
X5 is Q;
X6 is L;
X7 is selected from the group consisting of S, A, C, T, and G;
X8 is V;
X9 is A; and
X10 is A or is absent,
wherein the nanoparticle comprises at least one copolymerized anionic monomer and at least one additional copolymerized monomer, wherein the at least one copolymerized anionic monomer is 2-acrylamido-2-methyl-1-propanesulfonic acid (AMPS), wherein the AMPS is effective to increase drug loading and control drug release;
(ii) a crosslinker, wherein the crosslinker is selected from the group consisting of N,O dimethacryloylhydroxylamine, divinyl adipate, N,N-Bis(acryloyl)cystamine, and N,N'-methylenebisacrylamide; and
(iii) a stabilizer that is coupled to the nanoparticle, wherein the stabilizer is effective to reduce aggregation of the nanoparticles to maintain the stability of the nanoparticles.

9. The method of claim 8 wherein the kinase inhibiting peptide is an MK2 inhibitor peptide.

10. The method of claim 8 wherein the amino acid sequence of the kinase inhibiting peptide has at least 90% sequence identity to a peptide selected from the group consisting of YARAAARQARAKALARQLGVAA (SEQ ID NO: 1), YARAAARQARAKALNRQLGVA (SEQ ID NO: 2), FAKLAAR LYRKALARQLGVAA (SEQ ID NO: 3), KAFAKLAARLYRKALARQLGVAA (SEQ ID NO: 4), HRRIKAWLKKIKALARQLGVAA (SEQ ID NO: 5), YARAAARQARAKALNRQLAVAA (SEQ ID NO: 6), and YARAAARQARAKALNRQLAVA (SEQ ID NO: 7).

11. The method of claim 8 wherein the at least one copolymerized anionic monomer is 2-acrylamido-2-methyl-1-propanesulfonic acid.

12. The method of claim 8 wherein the at least one additional copolymerized monomer is N-isopropylacrylamide.

13. The method of claim 8 wherein the nanoparticle further comprising a crosslinker.

14. The method of claim 13 wherein the crosslinker is selected from the group consisting of N,O-dimethacryloylhydroxylamine, divinyl adipate, N,N-Bis(acryloyl)cystamine, and N,N'-methylenebisacrylamide.

15. The method of claim 8 wherein the at least one additional copolymerized monomer and the copolymerized anionic monomer are present in the composition at a ratio of about 10:1.

16. The composition of claim 1 wherein the anionic monomer is a sulfonic monomer.

17. The method of claim 8 wherein the anionic monomer is a sulfonic monomer.

* * * * *

SEQUENCE LISTING

<160> NUMBER OF SEQ ID NOS: 7

<210> SEQ ID NO 1
<211> LENGTH: 22
<212> TYPE: PRT
<213> ORGANISM: Unknown
<220> FEATURE:
<223> OTHER INFORMATION: Mammalian

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 2
<211> LENGTH: 21
<212> TYPE: PRT
<213> ORGANISM: Unknown
<220> FEATURE:
<223> OTHER INFORMATION: Mammalian

<400> SEQUENCE: 2

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 3
<211> LENGTH: 21
<212> TYPE: PRT
<213> ORGANISM: Unknown
<220> FEATURE:
<223> OTHER INFORMATION: Mammalian

<400> SEQUENCE: 3

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 4
<211> LENGTH: 23
<212> TYPE: PRT
<213> ORGANISM: Unknown
<220> FEATURE:
<223> OTHER INFORMATION: Mammallian

<400> SEQUENCE: 4

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 5
<211> LENGTH: 22
<212> TYPE: PRT
<213> ORGANISM: Unknown
<220> FEATURE:
<223> OTHER INFORMATION: Mammalian

```
<400> SEQUENCE: 5

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 6
<211> LENGTH: 22
<212> TYPE: PRT
<213> ORGANISM: Unknown
<220> FEATURE:
<223> OTHER INFORMATION: Mammalian

<400> SEQUENCE: 6

Tyr Ala Arg Ala Ala Ala Arg Gln Ala Arg Ala Lys Ala Leu Asn Arg
1               5                   10                  15

Gln Leu Ala Val Ala Ala
            20

<210> SEQ ID NO 7
<211> LENGTH: 21
<212> TYPE: PRT
<213> ORGANISM: Unknown
<220> FEATURE:
<223> OTHER INFORMATION: Mammalian

<400> SEQUENCE: 7

Tyr Ala Arg Ala Ala Ala Arg Gln Ala Arg Ala Lys Ala Leu Asn Arg
1               5                   10                  15

Gln Leu Ala Val Ala
            20
```